United States Patent [19]
Chamberlain et al.

[11] Patent Number: 6,057,158
[45] Date of Patent: May 2, 2000

[54] ADENOVIRUS VECTORS

[75] Inventors: Jeffrey S. Chamberlain; Dennis J. Hartigan-O'Connor, both of Ann Arbor, Mich.

[73] Assignee: Regents of the University of Michigan, Ann Arbor, Mich.

[21] Appl. No.: 09/315,372

[22] Filed: May 18, 1999

Related U.S. Application Data

[63] Continuation of application No. 08/735,609, Oct. 23, 1996.
[51] Int. Cl.[7] ............................. C12N 5/10; C12N 15/861
[52] U.S. Cl. ........................... 435/456; 435/325; 435/369
[58] Field of Search ................................ 435/320.1, 325, 435/369, 456

[56] References Cited

U.S. PATENT DOCUMENTS 5,919,676  7/1999  Graham et al. ........................ 435/91.4

*Primary Examiner*—Robert A. Schwartzman
*Attorney, Agent, or Firm*—Medlen & Carroll, LLP

[57] ABSTRACT

The present invention provides improved adenovirus vectors and packaging cell lines. One type of improved adenoviral vector comprises deletions within the E2b region of the adenoviral genome. These E2b-deleted virus are used in conjunction with novel cell lines that constitutively express E2b gene products. The present invention further provides adenoviral vectors deleted for all viral coding regions. These "gutted" vectors permit the transfer of large genes to cells as demonstrated herein by the transfer of the dystrophin gene to the muscle of mice. The E2b-deleted vectors and the gutted vectors provide improved adenoviral vectors useful for a wide variety of gene therapy applications.

10 Claims, 19 Drawing Sheets

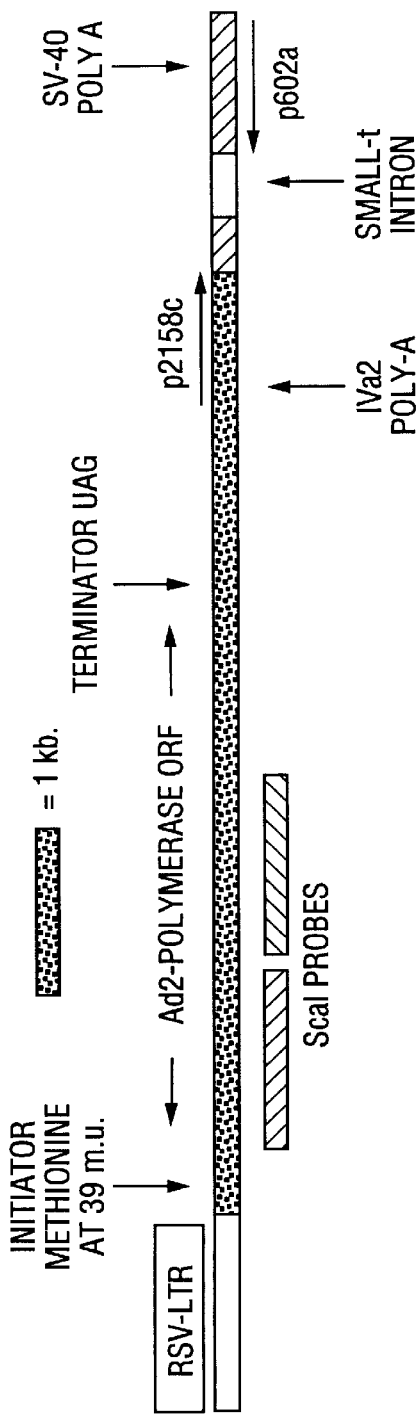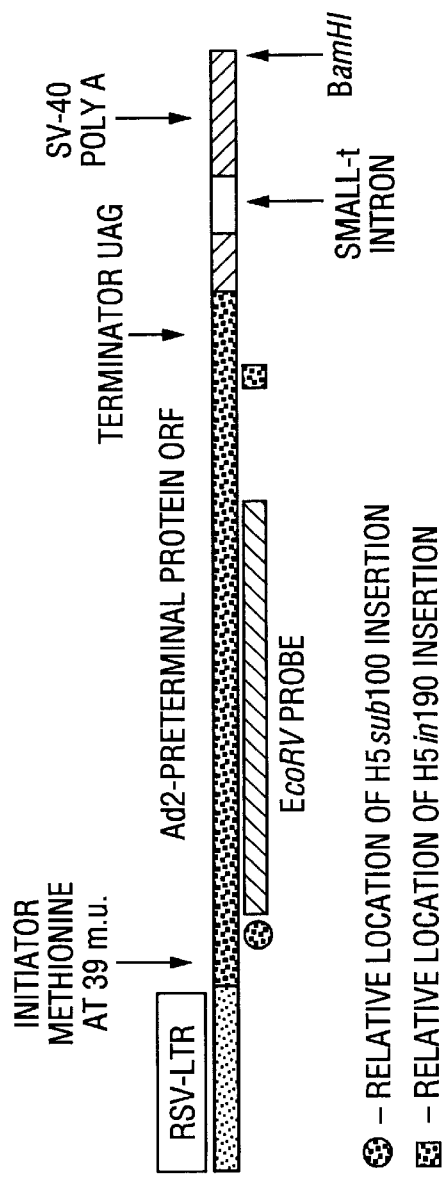
FIG. 1A
FIG. 1B

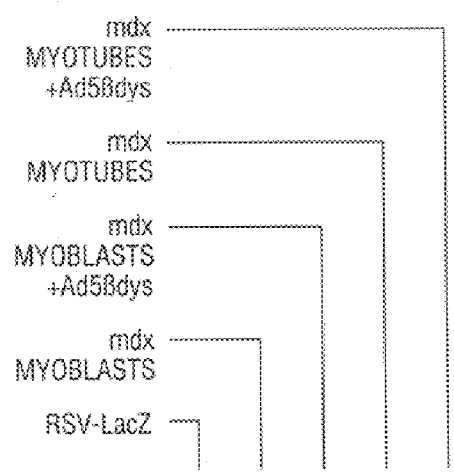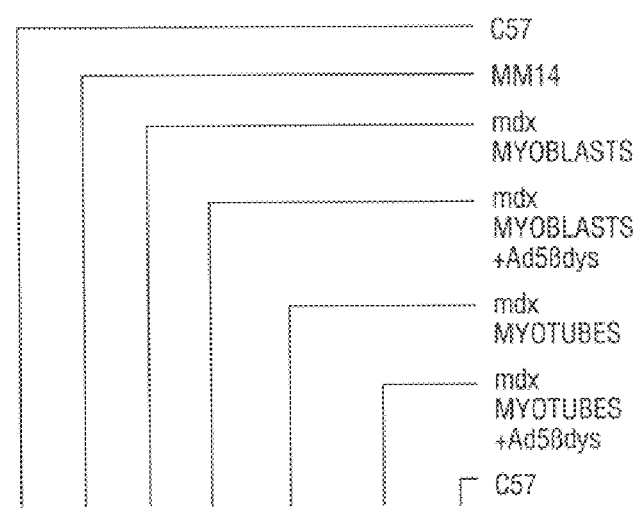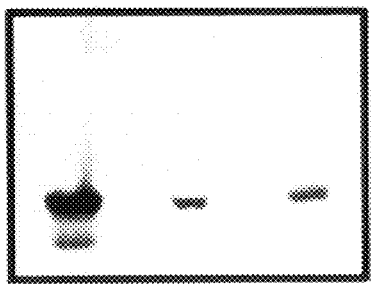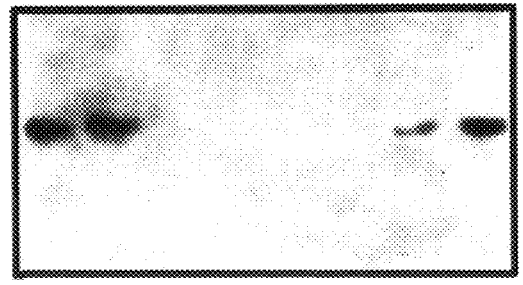
FIG. 15A    FIG. 15B

```
                              SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
         (A) LENGTH: 35935 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:1:

CATCATCAAT AATATACCTT ATTTTGGATT GAAGCCAATA TGATAATGAG GGGGTGGAGT       60

TTGTGACGTG GCGCGGGGCG TGGGAACGGG GCGGGTGACG TAGTAGTGTG GCGGAAGTGT      120

GATGTTGCAA GTGTGGCGGA ACACATGTAA GCGACGGATG TGGCAAAAGT GACGTTTTTG      180

GTGTGCGCCG GTGTACACAG GAAGTGACAA TTTTCGCGCG GTTTTAGGCG GATGTTGTAG      240

TAAATTTGGG CGTAACCGAG TAAGATTTGG CCATTTTCGC GGGAAAACTG AATAAGAGGA      300

AGTGAAATCT GAATAATTTT GTGTTACTCA TAGCGCGTAA TATTTGTCTA GGGCCGCGGG      360

GACTTTGACC GTTTACGTGG AGACTCGCCC AGGTGTTTTT CTCAGGTGTT TTCCGCGTTC      420

CGGGTCAAAG TTGGCGTTTT ATTATTATAG TCAGCTGACG TGTAGTGTAT TTATACCCGG      480

TGAGTTCCTC AAGAGGCCAC TCTTGAGTGC CAGCGAGTAG AGTTTTCTCC TCCGAGCCGC      540

TCCGACACCG GGACTGAAAA TGAGACATAT TATCTGCCAC GGAGGTGTTA TTACCGAAGA      600

AATGGCCGCC AGTCTTTTGG ACCAGCTGAT CGAAGAGGTA CTGGCTGATA ATCTTCCACC      660

TCCTAGCCAT TTTGAACCAC CTACCCTTCA CGAACTGTAT GATTTAGACG TGACGGCCCC      720

CGAAGATCCC AACGAGGAGG CGGTTTCGCA GATTTTTCCC GACTCTGTAA TGTTGGCGGT      780

GCAGGAAGGG ATTGACTTAC TCACTTTTCC GCCGGCGCCC GGTTCTCCGG AGCCGCCTCA      840

CCTTTCCCGG CAGCCCGAGC AGCCGGAGCA GAGAGCCTTG GGTCCGGTTT CTATGCCAAA      900

CCTTGTACCG GAGGTGATCG ATCTTACCTG CCACGAGGCT GGCTTTCCAC CCAGTGACGA      960

CGAGGATGAA GAGGGTGAGG AGTTTGTGTT AGATTATGTG GAGCACCCCG GGCACGGTTG     1020

CAGGTCTTGT CATTATCACC GGAGGAATAC GGGGGACCCA GATATTATGT GTTCGCTTTG     1080

CTATATGAGG ACCTGTGGCA TGTTTGTCTA CAGTAAGTGA AAATTATGGG CAGTGGGTGA     1140

TAGAGTGGTG GGTTTGGTGT GGTAATTTTT TTTTTAATTT TTACAGTTTT GTGGTTTAAA     1200

GAATTTTGTA TTGTGATTTT TTTAAAAGGT CCTGTGTCTG AACCTGAGCC TGAGCCCGAG     1260

CCAGAACCGG AGCCTGCAAG ACCTACCCGC CGTCCTAAAA TGGCGCCTGC TATCCTGAGA     1320

CGCCCGACAT CACCTGTGTC TAGAGAATGC AATAGTAGTA CGGATAGCTG TGACTCCGGT     1380

CCTTCTAACA CACCTCCTGA GATACACCCG GTGGTCCCGC TGTGCCCCAT TAAACCAGTT     1440

GCCGTGAGAG TTGGTGGGCG TCGCCAGGCT GTGGAATGTA TCGAGGACTT GCTTAACGAG     1500

CCTGGGCAAC CTTTGGACTT GAGCTGTAAA CGCCCCAGGC CATAAGGTGT AAACCTGTGA     1560
```

```
TTGCGTGTGT GGTTAACGCC TTTGTTTGCT GAATGAGTTG ATGTAAGTTT AATAAAGGGT    1620

GAGATAATGT TTAACTTGCA TGGCGTGTTA AATGGGGCGG GGCTTAAAGG GTATATAATG    1680

CGCCGTGGGC TAATCTTGGT TACATCTGAC CTCATGGAGG CTTGGGAGTG TTTGGAAGAT    1740

TTTTCTGCTG TGCGTAACTT GCTGGAACAG AGCTCTAACA GTACCTCTTG GTTTTGGAGG    1800

TTTCTGTGGG GCTCATCCCA GGCAAAGTTA GTCTGCAGAA TTAAGGAGGA TTACAAGTGG    1860

GAATTTGAAG AGCTTTTGAA ATCCTGTGGT GAGCTGTTTG ATTCTTTGAA TCTGGGTCAC    1920

CAGGCGCTTT TCCAAGAGAA GGTCATCAAG ACTTTGGATT TTTCCACACC GGGGCGCGCT    1980

GCGGCTGCTG TTGCTTTTTT GAGTTTTATA AAGGATAAAT GGAGCGAAGA AACCCATCTG    2040

AGCGGGGGGT ACCTGCTGGA TTTTCTGGCC ATGCATCTGT GGAGAGCGGT TGTGAGACAC    2100

AAGAATCGCC TGCTACTGTT GTCTTCCGTC CGCCCGGCGA TAATACCGAC GGAGGAGCAG    2160

CAGCAGCAGC AGGAGGAAGC CAGGCGGCGG CGGCAGGAGC AGAGCCCATG GAACCCGAGA    2220

GCCGGCCTGG ACCCTCGGGA ATGAATGTTG TACAGGTGGC TGAACTGTAT CCAGAACTGA    2280

GACGCATTTT GACAATTACA GAGGATGGGC AGGGGCTAAA GGGGGTAAAG AGGGAGCGGG    2340

GGGCTTGTGA GGCTACAGAG GAGGCTAGGA ATCTAGCTTT TAGCTTAATG ACCAGACACC    2400

GTCCTGAGTG TATTACTTTT CAACAGATCA AGGATAATTG CGCTAATGAG CTTGATCTGC    2460

TGGCGCAGAA GTATTCCATA GAGCAGCTGA CCACTTACTG GCTGCAGCCA GGGGATGATT    2520

TTGAGGAGGC TATTAGGGTA TATGCAAAGG TGGCACTTAG GCCAGATTGC AAGTACAAGA    2580

TCAGCAAACT TGTAAATATC AGGAATTGTT GCTACATTTC TGGGAACGGG GCCGAGGTGG    2640

AGATAGATAC GGAGGATAGG GTGGCCTTTA GATGTAGCAT GATAAATATG TGGCCGGGGG    2700

TGCTTGGCAT GGACGGGGTG GTTATTATGA ATGTAAGGTT TACTGGCCCC AATTTTAGCG    2760

GTACGGTTTT CCTGGCCAAT ACCAACCTTA TCCTACACGG TGTAAGCTTC TATGGGTTTA    2820

ACAATACCTG TGTGGAAGCC TGGACCGATG TAAGGGTTCG GGGCTGTGCC TTTTACTGCT    2880

GCTGGAAGGG GGTGGTGTGT CGCCCCAAAA GCAGGGCTTC AATTAAGAAA TGCCTCTTTG    2940

AAAGGTGTAC CTTGGGTATC CTGTCTGAGG GTAACTCCAG GGTGCGCCAC AATGTGGCCT    3000

CCGACTGTGG TTGCTTCATG CTAGTGAAAA GCGTGGCTGT GATTAAGCAT AACATGGTAT    3060

GTGGCAACTG CGAGGACAGG GCCTCTCAGA TGCTGACCTG CTCGGACGGC AACTGTCACC    3120

TGCTGAAGAC CATTCACGTA GCCAGCCACT CTCGCAAGGC CTGGCCAGTG TTTGAGCATA    3180

ACATACTGAC CCGCTGTTCC TTGCATTTGG GTAACAGGAG GGGGGTGTTC CTACCTTACC    3240

AATGCAATTT GAGTCACACT AAGATATTGC TTGAGCCCGA GAGCATGTCC AAGGTGAACC    3300

TGAACGGGGT GTTTGACATG ACCATGAAGA TCTGGAAGGT GCTGAGGTAC GATGAGACCC    3360

GCACCAGGTG CAGACCCTGC GAGTGTGGCG GTAAACATAT TAGGAACCAG CCTGTGATGC    3420

TGGATGTGAC CGAGGAGCTG AGGCCCGATC ACTTGGTGCT GGCCTGCACC CGCGCTGAGT    3480

TTGGCTCTAG CGATGAAGAT ACAGATTGAG GTACTGAAAT GTGTGGGCGT GGCTTAAGGG    3540

TGGGAAAGAA TATATAAGGT GGGGGTCTTA TGTAGTTTTG TATCTGTTTT GCAGCAGCCG    3600

CCGCCGCCAT GAGCACCAAC TCGTTTGATG GAAGCATTGT GAGCTCATAT TTGACAACGC    3660

GCATGCCCCC ATGGGCCGGG GTGCGTCAGA ATGTGATGGG CTCCAGCATT GATGGTCGCC    3720

CCGTCCTGCC CGCAAACTCT ACTACCTTGA CCTACGAGAC CGTGTCTGGA ACGCCGTTGG    3780

AGACTGCAGC CTCCGCCGCC GCTTCAGCCG CTGCAGCCAC CGCCCGCGGG ATTGTGACTG    3840

ACTTTGCTTT CCTGAGCCCG CTTGCAAGCA GTGCAGCTTC CCGTTCATCC GCCCGCGATG    3900

ACAAGTTGAC GGCTCTTTTG GCACAATTGG ATTCTTTGAC CCGGGAACTT AATGTCGTTT    3960
```

-continued

```
CTCAGCAGCT GTTGGATCTG CGCCAGCAGG TTTCTGCCCT GAAGGCTTCC TCCCCTCCCA    4020

ATGCGGTTTA AAACATAAAT AAAAAACCAG ACTCTGTTTG GATTTGGATC AAGCAAGTGT    4080

CTTGCTGTCT TTATTTAGGG GTTTTGCGCG CGCGGTAGGC CCGGGACCAG CGGTCTCGGT    4140

CGTTGAGGGT CCTGTGTATT TTTTCCAGGA CGTGGTAAAG GTGACTCTGG ATGTTCAGAT    4200

ACATGGGCAT AAGCCCGTCT CTGGGGTGGA GGTAGCACCA CTGCAGAGCT TCATGCTGCG    4260

GGGTGGTGTT GTAGATGATC CAGTCGTAGC AGGAGCGCTG GGCGTGGTGC CTAAAAATGT    4320

CTTTCAGTAG CAAGCTGATT GCCAGGGGCA GGCCCTTGGT GTAAGTGTTT ACAAAGCGGT    4380

TAAGCTGGGA TGGGTGCATA CGTGGGGATA TGAGATGCAT CTTGGACTGT ATTTTTAGGT    4440

TGGCTATGTT CCCAGCCATA TCCCTCCGGG GATTCATGTT GTGCAGAACC ACCAGCACAG    4500

TGTATCCGGT GCACTTGGGA AATTTGTCAT GTAGCTTAGA AGGAAATGCG TGGAAGAACT    4560

TGGAGACGCC CTTGTGACCT CCAAGATTTT CCATGCATTC GTCCATAATG ATGGCAATGG    4620

GCCCACGGGC GGCGGCCTGG GCGAAGATAT TTCTGGGATC ACTAACGTCA TAGTTGTGTT    4680

CCAGGATGAG ATCGTCATAG GCCATTTTTA CAAAGCGCGG GCGGAGGGTG CCAGACTGCG    4740

GTATAATGGT TCCATCCGGC CCAGGGGCGT AGTTACCCTC ACAGATTTGC ATTTCCCACG    4800

CTTTGAGTTC AGATGGGGGG ATCATGTCTA CCTGCGGGGC GATGAAGAAA ACGGTTTCCG    4860

GGGTAGGGGA GATCAGCTGG GAAGAAAGCA GGTTCCTGAG CAGCTGCGAC TTACCGCAGC    4920

CGGTGGGCCC GTAAATCACA CCTATTACCG GGTGCAACTG GTAGTTAAGA GAGCTGCAGC    4980

TGCCGTCATC CCTGAGCAGG GGGGCCACTT CGTTAAGCAT GTCCCTGACT CGCATGTTTT    5040

CCCTGACCAA ATCCGCCAGA AGGCGCTCGC CGCCCAGCGA TAGCAGTTCT TGCAAGGAAG    5100

CAAAGTTTTT CAACGGTTTG AGACCGTCCG CCGTAGGCAT GCTTTTGAGC GTTTGACCAA    5160

GCAGTTCCAG GCGGTCCCAC AGCTCGGTCA CCTGCTCTAC GGCATCTCGA TCCAGCATAT    5220

CTCCTCGTTT CGCGGGTTGG GGCGGCTTTC GCTGTACGGC AGTAGTCGGT GCTCGTCCAG    5280

ACGGGCCAGG GTCATGTCTT TCCACGGGCG CAGGGTCCTC GTCAGCGTAG TCTGGGTCAC    5340

GGTGAAGGGG TGCGCTCCGG GCTGCGCGCT GGCCAGGGTG CGCTTGAGGC TGGTCCTGCT    5400

GGTGCTGAAG CGCTGCCGGT CTTCGCCCTG CGCGTCGGCC AGGTAGCATT TGACCATGGT    5460

GTCATAGTCC AGCCCCTCCG CGGCGTGGCC CTTGGCGCGC AGCTTGCCCT TGGAGGAGGC    5520

GCCGCACGAG GGGCAGTGCA GACTTTTGAG GGCGTAGAGC TTGGGCGCGA GAAATACCGA    5580

TTCCGGGGAG TAGGCATCCG CGCCGCAGGC CCCGCAGACG GTCTCGCATT CCACGAGCCA    5640

GGTGAGCTCT GGCCGTTCGG GGTCAAAAAC CAGGTTTCCC CCATGCTTTT TGATGCGTTT    5700

CTTACCTCTG GTTTCCATGA GCCGGTGTCC ACGCTCGGTG ACGAAAAGGC TGTCCGTGTC    5760

CCCGTATACA GACTTGAGAG GCCTGTCCTC GAGCGGTGTT CCGCGGTCCT CCTCGTATAG    5820

AAACTCGGAC CACTCTGAGA CAAAGGCTCG CGTCCAGGCC AGCACGAAGG AGGCTAAGTG    5880

GGAGGGGTAG CGGTCGTTGT CCACTAGGGG GTCCACTCGC TCCAGGGTGT GAAGACACAT    5940

GTCGCCCTCT TCGGCATCAA GGAAGGTGAT TGGTTTGTAG GTGTAGGCCA CGTGACCGGG    6000

TGTTCCTGAA GGGGGGCTAT AAAAGGGGGT GGGGCGCGT TCGTCCTCAC TCTCTTCCGC    6060

ATCGCTGTCT GCGAGGGCCA GCTGTTGGGG TGAGTACTCC CTCTGAAAAG CGGGCATGAC    6120

TTCTGCGCTA AGATTGTCAG TTTCCAAAAA CGAGGAGGAT TTGATATTCA CCTGGCCCGC    6180

GGTGATGCCT TTGAGGGTGG CCGCATCCAT CTGGTCAGAA AAGACAATCT TTTTGTTGTC    6240

AAGCTTGGTG GCAAACGACC CGTAGAGGGC GTTGGACAGC AACTTGGCGA TGGAGCGCAG    6300
```

```
GGTTTGGTTT TTGTCGCGAT CGGCGCGCTC CTTGGCCGCG ATGTTTAGCT GCACGTATTC    6360

GCGCGCAACG CACCGCCATT CGGGAAAGAC GGTGGTGCGC TCGTCGGGCA CCAGGTGCAC    6420

GCGCCAACCG CGGTTGTGCA GGGTGACAAG GTCAACGCTG GTGGCTACCT CTCCGCGTAG    6480

GCGCTCGTTG GTCCAGCAGA GGCGGCCGCC CTTGCGCGAG CAGAATGGCG GTAGGGGTC    6540

TAGCTGCGTC TCGTCCGGGG GGTCTGCGTC CACGGTAAAG ACCCCGGGCA GCAGGCGCGC    6600

GTCGAAGTAG TCTATCTTGC ATCCTTGCAA GTCTAGCGCC TGCTGCCATG CGCGGGCGGC    6660

AAGCGCGCGC TCGTATGGGT TGAGTGGGGG ACCCCATGGC ATGGGGTGGG TGAGCGCGGA    6720

GGCGTACATG CCGCAAATGT CGTAAACGTA GAGGGGCTCT CTGAGTATTC AAGATATGT     6780

AGGGTAGCAT CTTCCACCGC GGATGCTGGC GCGCACGTAA TCGTATAGTT CGTGCGAGGG    6840

AGCGAGGAGG TCGGGACCGA GGTTGCTACG GGCGGGCTGC TCTGCTCGGA AGACTATCTG    6900

CCTGAAGATG CATGTGAGT TGGATGATAT GGTTGGACGC TGGAAGACGT TGAAGCTGGC     6960

GTCTGTGAGA CCTACCGCGT CACGCACGAA GGAGGCGTAG GAGTCGCGCA GCTTGTTGAC    7020

CAGCTCGGCG GTGACCTGCA CGTCTAGGGC GCAGTAGTCC AGGGTTTCCT TGATGATGTC    7080

ATACTTATCC TGTCCCTTTT TTTTCCACAG CTCGCGGTTG AGGACAAACT CTTCGCGGTC    7140

TTTCCAGTAC TCTTGGATCG GAAACCCGTC GGCCTCCGAA CGGTAAGAGC CTAGCATGTA    7200

GAACTGGTTG ACGGCCTGGT AGGCGCAGCA TCCCTTTTCT ACGGGTAGCG CGTATGCCTG    7260

CGCGGCCTTC CGGAGCGAGG TGTGGGTGAG CGCAAAGGTG TCCCTGACCA TGACTTTGAG    7320

GTACTGGTAT TTGAAGTCAG TGTCGTCGCA TCCGCCCTGC TCCCAGAGCA AAAAGTCCGT    7380

GCGCTTTTTG GAACGCGGAT TTGGCAGGGC GAAGGTGACA TCGTTGAAGA GTATCTTTCC    7440

CGCGCGAGGC ATAAAGTTGC GTGTGATGCG GAAGGGTCCC GGCACCTCGG AACGGTTGTT    7500

AATTACCTGG GCGGCGAGCA CGATCTCGTC AAAGCCGTTG ATGTTGTGGC CCACAATGTA    7560

AAGTTCCAAG AAGCGCGGGA TGCCCTTGAT GGAAGGCAAT TTTTTAAGTT CCTCGTAGGT    7620

GAGCTCTTCA GGGGAGCTGA GCCCGTGCTC TGAAAGGGCC CAGTCTGCAA GATGAGGGTT    7680

GGAAGCGACG AATGAGCTCC ACAGGTCACG GGCCATTAGC ATTTGCAGGT GGTCGCGAAA    7740

GGTCCTAAAC TGGCGACCTA TGGCCATTTT TTCTGGGGTG ATGCAGTAGA AGGTAAGCGG    7800

GTCTTGTTCC CAGCGGTCCC ATCCAAGGTT CGCGGCTAGG TCTCGCGCGG CAGTCACTAG    7860

AGGCTCATCT CCGCCGAACT TCATGACCAG CATGAAGGGC ACGAGCTGCT TCCCAAAGGC    7920

CCCCATCCAA GTATAGGTCT CTACATCGTA GGTGACAAAG AGACGCTCGG TGCGAGGATG    7980

CGAGCCGATC GGGAAGAACT GGATCTCCCG CCACCAATTG GAGGAGTGGC TATTGATGTG    8040

GTGAAAGTAG AAGTCCCTGC GACGGGCCGA ACACTCGTGC TGGCTTTTGT AAAAACGTGC    8100

GCAGTACTGG CAGCGGTGCA CGGGCTGTAC ATCCTGCACG AGGTTGACCT GACGACCGCG    8160

CACAAGGAAG CAGAGTGGGA ATTTGAGCCC CTCGCCTGGC GGGTTTGGCT GGTGGTCTTC    8220

TACTTCGGCT GCTTGTCCTT GACCGTCTGG CTGCTCGAGG GGAGTTACGG TGGATCGGAC    8280

CACCACGCCG CGCGAGCCCA AAGTCCAGAT GTCCGCGCGC GGCGGTCGGA GCTTGATGAC    8340

AACATCGCGC AGATGGGAGC TGTCCATGGT CTGGAGCTCC CGCGGCGTCA GGTCAGGCGG    8400

GAGCTCCTGC AGGTTTACCT CGCATAGACG GGTCAGGGCG CGGGCTAGAT CCAGGTGATA    8460

CCTAATTTCC AGGGGCTGGT TGGTGGCGGC GTCGATGGCT TGCAAGAGGC CGCATCCCCG    8520

CGGCGCGACT ACGGTACCGC GCGGCGGGCG GTGGGCCGCG GGGGTGTCCT TGGATGATGC    8580

ATCTAAAAGC GGTGACGCGG GCGAGCCCCC GGAGGTAGGG GGGGCTCCGG ACCCGCCGGG    8640

AGAGGGGGCA GGGGCACGTC GGCGCCGCGC GCGGGCAGGA GCTGGTGCTG CGCGCGTAGG    8700
```

```
TTGCTGGCGA ACGCGACGAC GCGGCGGTTG ATCTCCTGAA TCTGGCGCCT CTGCGTGAAG    8760

ACGACGGGCC CGGTGAGCTT GAGCCTGAAA GAGAGTTCGA CAGAATCAAT TTCGGTGTCG    8820

TTGACGGCGG CCTGGCGCAA AATCTCCTGC ACGTCTCCTG AGTTGTCTTG ATAGGCGATC    8880

TCGGCCATGA ACTGCTCGAT CTCTTCCTCC TGGAGATCTC CGCGTCCGGC TCGCTCCACG    8940

GTGGCGGCGA GGTCGTTGGA AATGCGGGCC ATGAGCTGCG AGAAGGCGTT GAGGCCTCCC    9000

TCGTTCCAGA CGCGGCTGTA GACCACGCCC CCTTCGGCAT CGCGGGCGCG CATGACCACC    9060

TGCGCGAGAT TGAGCTCCAC GTGCCGGGCG AAGACGGCGT AGTTTCGCAG GCGCTGAAAG    9120

AGGTAGTTGA GGGTGGTGGC GGTGTGTTCT GCCACGAAGA AGTACATAAC CCAGCGTCGC    9180

AACGTGGATT CGTTGATATC CCCCAAGGCC TCAAGGCGCT CCATGGCCTC GTAGAAGTCC    9240

ACGGCGAAGT TGAAAAACTG GGAGTTGCGC GCCGACACGG TTAACTCCTC CTCCAGAAGA    9300

CGGATGAGCT CGGCGACAGT GTCGCGCACC TCGCGCTCAA AGGCTACAGG GGCCTCTTCT    9360

TCTTCTTCAA TCTCCTCTTC CATAAGGGCC TCCCCTTCTT CTTCTTCTGG CGGCGGTGGG    9420

GGAGGGGGGA CACGGCGGCG ACGACGGCGC ACCGGGAGGC GGTCGACAAA GCGCTCGATC    9480

ATCTCCCCGC GGCGACGGCG CATGGTCTCG GTGACGGCGC GGCCGTTCTC GCGGGGCGC    9540

AGTTGGAAGA CGCCGCCCGT CATGTCCCGG TTATGGGTTG GCGGGGGCT GCCATGCGGC    9600

AGGGATACGG CGCTAACGAT GCATCTCAAC AATTGTTGTG TAGGTACTCC GCCGCCGAGG    9660

GACCTGAGCG AGTCCGCATC GACCGGATCG GAAAACCTCT CGAGAAAGGC GTCTAACCAG    9720

TCACAGTCGC AAGGTAGGCT GAGCACCGTG GCGGGCGGCA GCGGGCGGCG GTCGGGGTTG    9780

TTTCTGGCGG AGGTGCTGCT GATGATGTAA TTAAAGTAGG CGGTCTTGAG ACGGCGGATG    9840

GTCGACAGAA GCACCATGTC CTTGGGTCCG GCCTGCTGAA TGCGCAGGCG GTCGGCCATG    9900

CCCCAGGCTT CGTTTTGACA TCGGCGCAGG TCTTTGTAGT AGTCTTGCAT GAGCCTTTCT    9960

ACCGGCACTT CTTCTTCTCC TTCCTCTTGT CCTGCATCTC TTGCATCTAT CGCTGCGGCG   10020

GCGGCGGAGT TTGGCCGTAG GTGGCGCCCT CTTCCTCCCA TGCGTGTGAC CCCGAAGCCC   10080

CTCATCGGCT GAAGCAGGGC TAGGTCGGCG ACAACGCGCT CGGCTAATAT GGCCTGCTGC   10140

ACCTGCGTGA GGGTAGACTG GAAGTCATCC ATGTCCACAA AGCGGTGGTA TGCGCCCGTG   10200

TTGATGGTGT AAGTGCAGTT GGCCATAACG GACCAGTTAA CGGTCTGGTG ACCCGGCTGC   10260

GAGAGCTCGG TGTACCTGAG ACGCGAGTAA GCCCTCGAGT CAAATACGTA GTCGTTGCAA   10320

GTCCGCACCA GGTACTGGTA TCCCACCAAA AAGTGCGGCG GCGGCTGGCG GTAGAGGGGC   10380

CAGCGTAGGG TGGCCGGGGC TCCGGGGCG AGATCTTCCA ACATAAGGCG ATGATATCCG   10440

TAGATGTACC TGGACATCCA GGTGATGCCG GCGGCGGTGG TGGAGGCGCG CGGAAAGTCG   10500

CGGACGCGGT TCCAGATGTT GCGCAGCGGC AAAAAGTGCT CCATGGTCGG GACGCTCTGG   10560

CCGGTCAGGC GCGCGCAATC GTTGACGCTC TAGACCGTGC AAAAGGAGAG CCTGTAAGCG   10620

GGCACTCTTC CGTGGTCTGG TGGATAAATT CGCAAGGGTA TCATGGCGGA CGACCGGGGT   10680

TCGAGCCCCG TATCCGGCCG TCCGCCGTGA TCCATGCGGT TACCGCCCGC GTGTCGAACC   10740

CAGGTGTGCG ACGTCAGACA ACGGGGGAGT GCTCCTTTTG GCTTCCTTCC AGGCGCGGCG   10800

GCTGCTGCGC TAGCTTTTTT GGCCACTGGC CGCGCGCAGC GTAAGCGGTT AGGCTGGAAA   10860

GCGAAAGCAT TAAGTGGCTC GCTCCCTGTA GCCGGAGGGT TATTTTCCAA GGGTTGAGTC   10920

GCGGGACCCC CGGTTCGAGT CTCGGACCGG CCGGACTGCG GCGAACGGGG GTTTGCCTCC   10980

CCGTCATGCA AGACCCCGCT TGCAAATTCC TCCGGAAACA GGGACGAGCC CCTTTTTTGC   11040
```

```
TTTTCCCAGA TGCATCCGGT GCTGCGGCAG ATGCGCCCCC CTCCTCAGCA GCGGCAAGAG   11100

CAAGAGCAGC GGCAGACATG CAGGGCACCC TCCCCTCCTC CTACCGCGTC AGGAGGGGCG   11160

ACATCCGCGG TTGACGCGGC AGCAGATGGT GATTACGAAC CCCCGCGCG CCGGGCCCGG    11220

CACTACCTGG ACTTGGAGGA GGGCGAGGGC CTGGCGCGGC TAGGAGCGCC CTCTCCTGAG   11280

CGGTACCCAA GGGTGCAGCT GAAGCGTGAT ACGCGTGAGG CGTACGTGCC GCGGCAGAAC   11340

CTGTTTCGCG ACCGCGAGGG AGAGGAGCCC GAGGAGATGC GGGATCGAAA GTTCCACGCA   11400

GGGCGCGAGC TGCGGCATGG CCTGAATCGC GAGCGGTTGC TGCGCGAGGA GGACTTTGAG   11460

CCCGACGCGC GAACCGGGAT TAGTCCCGCG CGCGCACACG TGGCGGCCGC CGACCTGGTA   11520

ACCGCATACG AGCAGACGGT GAACCAGGAG ATTAACTTTC AAAAAAGCTT TAACAACCAC   11580

GTGCGTACGC TTGTGGCGCG CGAGGAGGTG GCTATAGGAC TGATGCATCT GTGGGACTTT   11640

GTAAGCGCGC TGGAGCAAAA CCCAAATAGC AAGCCGCTCA TGGCGCAGCT GTTCCTTATA   11700

GTGCAGCACA GCAGGGACAA CGAGGCATTC AGGGATGCGC TGCTAAACAT AGTAGAGCCC   11760

GAGGGCCGCT GGCTGCTCGA TTTGATAAAC ATCCTGCAGA GCATAGTGGT GCAGGAGCGC   11820

AGCTTGAGCC TGGCTGACAA GGTGGCCGCC ATCAACTATT CCATGCTTAG CCTGGGCAAG   11880

TTTTACGCCC GCAAGATATA CCATACCCCT TACGTTCCCA TAGACAAGGA GGTAAAGATC   11940

GAGGGGTTCT ACATGCGCAT GGCGCTGAAG GTGCTTACCT TGAGCGACGA CCTGGGCGTT   12000

TATCGCAACG AGCGCATCCA CAAGGCCGTG AGCGTGAGCC GGCGGCGCGA GCTCAGCGAC   12060

CGCGAGCTGA TGCACAGCCT GCAAAGGGCC CTGGCTGGCA CGGGCAGCGG CGATAGAGAG   12120

GCCGAGTCCT ACTTTGACGC GGGCGCTGAC CTGCGCTGGG CCCCAAGCCG ACGCGCCCTG   12180

GAGGCAGCTG GGGCCGGACC TGGGCTGGCG GTGGCACCCG CGCGCGCTGG CAACGTCGGC   12240

GGCGTGGAGG AATATGACGA GGACGATGAG TACGAGCCAG AGGACGGCGA GTACTAAGCG   12300

GTGATGTTTC TGATCAGATG ATGCAAGACG CAACGGACCC GGCGGTGCGG GCGGCGCTGC   12360

AGAGCCAGCC GTCCGGCCTT AACTCCACGG ACGACTGGCG CCAGGTCATG GACCGCATCA   12420

TGTCGCTGAC TGCGCGCAAT CCTGACGCGT TCCGGCAGCA GCCGCAGGCC AACCGGCTCT   12480

CCGCAATTCT GGAAGCGGTG GTCCCGGCGC GCGCAAACCC CACGCACGAG AAGGTGCTGG   12540

CGATCGTAAA CGCGCTGGCC GAAAACAGGG CCATCCGGCC CGACGAGGCC GGCCTGGTCT   12600

ACGACGCGCT GCTTCAGCGC GTGGCTCGTT ACAACAGCGG CAACGTGCAG ACCAACCTGG   12660

ACCGGCTGGT GGGGGATGTG CGCGAGGCCG TGGCGCAGCG TGAGCGCGCG CAGCAGCAGG   12720

GCAACCTGGG CTCCATGGTT GCACTAAACG CCTTCCTGAG TACACAGCCC GCCAACGTGC   12780

CGCGGGACA GGAGGACTAC ACCAACTTTG TGAGCGCACT GCGGCTAATG GTGACTGAGA    12840

CACCGCAAAG TGAGGTGTAC CAGTCTGGGC CAGACTATTT TTTCCAGACC AGTAGACAAG   12900

GCCTGCAGAC CGTAAACCTG AGCCAGGCTT TCAAAAACTT GCAGGGGCTG TGGGGGGTGC   12960

GGGCTCCCAC AGGCGACCGC GCGACCGTGT CTAGCTTGCT GACGCCCAAC TCGCGCCTGT   13020

TGCTGCTGCT AATAGCGCCC TTCACGGACA GTGGCAGCGT GTCCCGGGAC ACATACCTAG   13080

GTCACTTGCT GACACTGTAC CGCGAGGCCA TAGGTCAGGC GCATGTGGAC GAGCATACTT   13140

TCCAGGAGAT TACAAGTGTC AGCCGCGCGC TGGGGCAGGA GGACACGGGC AGCCTGGAGG   13200

CAACCCTAAA CTACCTGCTG ACCAACCGGC GGCAGAAGAT CCCCTCGTTG CACAGTTTAA   13260

ACAGCGAGGA GGAGCGCATT TTGCGCTACG TGCAGCAGAG CGTGAGCCTT AACCTGATGC   13320

GCGACGGGGT AACGCCCAGC GTGGCGCTGG ACATGACCGC GCGCAACATG GAACCGGGCA   13380

TGTATGCCTC AAACCGGCCG TTTATCAACC GCCTAATGGA CTACTTGCAT CGCGCGGCCG   13440
```

-continued

```
CCGTGAACCC CGAGTATTTC ACCAATGCCA TCTTGAACCC GCACTGGCTA CCGCCCCCTG    13500

GTTTCTACAC CGGGGGATTC GAGGTGCCCG AGGGTAACGA TGGATTCCTC TGGGACGACA    13560

TAGACGACAG CGTGTTTTCC CCGCAACCGC AGACCCTGCT AGAGTTGCAA CAGCGCGAGC    13620

AGGCAGAGGC GGCGCTGCGA AAGGAAAGCT TCCGCAGGCC AAGCAGCTTG TCCGATCTAG    13680

GCGCTGCGGC CCCGCGGTCA GATGCTAGTA GCCCATTTCC AAGCTTGATA GGGTCTCTTA    13740

CCAGCACTCG CACCACCCGC CCGCGCCTGC TGGGCGAGGA GGAGTACCTA AACAACTCGC    13800

TGCTGCAGCC GCAGCGCGAA AAAAACCTGC CTCCGGCATT TCCCAACAAC GGGATAGAGA    13860

GCCTAGTGGA CAAGATGAGT AGATGGAAGA CGTACGCGCA GGAGCACAGG GACGTGCCAG    13920

GCCCGCGCCC GCCCACCCGT CGTCAAAGGC ACGACCGTCA GCGGGGTCTG GTGTGGGAGG    13980

ACGATGACTC GGCAGACGAC AGCAGCGTCC TGGATTTGGG AGGGAGTGGC AACCCGTTTG    14040

CGCACCTTCG CCCCAGGCTG GGGAGAATGT TTTAAAAAAA AAAAAGCATG ATGCAAAATA    14100

AAAAACTCAC CAAGGCCATG GCACCGAGCG TTGGTTTTCT TGTATTCCCC TTAGTATGCG    14160

GCGCGCGGCG ATGTATGAGG AAGGTCCTCC TCCCTCCTAC GAGAGTGTGG TGAGCGCGGC    14220

GCCAGTGGCG GCGGCGCTGG GTTCTCCCTT CGATGCTCCC CTGGACCCGC CGTTTGTGCC    14280

TCCGCGGTAC CTGCGGCCTA CCGGGGGGAG AAACAGCATC CGTTACTCTG AGTTGGCACC    14340

CCTATTCGAC ACCACCCGTG TGTACCTGGT GGACAACAAG TCAACGGATG TGGCATCCCT    14400

GAACTACCAG AACGACCACA GCAACTTTCT GACCACGGTC ATTCAAAACA ATGACTACAG    14460

CCCGGGGGAG GCAAGCACAC AGACCATCAA TCTTGACGAC CGGTCGCACT GGGGCGGCGA    14520

CCTGAAAACC ATCCTGCATA CCAACATGCC AAATGTGAAC GAGTTCATGT TTACCAATAA    14580

GTTTAAGGCG CGGGTGATGG TGTCGCGCTT GCCTACTAAG GACAATCAGG TGGAGCTGAA    14640

ATACGAGTGG GTGGAGTTCA CGCTGCCCGA GGGCAACTAC TCCGAGACCA TGACCATAGA    14700

CCTTATGAAC AACGCGATCG TGGAGCACTA CTTGAAAGTG GGCAGACAGA ACGGGGTTCT    14760

GGAAAGCGAC ATCGGGGTAA AGTTTGACAC CCGCAACTTC AGACTGGGGT TTGACCCCGT    14820

CACTGGTCTT GTCATGCCTG GGGTATATAC AAACGAAGCC TTCCATCCAG ACATCATTTT    14880

GCTGCCAGGA TGCGGGGTGG ACTTCACCCA CAGCCGCCTG AGCAACTTGT TGGGCATCCG    14940

CAAGCGGCAA CCCTTCCAGG AGGGCTTTAG GATCACCTAC GATGATCTGG AGGGTGGTAA    15000

CATTCCCGCA CTGTTGGATG TGGACGCCTA CCAGGCGAGC TTGAAAGATG ACACCGAACA    15060

GGGCGGGGGT GGCGCAGGCG GCAGCAACAG CAGTGGCAGC GGCGCGGAAG AGAACTCCAA    15120

CGCGGCAGCC GCGGCAATGC AGCCGGTGGA GGACATGAAC GATCATGCCA TTCGCGGCGA    15180

CACCTTTGCC ACACGGGCTG AGGAGAAGCG CGCTGAGGCC GAAGCAGCGG CCGAAGCTGC    15240

CGCCCCCGCT GCGCAACCCG AGGTCGAGAA GCCTCAGAAG AAACCGGTGA TCAAACCCCT    15300

GACAGAGGAC AGCAAGAAAC GCAGTTACAA CCTAATAAGC AATGACAGCA CCTTCACCCA    15360

GTACCGCAGC TGGTACCTTG CATACAACTA CGGCGACCCT CAGACCGGAA TCCGCTCATG    15420

GACCCTGCTT TGCACTCCTG ACGTAACCTG CGGCTCGGAG CAGGTCTACT GGTCGTTGCC    15480

AGACATGATG CAAGACCCCG TGACCTTCCG CTCCACGCGC CAGATCAGCA ACTTTCCGGT    15540

GGTGGGCGCC GAGCTGTTGC CCGTGCACTC CAAGAGCTTC TACAACGACC AGGCCGTCTA    15600

CTCCCAACTC ATCCGCCAGT TTACCTCTCT GACCCACGTG TTCAATCGCT TCCCCGAGAA    15660

CCAGATTTTG GCGCGCCCGC CAGCCCCCAC CATCACCACC GTCAGTGAAA ACGTTCCTGC    15720

TCTCACAGAT CACGGGACGC TACCGCTGCG CAACAGCATC GGAGGAGTCC AGCGAGTGAC    15780
```

-continued

```
CATTACTGAC GCCAGACGCC GCACCTGCCC CTACGTTTAC AAGGCCCTGG GCATAGTCTC  15840
GCCGCGCGTC CTATCGAGCC GCACTTTTTG AGCAAGCATG TCCATCCTTA TATCGCCCAG  15900
CAATAACACA GGCTGGGGCC TGCGCTTCCC AAGCAAGATG TTTGGCGGGG CCAAGAAGCG  15960
CTCCGACCAA CACCCAGTGC GCGTGCGCGG GCACTACCGC GCGCCCTGGG GCGCGCACAA  16020
ACGCGGCCGC ACTGGGCGCA CCACCGTCGA TGACGCCATC GACGCGGTGG TGGAGGAGGC  16080
GCGCAACTAC ACGCCCACGC CGCCACCAGT GTCCACAGTG GACGCGGCCA TTCAGACCGT  16140
GGTGCGCGGA GCCCGGCGCT ATGCTAAAAT GAAGAGACGG CGGAGGCGCG TAGCACGTCG  16200
CCACCGCCGC CGACCCGGCA CTGCCGCCCA ACGCGCGGCG GCGGCCCTGC TTAACCGCGC  16260
ACGTCGCACC GGCCGACGGG CGGCCATGCG GGCCGCTCGA AGGCTGGCCG CGGGTATTGT  16320
CACTGTGCCC CCCAGGTCCA GGCGACGAGC GGCCGCCGCA GCAGCCGCGG CCATTAGTGC  16380
TATGACTCAG GGTCGCAGGG GCAACGTGTA TTGGGTGCGC GACTCGGTTA GCGGCCTGCG  16440
CGTGCCCGTG CGCACCCGCC CCCCGCGCAA CTAGATTGCA AGAAAAAACT ACTTAGACTC  16500
GTACTGTTGT ATGTATCCAG CGGCGGCGGC GCGCAACGAA GCTATGTCCA AGCGCAAAAT  16560
CAAAGAAGAG ATGCTCCAGG TCATCGCGCC GGAGATCTAT GGCCCCCCGA AGAAGGAAGA  16620
GCAGGATTAC AAGCCCCGAA AGCTAAAGCG GGTCAAAAAG AAAAAGAAAG ATGATGATGA  16680
TGAACTTGAC GACGAGGTGG AACTGCTGCA CGCTACCGCG CCCAGGCGAC GGGTACAGTG  16740
GAAAGGTCGA CGCGTAAAAC GTGTTTTGCG ACCCGGCACC ACCGTAGTCT TTACGCCCGG  16800
TGAGCGCTCC ACCCGCACCT ACAAGCGCGT GTATGATGAG GTGTACGGCG ACGAGGACCT  16860
GCTTGAGCAG GCCAACGAGC GCCTCGGGGA GTTTGCCTAC GGAAAGCGGC ATAAGGACAT  16920
GCTGGCGTTG CCGCTGGACG AGGGCAACCC AACACCTAGC CTAAAGCCCG TAACACTGCA  16980
GCAGGTGCTG CCCGCGCTTG CACCGTCCGA AGAAAAGCGC GGCCTAAAGC GCGAGTCTGG  17040
TGACTTGGCA CCCACCGTGC AGCTGATGGT ACCCAAGCGC CAGCGACTGG AAGATGTCTT  17100
GGAAAAAATG ACCGTGGAAC CTGGGCTGGA GCCCGAGGTC CGCGTGCGGC CAATCAAGCA  17160
GGTGGCGCCG GGACTGGGCG TGCAGACCGT GGACGTTCAG ATACCCACTA CCAGTAGCAC  17220
CAGTATTGCC ACCGCCACAG AGGGCATGGA GACACAAACG TCCCCGGTTG CCTCAGCGGT  17280
GGCGGATGCC GCGGTGCAGG CGGTCGCTGC GGCCGCGTCC AAGACCTCTA CGGAGGTGCA  17340
AACGGACCCG TGGATGTTTC GCGTTTCAGC CCCCCGGCGC CCGCGCGGTT CGAGGAAGTA  17400
CGGCGCCGCC AGCGCGCTAC TGCCCGAATA TGCCCTACAT CCTTCCATTG CGCCTACCCC  17460
CGGCTATCGT GGCTACACCT ACCGCCCCAG AAGACGAGCA ACTACCCGAC GCCGAACCAC  17520
CACTGGAACC CGCCGCCGCC GTCGCCGTCG CCAGCCCGTG CTGGCCCCGA TTTCCGTGCG  17580
CAGGGTGGCT CGCGAAGGAG GCAGGACCCT GGTGCTGCCA ACAGCGCGCT ACCACCCCAG  17640
CATCGTTTAA AAGCCGGTCT TTGTGGTTCT TGCAGATATG GCCCTCACCT GCCGCCTCCG  17700
TTTCCCGGTG CCGGGATTCC GAGGAAGAAT GCACCGTAGG AGGGGCATGG CCGGCCACGG  17760
CCTGACGGGC GGCATGCGTC GTGCGCACCA CCGGCGGCGG CGCGCGTCGC ACCGTCGCAT  17820
GCGCGGCGGT ATCCTGCCCC TCCTTATTCC ACTGATCGCC GCGGCGATTG GCGCCGTGCC  17880
CGGAATTGCA TCCGTGGCCT TGCAGGCGCA GAGACACTGA TTAAAAACAA GTTGCATGTG  17940
GAAAAATCAA AATAAAAAGT CTGGACTCTC ACGCTCGCTT GGTCCTGTAA CTATTTTGTA  18000
GAATGGAAGA CATCAACTTT GCGTCTCTGG CCCCGCGACA CGGCTCGCGC CGTTCATGG   18060
GAAACTGGCA AGATATCGGC ACCAGCAATA TGAGCGGTGG CGCCTTCAGC TGGGGCTCGC  18120
TGTGGAGCGG CATTAAAAAT TTCGGTTCCA CCGTTAAGAA CTATGGCAGC AAGGCCTGGA  18180
```

-continued

```
ACAGCAGCAC AGGCCAGATG CTGAGGGATA AGTTGAAAGA GCAAAATTTC AACAAAAGG   18240

TGGTAGATGG CCTGGCCTCT GGCATTAGCG GGGTGGTGGA CCTGGCCAAC CAGGCAGTGC   18300

AAAATAAGAT TAACAGTAAG CTTGATCCCC GCCCTCCCGT AGAGGAGCCT CCACCGGCCG   18360

TGGAGACAGT GTCTCCAGAG GGGCGTGGCG AAAAGCGTCC GCGCCCCGAC AGGGAAGAAA   18420

CTCTGGTGAC GCAAATAGAC GAGCCTCCCT CGTACGAGGA GGCACTAAAG CAAGGCCTGC   18480

CCACCACCCG TCCCATCGCG CCCATGGCTA CCGGAGTGCT GGGCCAGCAC ACACCCGTAA   18540

CGCTGGACCT GCCTCCCCCC GCCGACACCC AGCAGAAACC TGTGCTGCCA GGCCCGACCG   18600

CCGTTGTTGT AACCCGTCCT AGCCGCGCGT CCCTGCGCCG CGCCGCCAGC GGTCCGCGAT   18660

CGTTGCGGCC CGTAGCCAGT GGCAACTGGC AAAGCACACT GAACAGCATC GTGGGTCTGG   18720

GGGTGCAATC CCTGAAGCGC CGACGATGCT TCTGAATAGC TAACGTGTCG TATGTGTGTC   18780

ATGTATGCGT CCATGTCGCC GCCAGAGGAG CTGCTGAGCC GCCGCGCGCC CGCTTTCCAA   18840

GATGGCTACC CCTTCGATGA TGCCGCAGTG GTCTTACATG CACATCTCGG CCAGGACGC    18900

CTCGGAGTAC CTGAGCCCCG GGCTGGTGCA GTTTGCCCGC GCCACCGAGA CGTACTTCAG   18960

CCTGAATAAC AAGTTTAGAA ACCCCACGGT GGCGCCTACG CACGACGTGA CCACAGACCG   19020

GTCCCAGCGT TTGACGCTGC GGTTCATCCC TGTGGACCGT GAGGATACTG CGTACTCGTA   19080

CAAGGCGCGG TTCACCCTAG CTGTGGGTGA TAACCGTGTG CTGGACATGG CTTCCACGTA   19140

CTTTGACATC CGCGGCGTGC TGGACAGGGG CCCTACTTTT AAGCCCTACT CTGGCACTGC   19200

CTACAACGCC CTGGCTCCCA AGGGTGCCCC AAATCCTTGC GAATGGGATG AAGCTGCTAC   19260

TGCTCTTGAA ATAAACCTAG AAGAAGAGGA CGATGACAAC GAAGACGAAG TAGACGAGCA   19320

AGCTGAGCAG CAAAAAACTC ACGTATTTGG GCAGGCGCCT TATTCTGGTA TAAATATTAC   19380

AAAGGAGGGT ATTCAAATAG GTGTCGAAGG TCAAACACCT AAATATGCCG ATAAAACATT   19440

TCAACCTGAA CCTCAAATAG GAGAATCTCA GTGGTACGAA ACTGAAATTA ATCATGCAGC   19500

TGGGAGAGTC CTTAAAAAGA CTACCCCAAT GAAACCATGT TACGGTTCAT ATGCAAAACC   19560

CACAAATGAA AATGGAGGGC AAGGCATTCT TGTAAAGCAA CAAAATGGAA AGCTAGAAAG   19620

TCAAGTGGAA ATGCAATTTT TCTCAACTAC TGAGGCGACC GCAGGCAATG GTGATAACTT   19680

GACTCCTAAA GTGGTATTGT ACAGTGAAGA TGTAGATATA GAAACCCCAG ACACTCATAT   19740

TTCTTACATG CCCACTATTA AGGAAGGTAA CTCACGAGAA CTAATGGGCC AACAATCTAT   19800

GCCCAACAGG CCTAATTACA TTGCTTTTAG GGACAATTTT ATTGGTCTAA TGTATTACAA   19860

CAGCACGGGT AATATGGGTG TTCTGGCGGG CCAAGCATCG CAGTTGAATG CTGTTGTAGA   19920

TTTGCAAGAC AGAAACACAG AGCTTTCATA CCAGCTTTTG CTTGATTCCA TTGGTGATAG   19980

AACCAGGTAC TTTTCTATGT GGAATCAGGC TGTTGACAGC TATGATCCAG ATGTTAGAAT   20040

TATTGAAAAT CATGGAACTG AAGATGAACT TCCAAATTAC TGCTTTCCAC TGGGAGGTGT   20100

GATTAATACA GAGACTCTTA CCAAGGTAAA ACCTAAAACA GGTCAGGAAA ATGGATGGGA   20160

AAAAGATGCT ACAGAATTTT CAGATAAAAA TGAAATAAGA GTTGGAAATA ATTTTGCCAT   20220

GGAAATCAAT CTAAATGCCA ACCTGTGGAG AAATTTCCTG TACTCCAACA TAGCGCTGTA   20280

TTTGCCCGAC AAGCTAAAGT ACAGTCCTTC CAACGTAAAA ATTTCTGATA ACCCAAACAC   20340

CTACGACTAC ATGAACAAGC GAGTGGTGGC TCCCGGGTTA GTGGACTGCT ACATTAACCT   20400

TGGAGCACGC TGGTCCCTTG ACTATATGGA CAACGTCAAC CCATTTAACC ACCACCGCAA   20460

TGCTGGCCTG CGCTACCGCT CAATGTTGCT GGGCAATGGT CGCTATGTGC CCTTCCACAT   20520
```

```
CCAGGTGCCT CAGAAGTTCT TTGCCATTAA AAACCTCCTT CTCCTGCCGG GCTCATACAC    20580

CTACGAGTGG AACTTCAGGA AGGATGTTAA CATGGTTCTG CAGAGCTCCC TAGGAAATGA    20640

CCTAAGGGTT GACGGAGCCA GCATTAAGTT TGATAGCATT TGCCTTTACG CCACCTTCTT    20700

CCCCATGGCC CACAACACCG CCTCCACGCT TGAGGCCATG CTTAGAAACG ACACCAACGA    20760

CCAGTCCTTT AACGACTATC TCTCCGCCGC CAACATGCTC TACCCTATAC CGCCAACGC     20820

TACCAACGTG CCCATATCCA TCCCCTCCCG CAACTGGGCG GCTTTCCGCG GCTGGGCCTT    20880

CACGCGCCTT AAGACTAAGG AAACCCCATC ACTGGGCTCG GGCTACGACC CTTATTACAC    20940

CTACTCTGGC TCTATACCCT ACCTAGATGG AACCTTTTAC CTCAACCACA CCTTTAAGAA    21000

GGTGGCCATT ACCTTTGACT CTTCTGTCAG CTGGCCTGGC AATGACCGCC TGCTTACCCC    21060

CAACGAGTTT GAAATTAAGC GCTCAGTTGA CGGGGAGGGT TACAACGTTG CCCAGTGTAA    21120

CATGACCAAA GACTGGTTCC TGGTACAAAT GCTAGCTAAC TACAACATTG CTACCAGGG     21180

CTTCTATATC CCAGAGAGCT ACAAGGACCG CATGTACTCC TTCTTTAGAA ACTTCCAGCC    21240

CATGAGCCGT CAGGTGGTGG ATGATACTAA ATACAAGGAC TACCAACAGG TGGGCATCCT    21300

ACACCAACAC AACAACTCTG GATTTGTTGG CTACCTTGCC CCCACCATGC GCGAAGGACA    21360

GGCCTACCCT GCTAACTTCC CCTATCCGCT TATAGGCAAG ACCGCAGTTG ACAGCATTAC    21420

CCAGAAAAAG TTTCTTTGCG ATCGCACCCT TTGGCGCATC CCATTCTCCA GTAACTTTAT    21480

GTCCATGGGC GCACTCACAG ACCTGGGCCA AAACCTTCTC TACGCCAACT CCGCCCACGC    21540

GCTAGACATG ACTTTTGAGG TGGATCCCAT GGACGAGCCC ACCCTTCTTT ATGTTTTGTT    21600

TGAAGTCTTT GACGTGGTCC GTGTGCACCG GCCGCACCGC GGCGTCATCG AAACCGTGTA    21660

CCTGCGCACG CCCTTCTCGG CCGGCAACGC CACAACATAA AGAAGCAAGC AACATCAACA    21720

ACAGCTGCCG CCATGGGCTC CAGTGAGCAG GAACTGAAAG CCATTGTCAA AGATCTTGGT    21780

TGTGGGCCAT ATTTTTTGGG CACCTATGAC AAGCGCTTTC CAGGCTTTGT TTCTCCACAC    21840

AAGCTCGCCT GCGCCATAGT CAATACGGCC GGTCGCGAGA CTGGGGGCGT ACACTGGATG    21900

GCCTTTGCCT GGAACCCGCA CTCAAAAACA TGCTACCTCT TTGAGCCCTT TGGCTTTTCT    21960

GACCAGCGAC TCAAGCAGGT TTACCAGTTT GAGTACGAGT CACTCCTGCG CCGTAGCGCC    22020

ATTGCTTCTT CCCCCGACCG CTGTATAACG CTGGAAAAGT CCACCCAAAG CGTACAGGGG    22080

CCCAACTCGG CCGCCTGTGG ACTATTCTGC TGCATGTTTC TCCACGCCTT TGCCAACTGG    22140

CCCCAAACTC CCATGGATCA CAACCCCACC ATGAACCTTA TTACCGGGGT ACCCAACTCC    22200

ATGCTCAACA GTCCCCAGGT ACAGCCCACC CTGCGTCGCA ACCAGGAACA GCTCTACAGC    22260

TTCCTGGAGC GCCACTCGCC CTACTTCCGC AGCCACAGTG CGCAGATTAG GAGCGCCACT    22320

TCTTTTTGTC ACTTGAAAAA CATGTAAAAA TAATGTACTA GAGACACTTT CAATAAAGGC    22380

AAATGCTTTT ATTTGTACAC TCTCGGGTGA TTATTTACCC CCACCCTTGC CGTCTGCGCC    22440

GTTTAAAAAT CAAGGGGTT CTGCCGCGCA TCGCTATGCG CCACTGGCAG GGACACGTTG    22500

CGATACTGGT GTTTAGTGCT CCACTTAAAC TCAGGCACAA CCATCCGCGG CAGCTCGGTG    22560

AAGTTTTCAC TCCACAGGCT GCGCACCATC ACCAACGCGT TTAGCAGGTC GGGCGCCGAT    22620

ATCTTGAAGT CGCAGTTGGG GCCTCCGCCC TGCGCGCGCG AGTTGCGATA CACAGGGTTG    22680

CAGCACTGGA ACACTATCAG CGCCGGGTGG TGCACGCTGG CCAGCACGCT CTTGTCGGAG    22740

ATCAGATCCG CGTCCAGGTC CTCCGCGTTG CTCAGGGCGA ACGGAGTCAA CTTTGGTAGC    22800

TGCCTTCCCA AAAAGGGCGC GTGCCCAGGC TTTGAGTTGC ACTCGCACCG TAGTGGCATC    22860

AAAAGGTGAC CGTGCCCGGT CTGGGCGTTA GGATACAGCG CCTGCATAAA AGCCTTGATC    22920
```

-continued

```
TGCTTAAAAG CCACCTGAGC CTTTGCGCCT TCAGAGAAGA ACATGCCGCA AGACTTGCCG    22980

GAAAACTGAT TGGCCGGACA GGCCGCGTCG TGCACGCAGC ACCTTGCGTC GGTGTTGGAG    23040

ATCTGCACCA CATTTCGGCC CCACCGGTTC TTCACGATCT TGGCCTTGCT AGACTGCTCC    23100

TTCAGCGCGC GCTGCCCGTT TTCGCTCGTC ACATCCATTT CAATCACGTG CTCCTTATTT    23160

ATCATAATGC TTCCGTGTAG ACACTTAAGC TCGCCTTCGA TCTCAGCGCA GCGGTGCAGC    23220

CACAACGCGC AGCCCGTGGG CTCGTGATGC TTGTAGGTCA CCTCTGCAAA CGACTGCAGG    23280

TACGCCTGCA GGAATCGCCC CATCATCGTC ACAAAGGTCT TGTTGCTGGT GAAGGTCAGC    23340

TGCAACCCGC GGTGCTCCTC GTTCAGCCAG GTCTTGCATA CGGCCGCCAG AGCTTCCACT    23400

TGGTCAGGCA GTAGTTTGAA GTTCGCCTTT AGATCGTTAT CCACGTGGTA CTTGTCCATC    23460

AGCGCGCGCG CAGCCTCCAT GCCCTTCTCC CACGCAGACA CGATCGGCAC ACTCAGCGGG    23520

TTCATCACCG TAATTTCACT TTCCGCTTCG CTGGGCTCTT CCTCTTCCTC TTGCGTCCGC    23580

ATACCACGCG CCACTGGGTC GTCTTCATTC AGCCGCCGCA CTGTGCGCTT ACCTCCTTTG    23640

CCATGCTTGA TTAGCACCGG TGGGTTGCTG AAACCCACCA TTTGTAGCGC CACATCTTCT    23700

CTTTCTTCCT CGCTGTCCAC GATTACCTCT GGTGATGGCG GGCGCTCGGG CTTGGGAGAA    23760

GGGCGCTTCT TTTTCTTCTT GGGCGCAATG GCCAAATCCG CCGCCGAGGT CGATGGCCGC    23820

GGGCTGGGTG TGCGCGGCAC CAGCGCGTCT TGTGATGAGT CTTCCTCGTC CTCGGACTCG    23880

ATACGCCGCC TCATCCGCTT TTTTGGGGGC GCCCGGGGAG GCGGCGGCGA CGGGGACGGG    23940

GACGACACGT CCTCCATGGT TGGGGACGT CGCGCCGCAC CGCGTCCGCG CTCGGGGTG     24000

GTTTCGCGCT GCTCCTCTTC CCGACTGGCC ATTTCCTTCT CCTATAGGCA GAAAAAGATC    24060

ATGGAGTCAG TCGAGAAGAA GGACAGCCTA ACCGCCCCCT CTGAGTTCGC CACCACCGCC    24120

TCCACCGATG CCGCCAACGC GCCTACCACC TTCCCCGTCG AGGCACCCCC GCTTGAGGAG    24180

GAGGAAGTGA TTATCGAGCA GGACCCAGGT TTTGTAAGCG AAGACGACGA GGACCGCTCA    24240

GTACCAACAG AGGATAAAAA GCAAGACCAG GACAACGCAG AGGCAAACGA GGAACAAGTC    24300

GGGCGGGGGG ACGAAAGGCA TGGCGACTAC CTAGATGTGG GAGACGACGT GCTGTTGAAG    24360

CATCTGCAGC GCCAGTGCGC CATTATCTGC GACGCGTTGC AAGAGCGCAG CGATGTGCCC    24420

CTCGCCATAG CGGATGTCAG CCTTGCCTAC GAACGCCACC TATTCTCACC GCGCGTACCC    24480

CCCAAACGCC AAGAAAACGG CACATGCGAG CCCAACCCGC GCCTCAACTT CTACCCCGTA    24540

TTTGCCGTGC CAGAGGTGCT TGCCACCTAT CACATCTTTT TCCAAAACTG CAAGATACCC    24600

CTATCCTGCC GTGCCAACCG CAGCCGAGCG GACAAGCAGC TGGCCTTGCG GCAGGGCGCT    24660

GTCATACCTG ATATCGCCTC GCTCAACGAA GTGCCAAAAA TCTTTGAGGG TCTTGGACGC    24720

GACGAGAAGC GCGCGGCAAA CGCTCTGCAA CAGGAAAACA GCGAAAATGA AAGTCACTCT    24780

GGAGTGTTGG TGGAACTCGA GGGTGACAAC GCGCGCCTAG CCGTACTAAA ACGCAGCATC    24840

GAGGTCACCC ACTTTGCCTA CCCGGCACTT AACCTACCCC CCAAGGTCAT GAGCACAGTC    24900

ATGAGTGAGC TGATCGTGCG CCGTGCGCAG CCCCTGGAGA GGGATGCAAA TTTGCAAGAA    24960

CAAACAGAGG AGGGCCTACC CGCAGTTGGC GACGAGCAGC TAGCGCGCTG GCTTCAAACG    25020

CGCGAGCCTG CCGACTTGGA GGAGCGACGC AAACTAATGA TGGCCGCAGT GCTCGTTACC    25080

GTGGAGCTTG AGTGCATGCA GCGGTTCTTT GCTGACCCGG AGATGCAGCG CAAGCTAGAG    25140

GAAACATTGC ACTACACCTT TCGACAGGGC TACGTACGCC AGGCCTGCAA GATCTCCAAC    25200

GTGGAGCTCT GCAACCTGGT CTCCTACCTT GGAATTTTGC ACGAAAACCG CCTTGGGCAA    25260
```

-continued

```
AACGTGCTTC ATTCCACGCT CAAGGGCGAG GCGCGCCGCG ACTACGTCCG CGACTGCGTT   25320

TACTTATTTC TATGCTACAC CTGGCAGACG GCCATGGGCG TTTGGCAGCA GTGCTTGGAG   25380

GAGTGCAACC TCAAGGAGCT GCAGAAACTG CTAAAGCAAA ACTTGAAGGA CCTATGGACG   25440

GCCTTCAACG AGCGCTCCGT GGCCGCGCAC CTGGCGGACA TCATTTTCCC CGAACGCCTG   25500

CTTAAAACCC TGCAACAGGG TCTGCCAGAC TTCACCAGTC AAAGCATGTT GCAGAACTTT   25560

AGGAACTTTA TCCTAGAGCG CTCAGGAATC TTGCCCGCCA CCTGCTGTGC ACTTCCTAGC   25620

GACTTTGTGC CCATTAAGTA CCGCGAATGC CCTCCGCCGC TTTGGGGCCA CTGCTACCTT   25680

CTGCAGCTAG CCAACTACCT TGCCTACCAC TCTGACATAA TGGAAGACGT GAGCGGTGAC   25740

GGTCTACTGG AGTGTCACTG TCGCTGCAAC CTATGCACCC CGCACCGCTC CCTGGTTTGC   25800

AATTCGCAGC TGCTTAACGA AAGTCAAATT ATCGGTACCT TTGAGCTGCA GGGTCCCTCG   25860

CCTGACGAAA AGTCCGCGGC TCCGGGGTTG AAACTCACTC CGGGGCTGTG GACGTCGGCT   25920

TACCTTCGCA AATTTGTACC TGAGGACTAC CACGCCCACG AGATTAGGTT CTACGAAGAC   25980

CAATCCCGCC CGCCAAATGC GGAGCTTACC GCCTGCGTCA TTACCCAGGG CCACATTCTT   26040

GGCCAATTGC AAGCCATCAA CAAAGCCCGC CAAGAGTTTC TGCTACGAAA GGGACGGGGG   26100

GTTTACTTGG ACCCCCAGTC CGGCGAGGAG CTCAACCCAA TCCCCCCGCC GCCGCAGCCC   26160

TATCAGCAGC AGCCGCGGGC CCTTGCTTCC CAGGATGGCA CCCAAAAAGA AGCTGCAGCT   26220

GCCGCCGCCA CCCACGGACG AGGAGGAATA CTGGGACAGT CAGGCAGAGG AGGTTTTGGA   26280

CGAGGAGGAG GAGGACATGA TGGAAGACTG GGAGAGCCTA GACGAGGAAG CTTCCGAGGT   26340

CGAAGAGGTG TCAGACGAAA CACCGTCACC CTCGGTCGCA TTCCCCTCGC GGCGCCCCA    26400

GAAATCGGCA ACCGGTTCCA GCATGGCTAC AACCTCCGCT CCTCAGGCGC CGCCGGCACT   26460

GCCCGTTCGC CGACCCAACC GTAGATGGGA CACCACTGGA ACCAGGGCCG GTAAGTCCAA   26520

GCAGCCGCCG CCGTTAGCCC AAGAGCAACA ACAGCGCCAA GGCTACCGCT CATGGCGCGG   26580

GCACAAGAAC GCCATAGTTG CTTGCTTGCA AGACTGTGGG GGCAACATCT CCTTCGCCCG   26640

CCGCTTTCTT CTCTACCATC ACGGCGTGGC CTTCCCCCGT AACATCCTGC ATTACTACCG   26700

TCATCTCTAC AGCCCATACT GCACCGGCGG CAGCGGCAGC GGCAGCAACA GCAGCGGCCA   26760

CACAGAAGCA AAGGCGACCG GATAGCAAGA CTCTGACAAA GCCCAAGAAA TCCACAGCGG   26820

CGGCAGCAGC AGGAGGAGGA GCGCTGCGTC TGGCGCCCAA CGAACCCGTA TCGACCCGCG   26880

AGCTTAGAAA CAGGATTTTT CCCACTCTGT ATGCTATATT TCAACAGAGC AGGGGCCAAG   26940

AACAAGAGCT GAAAATAAAA AACAGGTCTC TGCGATCCCT CACCCGCAGC TGCCTGTATC   27000

ACAAAAGCGA AGATCAGCTT CGGCGCACGC TGGAAGACGC GGAGGCTCTC TTCAGTAAAT   27060

ACTGCGCGCT GACTCTTAAG GACTAGTTTC GCGCCCTTTC TCAAATTTAA GCGCGAAAAC   27120

TACGTCATCT CCAGCGGCCA CACCCGGCGC CAGCACCTGT CGTCAGCGCC ATTATGAGCA   27180

AGGAAATTCC CACGCCCTAC ATGTGGAGTT ACCAGCCACA AATGGGACTT GCGGCTGGAG   27240

CTGCCCAAGA CTACTCAACC CGAATAAACT ACATGAGCGC GGGACCCCAC ATGATATCCC   27300

GGGTCAACGG AATCCGCGCC CACCGAAACC GAATTCTCTT GGAACAGGCG GCTATTACCA   27360

CCACACCTCG TAATAACCTT AATCCCCGTA GTTGGCCCGC TGCCCTGGTG TACCAGGAAA   27420

GTCCCGCTCC CACCACTGTG GTACTTCCCA GAGACGCCCA GGCCGAAGTT CAGATGACTA   27480

ACTCAGGGGC GCAGCTTGCG GGCGGCTTTC GTCACAGGGT GCGGTCGCCC GGCAGGGTA    27540

TAACTCACCT GACAATCAGA GGGCGAGGTA TTCAGCTCAA CGACGAGTCG GTGAGCTCCT   27600

CGCTTGGTCT CCGTCCGGAC GGGACATTTC AGATCGGCGG CGCCGGCCGT CCTTCATTCA   27660
```

```
CGCCTCGTCA GGCAATCCTA ACTCTGCAGA CCTCGTCCTC TGAGCCGCGC TCTGGAGGCA    27720

TTGGAACTCT GCAATTTATT GAGGAGTTTG TGCCATCGGT CTACTTTAAC CCCTTCTCGG    27780

GACCTCCCGG CCACTATCCG GATCAATTTA TTCCTAACTT TGACGCGGTA AAGGACTCGG    27840

CGGACGGCTA CGACTGAATG TTAAGTGGAG AGGCAGAGCA ACTGCGCCTG AAACACCTGG    27900

TCCACTGTCG CCGCCACAAG TGCTTTGCCC GCGACTCCGG TGAGTTTTGC TACTTTGAAT    27960

TGCCCGAGGA TCATATCGAG GGCCCGGCGC ACGGCGTCCG GCTTACCGCC CAGGGAGAGC    28020

TTGCCCGTAG CCTGATTCGG GAGTTTACCC AGCGCCCCCT GCTAGTTGAG CGGGACAGGG    28080

GACCCTGTGT TCTCACTGTG ATTTGCAACT GTCCTAACCT TGGATTACAT CAAGATCTTT    28140

GTTGCCATCT CTGTGCTGAG TATAATAAAT ACAGAAATTA AAATATACTG GGGCTCCTAT    28200

CGCCATCCTG TAAACGCCAC CGTCTTCACC CGCCCAAGCA AACCAAGGCG AACCTTACCT    28260

GGTACTTTTA ACATCTCTCC CTCTGTGATT TACAACAGTT TCAACCCAGA CGGAGTGAGT    28320

CTACGAGAGA ACCTCTCCGA GCTCAGCTAC TCCATCAGAA AAAACACCAC CCTCCTTACC    28380

TGCCGGGAAC GTACGAGTGC GTCACCGGCC GCTGCACCAC ACCTACCGCC TGACCGTAAA    28440

CCAGACTTTT TCCGGACAGA CCTCAATAAC TCTGTTTACC AGAACAGGAG GTGAGCTTAG    28500

AAAACCCTTA GGGTATTAGG CCAAAGGCGC AGCTACTGTG GGGTTTATGA ACAATTCAAG    28560

CAACTCTACG GGCTATTCTA ATTCAGGTTT CTCTAGAATC GGGGTTGGGG TTATTCTCTG    28620

TCTTGTGATT CTCTTTATTC TTATACTAAC GCTTCTCTGC CTAAGGCTCG CCGCCTGCTG    28680

TGTGCACATT TGCATTTATT GTCAGCTTTT TAAACGCTGG GGTCGCCACC CAAGATGATT    28740

AGGTACATAA TCCTAGGTTT ACTCACCCTT GCGTCAGCCC ACGGTACCAC CCAAAAGGTG    28800

GATTTTAAGG AGCCAGCCTG TAATGTTACA TTCGCAGCTG AAGCTAATGA GTGCACCACT    28860

CTTATAAAAT GCACCACAGA ACATGAAAAG CTGCTTATTC GCCACAAAAA CAAAATTGGC    28920

AAGTATGCTG TTTATGCTAT TTGGCAGCCA GGTGACACTA CAGAGTATAA TGTTACAGTT    28980

TTCCAGGGTA AAAGTCATAA AACTTTTATG TATACTTTTC CATTTTATGA AATGTGCGAC    29040

ATTACCATGT ACATGAGCAA ACAGTATAAG TTGTGGCCCC CACAAAATTG TGTGGAAAAC    29100

ACTGGCACTT TCTGCTGCAC TGCTATGCTA ATTACAGTGC TCGCTTTGGT CTGTACCCTA    29160

CTCTATATTA AATACAAAAG CAGACGCAGC TTTATTGAGG AAAAGAAAAT GCCTTAATTT    29220

ACTAAGTTAC AAAGCTAATG TCACCACTAA CTGCTTTACT CGCTGCTTGC AAAACAAATT    29280

CAAAAAGTTA GCATTATAAT TAGAATAGGA TTTAAACCCC CCGGTCATTT CCTGCTCAAT    29340

ACCATTCCCC TGAACAATTG ACTCTATGTG GGATATGCTC CAGCGCTACA ACCTTGAAGT    29400

CAGGCTTCCT GGATGTCAGC ATCTGACTTT GGCCAGCACC TGTCCCGCGG ATTTGTTCCA    29460

GTCCAACTAC AGCGACCCAC CCTAACAGAG ATGACCAACA CAACCAACGC GGCCGCCGCT    29520

ACCGGACTTA CATCTACCAC AAATACACCC CAAGTTTCTG CCTTTGTCAA TAACTGGGAT    29580

AACTTGGGCA TGTGGTGGTT CTCCATAGCG CTTATGTTTG TATGCCTTAT TATTATGTGG    29640

CTCATCTGCT GCCTAAAGCG CAAACGCGCC CGACCACCCA TCTATAGTCC CATCATTGTG    29700

CTACACCCAA ACAATGATGG AATCCATAGA TTGGACGGAC TGAAACACAT GTTCTTTTCT    29760

CTTACAGTAT GATTAAATGA GACATGATTC CTCGAGTTTT TATATTACTG ACCCTTGTTG    29820

CGCTTTTTTG TGCGTGCTCC ACATTGGCTG CGGTTTCTCA CATCGAAGTA GACTGCATTC    29880

CAGCCTTCAC AGTCTATTTG CTTTACGGAT TTGTCACCCT CACGCTCATC TGCAGCCTCA    29940

TCACTGTGGT CATCGCCTTT ATCCAGTGCA TTGACTGGGT CTGTGTGCGC TTTGCATATC    30000
```

-continued

```
TCAGACACCA TCCCCAGTAC AGGGACAGGA CTATAGCTGA GCTTCTTAGA ATTCTTTAAT    30060
TATGAAATTT ACTGTGACTT TTCTGCTGAT TATTTGCACC CTATCTGCGT TTTGTTCCCC    30120
GACCTCCAAG CCTCAAAGAC ATATATCATG CAGATTCACT CGTATATGGA ATATTCCAAG    30180
TTGCTACAAT GAAAAAAGCG ATCTTTCCGA AGCCTGGTTA TATGCAATCA TCTCTGTTAT    30240
GGTGTTCTGC AGTACCATCT TAGCCCTAGC TATATATCCC TACCTTGACA TTGGCTGGAA    30300
ACGAATAGAT GCCATGAACC ACCCAACTTT CCCCGCGCCC GCTATGCTTC CACTGCAACA    30360
AGTTGTTGCC GGCGGCTTTG TCCCAGCCAA TCAGCCTCGC CCCACTTCTC CCACCCCCAC    30420
TGAAATCAGC TACTTTAATC TAACAGGAGG AGATGACTGA CACCCTAGAT CTAGAAATGG    30480
ACGGAATTAT TACAGAGCAG CGCCTGCTAG AAAGACGCAG GGCAGCGGCC GAGCAACAGC    30540
GCATGAATCA AGAGCTCCAA GACATGGTTA ACTTGCACCA GTGCAAAAGG GGTATCTTTT    30600
GTCTGGTAAA GCAGGCCAAA GTCACCTACG ACAGTAATAC CACCGGACAC CGCCTTAGCT    30660
ACAAGTTGCC AACCAAGCGT CAGAAATTGG TGGTCATGGT GGGAGAAAAG CCCATTACCA    30720
TAACTCAGCA CTCGGTAGAA ACCGAAGGCT GCATTCACTC ACCTTGTCAA GGACCTGAGG    30780
ATCTCTGCAC CCTTATTAAG ACCCTGTGCG GTCTCAAAGA TCTTATTCCC TTTAACTAAT    30840
AAAAAAAAAT AATAAAGCAT CACTTACTTA AAATCAGTTA GCAAATTTCT GTCCAGTTTA    30900
TTCAGCAGCA CCTCCTTGCC CTCCTCCCAG CTCTGGTATT GCAGCTTCCT CCTGGCTGCA    30960
AACTTTCTCC ACAATCTAAA TGGAATGTCA GTTTCCTCCT GTTCCTGTCC ATCCGCACCC    31020
ACTATCTTCA TGTTGTTGCA GATGAAGCGC GCAAGACCGT CTGAAGATAC CTTCAACCCC    31080
GTGTATCCAT ATGACACGGA AACCGGTCCT CCAACTGTGC CTTTTCTTAC TCCTCCCTTT    31140
GTATCCCCCA ATGGGTTTCA AGAGAGTCCC CCTGGGGTAC TCTCTTTGCG CCTATCCGAA    31200
CCTCTAGTTA CCTCCAATGG CATGCTTGCG CTCAAAATGG GCAACGGCCT CTCTCTGGAC    31260
GAGGCCGGCA ACCTTACCTC CCAAAATGTA ACCACTGTGA GCCCACCTCT CAAAAAAACC    31320
AAGTCAAACA TAAACCTGGA AATATCTGCA CCCCTCACAG TTACCTCAGA AGCCCTAACT    31380
GTGGCTGCCG CCGCACCTCT AATGGTCGCG GGCAACACAC TCACCATGCA ATCACAGGCC    31440
CCGCTAACCG TGCACGACTC CAAACTTAGC ATTGCCACCC AAGGACCCCT CACAGTGTCA    31500
GAAGGAAAGC TAGCCCTGCA AACATCAGGC CCCCTCACCA CCACCGATAG CAGTACCCTT    31560
ACTATCACTG CCTCACCCCC TCTAACTACT GCCACTGGTA GCTTGGGCAT TGACTTGAAA    31620
GAGCCCATTT ATACACAAAA TGGAAAACTA GGACTAAAGT ACGGGGCTCC TTTGCATGTA    31680
ACAGACGACC TAAACACTTT GACCGTAGCA ACTGGTCCAG GTGTGACTAT TAATAATACT    31740
TCCTTGCAAA CTAAAGTTAC TGGAGCCTTG GGTTTTGATT CACAAGGCAA TATGCAACTT    31800
AATGTAGCAG GAGGACTAAG GATTGATTCT CAAAACAGAC GCCTTATACT TGATGTTAGT    31860
TATCCGTTTG ATGCTCAAAA CCAACTAAAT CTAAGACTAG GACAGGGCCC TCTTTTTATA    31920
AACTCAGCCC ACAACTTGGA TATTAACTAC AACAAAGGCC TTTACTTGTT TACAGCTTCA    31980
AACAATTCCA AAAAGCTTGA GGTTAACCTA AGCACTGCCA AGGGGTTGAT GTTTGACGCT    32040
ACAGCCATAG CCATTAATGC AGGAGATGGG CTTGAATTTG GTTCACCTAA TGCACCAAAC    32100
ACAAATCCCC TCAAAACAAA AATTGGCCAT GGCCTAGAAT TTGATTCAAA CAAGGCTATG    32160
GTTCCTAAAC TAGGAACTGG CCTTAGTTTT GACAGCACAG GTGCCATTAC AGTAGGAAAC    32220
AAAAATAATG ATAAGCTAAC TTTGTGGACC ACACCAGCTC CATCTCCTAA CTGTAGACTA    32280
AATGCAGAGA AAGATGCTAA ACTCACTTTG GTCTTAACAA AATGTGGCAG TCAAATACTT    32340
GCTACAGTTT CAGTTTTGGC TGTTAAAGGC AGTTTGGCTC CAATATCTGG AACAGTTCAA    32400
```

```
AGTGCTCATC TTATTATAAG ATTTGACGAA AATGGAGTGC TACTAAACAA TTCCTTCCTG    32460

GACCCAGAAT ATTGGAACTT TAGAAATGGA GATCTTACTG AAGGCACAGC CTATACAAAC    32520

GCTGTTGGAT TTATGCCTAA CCTATCAGCT TATCCAAAAT CTCACGGTAA AACTGCCAAA    32580

AGTAACATTG TCAGTCAAGT TTACTTAAAC GGAGACAAAA CTAAACCTGT AACACTAACC    32640

ATTACACTAA ACGGTACACA GGAAACAGGA GACACAACTC CAAGTGCATA CTCTATGTCA    32700

TTTTCATGGG ACTGGTCTGG CCACAACTAC ATTAATGAAA TATTTGCCAC ATCCTCTTAC    32760

ACTTTTTCAT ACATTGCCCA AGAATAAAGA ATCGTTTGTG TTATGTTTCA ACGTGTTTAT    32820

TTTTCAATTG CAGAAAATTT CAAGTCATTT TTCATTCAGT AGTATAGCCC ACCACCACA    32880

TAGCTTATAC AGATCACCGT ACCTTAATCA AACTCACAGA ACCCTAGTAT TCAACCTGCC    32940

ACCTCCCTCC CAACACACAG AGTACACAGT CCTTTCTCCC CGGCTGGCCT TAAAAAGCAT    33000

CATATCATGG GTAACAGACA TATTCTTAGG TGTTATATTC CACACGGTTT CCTGTCGAGC    33060

CAAACGCTCA TCAGTGATAT TAATAAACTC CCCGGGCAGC TCACTTAAGT TCATGTCGCT    33120

GTCCAGCTGC TGAGCCACAG GCTGCTGTCC AACTTGCGGT TGCTTAACGG GCGGCGAAGG    33180

AGAAGTCCAC GCCTACATGG GGGTAGAGTC ATAATCGTGC ATCAGGATAG GGCGGTGGTG    33240

CTGCAGCAGC GCGCGAATAA ACTGCTGCCG CCGCCGCTCC GTCCTGCAGG AATACAACAT    33300

GGCAGTGGTC TCCTCAGCGA TGATTCGCAC CGCCCGCAGC ATAAGGCGCC TTGTCCTCCG    33360

GGCACAGCAG CGCACCCTGA TCTCACTTAA ATCAGCACAG TAACTGCAGC ACAGCACCAC    33420

AATATTGTTC AAAATCCCAC AGTGCAAGGC GCTGTATCCA AAGCTCATGG CGGGGACCAC    33480

AGAACCCACG TGGCCATCAT ACCACAAGCG CAGGTAGATT AAGTGGCGAC CCCTCATAAA    33540

CACGCTGGAC ATAAACATTA CCTCTTTTGG CATGTTGTAA TTCACCACCT CCCGGTACCA    33600

TATAAACCTC TGATTAAACA TGGCGCCATC CACCACCATC CTAAACCAGC TGGCCAAAAC    33660

CTGCCCGCCG GCTATACACT GCAGGGAACC GGGACTGGAA CAATGACAGT GGAGAGCCCA    33720

GGACTCGTAA CCATGGATCA TCATGCTCGT CATGATATCA ATGTTGGCAC AACACAGGCA    33780

CACGTGCATA CACTTCCTCA GGATTACAAG CTCCTCCCGC GTTAGAACCA TATCCCAGGG    33840

AACAACCCAT TCCTGAATCA GCGTAAATCC CACACTGCAG GGAAGACCTC GCACGTAACT    33900

CACGTTGTGC ATTGTCAAAG TGTTACATTC GGGCAGCAGC GGATGATCCT CCAGTATGGT    33960

AGCGCGGGTT TCTGTCTCAA AAGGAGGTAG ACGATCCCTA CTGTACGGAG TGCGCCGAGA    34020

CAACCGAGAT CGTGTTGGTC GTAGTGTCAT GCCAAATGGA ACGCCGGACG TAGTCATATT    34080

TCCTGAAGCA AAACCAGGTG CGGGCGTGAC AAACAGATCT GCGTCTCCGG TCTCGCCGCT    34140

TAGATCGCTC TGTGTAGTAG TTGTAGTATA TCCACTCTCT CAAAGCATCC AGGCGCCCCC    34200

TGGCTTCGGG TTCTATGTAA ACTCCTTCAT GCGCCGCTGC CCTGATAACA TCCACCACCG    34260

CAGAATAAGC CACACCCAGC CAACCTACAC ATTCGTTCTG CGAGTCACAC ACGGGAGGAG    34320

CGGGAAGAGC TGGAAGAACC ATGTTTTTTT TTTTATTCCA AAAGATTATC CAAAACCTCA    34380

AAATGAAGAT CTATTAAGTG AACGCGCTCC CCTCCGGTGG CGTGGTCAAA CTCTACAGCC    34440

AAAGAACAGA TAATGGCATT TGTAAGATGT TGCACAATGG CTTCCAAAAG GCAAACGGCC    34500

CTCACGTCCA AGTGGACGTA AAGGCTAAAC CCTTCAGGGT GAATCTCCTC TATAAACATT    34560

CCAGCACCTT CAACCATGCC CAAATAATTC TCATCTCGCC ACCTTCTCAA TATATCTCTA    34620

AGCAAATCCC GAATATTAAG TCCGGCCATT GTAAAAATCT GCTCCAGAGC GCCCTCCACC    34680

TTCAGCCTCA AGCAGCGAAT CATGATTGCA AAAATTCAGG TTCCTCACAG ACCTGTATAA    34740
```

```
GATTCAAAAG CGGAACATTA ACAAAAATAC CGCGATCCCG TAGGTCCCTT CGCAGGGCCA    34800

GCTGAACATA ATCGTGCAGG TCTGCACGGA CCAGCGCGGC CACTTCCCCG CCAGGAACCT    34860

TGACAAAAGA ACCCACACTG ATTATGCACG CATACTCGG AGCTATGCTA ACCAGCGTAG     34920

CCCCGATGTA AGCTTTGTTG CATGGGCGGC GATATAAAAT GCAAGGTGCT GCTCAAAAAA    34980

TCAGGCAAAG CCTCGCGCAA AAAGAAAGC ACATCGTAGT CATGCTCATG CAGATAAAGG     35040

CAGGTAAGCT CCGGAACCAC CACAGAAAAA GACACCATTT TTCTCTCAAA CATGTCTGCG    35100

GGTTTCTGCA TAAACACAAA ATAAAATAAC AAAAAAACAT TTAAACATTA GAAGCCTGTC    35160

TTACAACAGG AAAAACAACC CTTATAAGCA TAAGACGGAC TACGGCCATG CCGGCGTGAC    35220

CGTAAAAAAA CTGGTCACCG TGATTAAAAA GCACCACCGA CAGCTCCTCG GTCATGTCCG    35280

GAGTCATAAT GTAAGACTCG GTAAACACAT CAGGTTGATT CATCGGTCAG TGCTAAAAAG    35340

CGACCGAAAT AGCCCGGGGG AATACATACC CGCAGGCGTA GAGACAACAT TACAGCCCCC    35400

ATAGGAGGTA TAACAAAATT AATAGGAGAG AAAAACACAT AAACACCTGA AAAACCCTCC    35460

TGCCTAGGCA AAATAGCACC CTCCCGCTCC AGAACAACAT ACAGCGCTTC ACAGCGGCAG    35520

CCTAACAGTC AGCCTTACCA GTAAAAAAGA AAACCTATTA AAAAAACACC ACTCGACACG    35580

GCACCAGCTC AATCAGTCAC AGTGTAAAAA AGGGCCAAGT GCAGAGCGAG TATATATAGG    35640

ACTAAAAAAT GACGTAACGG TTAAAGTCCA CAAAAAACAC CCAGAAAACC GCACGCGAAC    35700

CTACGCCCAG AAACGAAAGC CAAAAAACCC ACAACTTCCT CAAATCGTCA CTTCCGTTTT    35760

CCCACGTTAC GTAACTTCCC ATTTTAAGAA AACTACAATT CCCAACACAT ACAAGTTACT    35820

CCGCCCTAAA ACCTACGTCA CCCGCCCCGT TCCCACGCCC CGCGCCACGT CACAAACTCC    35880

ACCCCCTCAT TATCATATTG GCTTCAATCC AAAATAAGGT ATATTATTGA TGATG         35935

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

TTCATTTTAT GTTTCAGGTT CAGGG                                              25

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

TTACCGCCAC ACTCGCAGGG                                                    20

(2) INFORMATION FOR SEQ ID NO:4:

(i) SEQUENCE CHARACTERISTICS:
        (A) LENGTH: 34303 base pairs
        (B) TYPE: nucleic acid
        (C) STRANDEDNESS: double
```

(D) TOPOLOGY: linear (ii) MOLECULE TYPE: other nucleic acid
   (A) DESCRIPTION: /desc = "DNA"

(xi) SEQUENCE DESCRIPTION: SEQ ID NO:4:

```
TTATTTTGGA TTGAAGCCAA TATGATAATG AGGGGGTGGA GTTTGTGACG TGGCGCGGGG      60

CGTGGGAACG GGGCGGGTGA CGTAGTAGTG TGGCGGAAGT GTGATGTTGC AAGTGTGGCG     120

GAACACATGT AAGCGACGGA TGTGGCAAAA GTGACGTTTT TGGTGTGCGC CGGATCCACA     180

GGACGGGTGT GGTCGCCATG ATCGCGTAGT CGATAGTGGC TCCAAGTAGC GAAGCGAGCA     240

GGACTGGGCG GCGGCCAAAG CGGTCGGACA GTGCTCCGAG AACGGGTGCG CATAGAAATT     300

GCATCAACGC ATATAGCGCT AGCAGCACGC CATAGTGACT GGCGATGCTG TCGGAATGGA     360

CGATATCCCG CAAGAGGCCC GGCAGTACCG GCATAACCAA GCCTATGCCT ACAGCATCCA     420

GGGTGACGGT GCCGAGGATG ACGATGAGCG CATTGTTAGA TTTCATACAC GGTGCCTGAC     480

TGCGTTAGCA ATTTAACTGT GATAAACTAC CGCATTAAAG CTTATCGATG ATAAGCTGTC     540

AAACATGAGA ATTCTTGAAG ACGAAAGGGC CTCGTGATAC GCCTATTTTT ATAGGTTAAT     600

GTCATGATAA TAATGGTTTC TTAGACGTCA GGTGGCACTT TTCGGGGAAA TGTGCGCGGA     660

ACCCCTATTT GTTTATTTTT CTAAATACAT TCAAATATGT ATCCGCTCAT GAGACAATAA     720

CCCTGATAAA TGCTTCAATA ATATTGAAAA AGGAAGAGTA TGAGTATTCA ACATTTCCGT     780

GTCGCCCTTA TTCCCTTTTT TGCGGCATTT TGCCTTCCTG TTTTTGCTCA CCCAGAAACG     840

CTGGTGAAAG TAAAAGATGC TGAAGATCAG TTGGGTGCAC GAGTGGGTTA CATCGAACTG     900

GATCTCAACA GCGGTAAGAT CCTTGAGAGT TTTCGCCCCG AAGAACGTTT TCCAATGATG     960

AGCACTTTTA AAGTTCTGCT ATGTGGCGCG GTATTATCCC GTGTTGACGC CGGGCAAGAG    1020

CAACTCGGTC GCCGCATACA CTATTCTCAG AATGACTTGG TTGAGTACTC ACCAGTCACA    1080

GAAAAGCATC TTACGGATGG CATGACAGTA AGAGAATTAT GCAGTGCTGC CATAACCATG    1140

AGTGATAACA CTGCGGCCAA CTTACTTCTG ACAACGATCG GAGGACCGAA GGAGCTAACC    1200

GCTTTTTTGC ACAACATGGG GGATCATGTA ACTCGCCTTG ATCGTTGGGA ACCGGAGCTG    1260

AATGAAGCCA TACCAAACGA CGAGCGTGAC ACCACGATGC CTGCAGCAAT GGCAACAACG    1320

TTGCGCAAAC TATTAACTGG CGAACTACTT ACTCTAGCTT CCCGGCAACA ATTAATAGAC    1380

TGGATGGAGG CGGATAAAGT TGCAGGACCA CTTCTGCGCT CGGCCCTTCC GGCTGGCTGG    1440

TTTATTGCTG ATAAATCTGG AGCCGGTGAG CGTGGGTCTC GCGGTATCAT TGCAGCACTG    1500

GGGCCAGATG GTAAGCCCTC CCGTATCGTA GTTATCTACA CGACGGGGAG TCAGGCAACT    1560

ATGGATGAAC GAAATAGACA GATCGCTGAG ATAGGTGCCT CACTGATTAA GCATTGGTAA    1620

CTGTCAGACC AAGTTTACTC ATATATACTT TAGATTGATT TAAAACTTCA TTTTTAATTT    1680

AAAAGGATCT AGGTGAAGAT CCTTTTTGAT AATCTCATGA CCAAAATCCC TTAACGTGAG    1740

TTTTCGTTCC ACTGAGCGTC AGACCCCGTA GAAAAGATCA AAGGATCTTC TTGAGATCCT    1800

TTTTTTCTGC GCGTAATCTG CTGCTTGCAA ACAAAAAAAC CACCGCTACC AGCGGTGGTT    1860

TGTTTGCCGG ATCAAGAGCT ACCAACTCTT TTTCCGAAGG TAACTGGCTT CAGCAGAGCG    1920

CAGATACCAA ATACTGTCCT TCTAGTGTAG CCGTAGTTAG GCCACCACTT CAAGAACTCT    1980

GTAGCACCGC CTACATACCT CGCTCTGCTA ATCCTGTTAC CAGTGGCTGC TGCCAGTGGC    2040

GATAAGTCGT GTCTTACCGG GTTGGACTCA AGACGATAGT TACCGGATAA GGCGCAGCGG    2100

TCGGGCTGAA CGGGGGGTTC GTGCACACAG CCCAGCTTGG AGCGAACGAC CTACACCGAA    2160
```

```
CTGAGATACC TACAGCGTGA GCATTGAGAA AGCGCCACGC TTCCCGAAGG GAGAAAGGCG    2220

GACAGGTATC CGGTAAGCGG CAGGGTCGGA ACAGGAGAGC GCACGAGGGA GCTTCCAGGG    2280

GGAAACGCCT GGTATCTTTA TAGTCCTGTC GGGTTTCGCC ACCTCTGACT TGAGCGTCGA    2340

TTTTTGTGAT GCTCGTCAGG GGGGCGGAGC CTATGGAAAA ACGCCAGCAA CGCGGCCTTT    2400

TTACGGTTCC TGGCCTTTTG CTGGCCTTTT GCTCACATGT TCTTTCCTGC GTTATCCCCT    2460

GATTCTGTGG ATAACCGTAT TACCGCCTTT GAGTGAGCTG ATACCGCTCG CCGCAGCCGA    2520

ACGACCGAGC GCAGCGAGTC AGTGAGCGAG GAAGCGGAAG AGCGCCTGAT GCGGTATTTT    2580

CTCCTTACGC ATCTGTGCGG TATTTCACAC CGCATATGGT GCACTCTCAG TACAATCTGC    2640

TCTGATGCCG CATAGTTAAG CCAGTATACA CTCCGCTATC GCTACGTGAC TGGGTCATGG    2700

CTGCGCCCCG ACACCCGCCA ACACCCGCTG ACGCGCCCTG ACGGGCTTGT CTGCTCCCGG    2760

CATCCGCTTA CAGACAAGCT GTGACCGTCT CCGGGAGCTG CATGTGTCAG AGGTTTTCAC    2820

CGTCATCACC GAAACGCGCG AGGCAGTCTA GACAATAGTA GTACGGATAG CTGTGACTCC    2880

GGTCCTTCTA ACACACCTCC TGAGATACAC CCGGTGGTCC CGCTGTGCCC CATTAAACCA    2940

GTTGCCGTGA GAGTTGGTGG GCGTCGCCAG GCTGTGGAAT GTATCGAGGA CTTGCTTAAC    3000

GAGCCTGGGC AACCTTTGGA CTTGAGCTGT AAACGCCCCA GGCCATAAGG TGTAAACCTG    3060

TGATTGCGTG TGTGGTTAAC GCCTTTGTTT GCTGAATGAG TTGATGTAAG TTTAATAAAG    3120

GGTGAGATAA TGTTTAACTT GCATGGCGTG TTAAATGGGG CGGGGCTTAA AGGGTATATA    3180

ATGCGCCGTG GGCTAATCTT GGTTACATCT GACCTCATGG AGGCTTGGGA GTGTTTGGAA    3240

GATTTTCTG CTGTGCGTAA CTTGCTGGAA CAGAGCTCTA ACAGTACCTC TTGGTTTTGG    3300

AGGTTTCTGT GGGGCTCATC CCAGGCAAAG TTAGTCTGCA GAATTAAGGA GGATTACAAG    3360

TGGGAATTTG AAGAGCTTTT GAAATCCTGT GGTGAGCTGT TTGATTCTTT GAATCTGGGT    3420

CACCAGGCGC TTTTCCAAGA GAAGGTCATC AAGACTTTGG ATTTTTCCAC ACCGGGGCGC    3480

GCTGCGGCTG CTGTTGCTTT TTTGAGTTTT ATAAAGGATA AATGGAGCGA AGAAACCCAT    3540

CTGAGCGGGG GGTACCTGCT GGATTTTCTG GCCATGCATC TGTGGAGAGC GGTTGTGAGA    3600

CACAAGAATC GCCTGCTACT GTTGTCTTCC GTCCGCCCGG CGATAATACC GACGGAGGAG    3660

CAGCAGCAGC AGCAGGAGGA AGCCAGGCGG CGGCGGCAGG AGCAGAGCCC ATGGAACCCG    3720

AGAGCCGGCC TGGACCCTCG GGAATGAATG TTGTACAGGT GGCTGAACTG TATCCAGAAC    3780

TGAGACGCAT TTTGACAATT ACAGAGGATG GGCAGGGGCT AAAGGGGGTA AAGAGGGAGC    3840

GGGGGGCTTG TGAGGCTACA GAGGAGGCTA GGAATCTAGC TTTTAGCTTA ATGACCAGAC    3900

ACCGTCCTGA GTGTATTACT TTTCAACAGA TCAAGGATAA TTGCGCTAAT GAGCTTGATC    3960

TGCTGGCGCA GAAGTATTCC ATAGAGCAGC TGACCACTTA CTGGCTGCAG CCAGGGGATG    4020

ATTTTGAGGA GGCTATTAGG GTATATGCAA AGGTGGCACT TAGGCCAGAT TGCAAGTACA    4080

AGATCAGCAA ACTTGTAAAT ATCAGGAATT GTTGCTACAT TTCTGGGAAC GGGGCCGAGG    4140

TGGAGATAGA TACGGAGGAT AGGGTGGCCT TTAGATGTAG CATGATAAAT ATGTGGCCGG    4200

GGGTGCTTGG CATGGACGGG GTGGTTATTA TGAATGTAAG GTTTACTGGC CCCAATTTTA    4260

GCGGTACGGT TTTCCTGGCC AATACCAACC TTATCCTACA CGGTGTAAGC TTCTATGGGT    4320

TTAACAATAC CTGTGTGGAA GCCTGGACCG ATGTAAGGGT TCGGGCTGT GCCTTTTACT    4380

GCTGCTGGAA GGGGTGGTG TGTCGCCCCA AAAGCAGGGC TTCAATTAAG AAATGCCTCT    4440

TTGAAAGGTG TACCTTGGGT ATCCTGTCTG AGGGTAACTC CAGGGTGCGC CACAATGTGG    4500

CCTCCGACTG TGGTTGCTTC ATGCTAGTGA AAAGCGTGGC TGTGATTAAG CATAACATGG    4560
```

```
TATGTGGCAA CTGCGAGGAC AGGGCCTCTC AGATGCTGAC CTGCTCGGAC GGCAACTGTC    4620

ACCTGCTGAA GACCATTCAC GTAGCCAGCC ACTCTCGCAA GGCCTGGCCA GTGTTTGAGC    4680

ATAACATACT GACCCGCTGT TCCTTGCATT TGGGTAACAG GAGGGGGGTG TTCCTACCTT    4740

ACCAATGCAA TTTGAGTCAC ACTAAGATAT TGCTTGAGCC CGAGAGCATG TCCAAGGTGA    4800

ACCTGAACGG GGTGTTTGAC ATGACCATGA AGATCTGGAA GGTGCTGAGG TACGATGAGA    4860

CCCGCACCAG GTGCAGACCC TGCGAGTGTG GCGGTAAACA TATTAGGAAC AGCCTGTGA    4920

TGCTGGATGT GACCGAGGAG CTGAGGCCCG ATCACTTGGT GCTGGCCTGC ACCCGCGCTG    4980

AGTTTGGCTC TAGCGATGAA GATACAGATT GAGGTACTGA AATGTGTGGG CGTGGCTTAA    5040

GGGTGGGAAA GAATATATAA GGTGGGGGTC TTATGTAGTT TTGTATCTGT TTTGCAGCAG    5100

CCGCCGCCGC CATGAGCACC AACTCGTTTG ATGGAAGCAT TGTGAGCTCA TATTTGACAA    5160

CGCGCATGCC CCCATGGGCC GGGGTGCGTC AGAATGTGAT GGGCTCCAGC ATTGATGGTC    5220

GCCCCGTCCT GCCCGCAAAC TCTACTACCT TGACCTACGA GACCGTGTCT GGAACGCCGT    5280

TGGAGACTGC AGCCTCCGCC GCCGCTTCAG CCGCTGCAGC CACCGCCCGC GGGATTGTGA    5340

CTGACTTTGC TTTCCTGAGC CCGCTTGCAA GCAGTGCAGC TTCCCGTTCA TCCGCCCGCG    5400

ATGACAAGTT GACGGCTCTT TTGGCACAAT TGGATTCTTT GACCCGGGAA CTTAATGTCG    5460

TTTCTCAGCA GCTGTTGGAT CTGCGCCAGC AGGTTTCTGC CCTGAAGGCT TCCTCCCCTC    5520

CCAATGCGGT TTAAAACATA AATAAAAAAC CAGACTCTGT TTGGATTTGG ATCAAGCAAG    5580

TGTCTTGCTG TCTTTATTTA GGGGTTTTGC GCGCGCGGTA GGCCCGGGAC CAGCGGTCTC    5640

GGTCGTTGAG GGTCCTGTGT ATTTTTTCCA GGACGTGGTA AAGGTGACTC TGGATGTTCA    5700

GATACATGGG CATAAGCCCG TCTCTGGGGT GGAGGTAGCA CCACTGCAGA GCTTCATGCT    5760

GCGGGGTGGT GTTGTAGATG ATCCAGTCGT AGCAGGAGCG CTGGGCGTGG TGCCTAAAAA    5820

TGTCTTTCAG TAGCAAGCTG ATTGCCAGGG GCAGGCCCTT GGTGTAAGTG TTTACAAAGC    5880

GGTTAAGCTG GGATGGGTGC ATACGTGGGG ATATGAGATG CATCTTGGAC TGTATTTTTA    5940

GGTTGGCTAT GTTCCCAGCC ATATCCCTCC GGGGATTCAT GTTGTGCAGA ACCACCAGCA    6000

CAGTGTATCC GGTGCACTTG GGAAATTTGT CATGTAGCTT AGAAGGAAAT GCGTGGAAGA    6060

ACTTGGAGAC GCCCTTGTGA CCTCCAAGAT TTTCCATGCA TTCGTCCATA ATGATGGCAA    6120

TGGGCCCACG GGCGGCGGCC TGGGCGAAGA TATTTCTGGG ATCACTAACG TCATAGTTGT    6180

GTTCCAGGAT GAGATCGTCA TAGGCCATTT TTACAAAGCG CGGGCGGAGG GTGCCAGACT    6240

GCGGTATAAT GGTTCCATCC GGCCCAGGGG CGTAGTTACC CTCACAGATT TGCATTTCCC    6300

ACGCTTTGAG TTCAGATGGG GGGATCATGT CTACCTGCGG GGCGATGAAG AAAACGGTTT    6360

CCGGGGTAGG GGAGATCAGC TGGGAAGAAA GCAGGTTCCT GAGCAGCTGC GACTTACCGC    6420

AGCCGGTGGG CCCGTAAATC ACACCTATTA CCGGGTGCAA CTGGTAGTTA AGAGAGCTGC    6480

AGCTGCCGTC ATCCCTGAGC AGGGGGGCCA CTTCGTTAAG CATGTCCCTG ACTCGCATGT    6540

TTTCCCTGAC CAAATCCGCC AGAAGGCGCT CGCCGCCCAG CGATAGCAGT TCTTGCAAGG    6600

AAGCAAAGTT TTTCAACGGT TTGAGACCGT CCGCCGTAGG CATGCTTTTG AGCGTTTGAC    6660

CAAGCAGTTC CAGGCGGTCC CACAGCTCGG TCACCTGCTC TACGGCATCT CGATCCAGCA    6720

TATCTCCTCG TTTCGCGGGT TGGGGCGGCT TTCGCTGTAC GGCAGTAGTC GGTGCTCGTC    6780

CAGACGGGCC AGGGTCATGT CTTTCCACGG GCGCAGGGTC CTCGTCAGCG TAGTCTGGGT    6840

CACGGTGAAG GGGTGCGCTC CGGGCTGCGC GCTGGCCAGG GTGCGCTTGA GGCTGGTCCT    6900
```

```
GCTGGTGCTG AAGCGCTGCC GGTCTTCGCC CTGCGCGTCG GCCAGGTAGC ATTTGACCAT    6960

GGTGTCATAG TCCAGCCCCT CCGCGGCGTG GCCCTTGGCG CGCAGCTTGC CCTTGGAGGA    7020

GGCGCCGCAC GAGGGGCAGT GCAGACTTTT GAGGGCGTAG AGCTTGGGCG CGAGAAATAC    7080

CGATTCCGGG GAGTAGGCAT CCGCGCCGCA GGCCCCGCAG ACGGTCTCGC ATTCCACGAG    7140

CCAGGTGAGC TCTGGCCGTT CGGGGTCAAA AACCAGGTTT CCCCCATGCT TTTTGATGCG    7200

TTTCTTACCT CTGGTTTCCA TGAGCCGGTG TCCACGCTCG GTGACGAAAA GGCTGTCCGT    7260

GTCCCCGTAT ACAGACTTGA GAGGCCTGTC CTCGAGCGGT GTTCCGCGGT CCTCCTCGTA    7320

TAGAAACTCG GACCACTCTG AGACAAAGGC TCGCGTCCAG GCCAGCACGA AGGAGGCTAA    7380

GTGGGAGGGG TAGCGGTCGT TGTCCACTAG GGGGTCCACT CGCTCCAGGG TGTGAAGACA    7440

CATGTCGCCC TCTTCGGCAT CAAGGAAGGT GATTGGTTTG TAGGTGTAGG CCACGTGACC    7500

GGGTGTTCCT GAAGGGGGGC TATAAAAGGG GGTGGGGGCG CGTTCGTCCT CACTCTCTTC    7560

CGCATCGCTG TCTGCGAGGG CCAGCTGTTG GGGTGAGTAC TCCCTCTGAA AAGCGGGCAT    7620

GACTTCTGCG CTAAGATTGT CAGTTTCCAA AAACGAGGAG GATTTGATAT TCACCTGGCC    7680

CGCGGTGATG CCTTTGAGGG TGGCCGCATC CATCTGGTCA GAAAAGACAA TCTTTTTGTT    7740

GTCAAGCTTG GTGGCAAACG ACCCGTAGAG GGCGTTGGAC AGCAACTTGG CGATGGAGCG    7800

CAGGGTTTGG TTTTTGTCGC GATCGGCGCG CTCCTTGGCC GCGATGTTTA GCTGCACGTA    7860

TTCGCGCGCA ACGCACCGCC ATTCGGGAAA GACGGTGGTG CGCTCGTCGG GCACCAGGTG    7920

CACGCGCCAA CCGCGGTTGT GCAGGGTGAC AAGGTCAACG CTGGTGGCTA CCTCTCCGCG    7980

TAGGCGCTCG TTGGTCCAGC AGAGGCGGCC GCCCTTGCGC GAGCAGAATG GCGGTAGGGG    8040

GTCTAGCTGC GTCTCGTCCG GGGGTCTGC GTCCACGGTA AAGACCCCGG GCAGCAGGCG    8100

CGCGTCGAAG TAGTCTATCT TGCATCCTTG CAAGTCTAGC GCCTGCTGCC ATGCGCGGGC    8160

GGCAAGCGCG CGCTCGTATG GGTTGAGTGG GGGACCCCAT GGCATGGGGT GGGTGAGCGC    8220

GGAGGCGTAC ATGCCGCAAA TGTCGTAAAC GTAGAGGGGC TCTCTGAGTA TTCCAAGATA    8280

TGTAGGGTAG CATCTTCCAC CGCGGATGCT GGCGCGCACG TAATCGTATA GTTCGTGCGA    8340

GGGAGCGAGG AGGTCGGGAC CGAGGTTGCT ACGGGCGGGC TGCTCTGCTC GGAAGACTAT    8400

CTGCCTGAAG ATGGCATGTG AGTTGGATGA TATGGTTGGA CGCTGGAAGA CGTTGAAGCT    8460

GGCGTCTGTG AGACCTACCG CGTCACGCAC GAAGGAGGCG TAGGAGTCGC GCAGCTTGTT    8520

GACCAGCTCG GCGGTGACCT GCACGTCTAG GGCGCAGTAG TCCAGGGTTT CCTTGATGAT    8580

GTCATACTTA TCCTGTCCCT TTTTTTTCCA CAGCTCGCGG TTGAGGACAA ACTCTTCGCG    8640

GTCTTTCCAG TACTCTTGGA TCGGAAACCC GTCGGCCTCC GAACGGTAAG AGCCTAGCAT    8700

GTAGAACTGG TTGACGGCCT GGTAGGCGCA GCATCCCTTT TCTACGGGTA GCGCGTATGC    8760

CTGCGCGGCC TTCCGGAGCG AGGTGTGGGT GAGCGCAAAG GTGTCCCTGA CCATGACTTT    8820

GAGGTACTGG TATTTGAAGT CAGTGTCGTC GCATCCGCCC TGCTCCCAGA GCAAAAAGTC    8880

CGTGCGCTTT TTGGAACGCG GATTTGGCAG GGCGAAGGTG ACATCGTTGA AGAGTATCTT    8940

TCCCGCGCGA GGCATAAAGT TGCGTGTGAT GCGGAAGGGT CCCGGCACCT CGGAACGGTT    9000

GTTAATTACC TGGGCGGCGA GCACGATCTC GTCAAAGCCG TTGATGTTGT GGCCCACAAT    9060

GTAAAGTTCC AAGAAGCGCG GGATGCCCTT GATGGAAGGC AATTTTTTAA GTTCCTCGTA    9120

GGTGAGCTCT TCAGGGGAGC TGAGCCCGTG CTCTGAAAGG GCCCAGTCTG CAAGATGAGG    9180

GTTGGAAGCG ACGAATGAGC TCCACAGGTC ACGGGCCATT AGCATTTGCA GGTGGTCGCG    9240

AAAGGTCCTA AACTGGCGAC CTATGGCCAT TTTTTCTGGG GTGATGCAGT AGAAGGTAAG    9300
```

-continued

```
CGGGTCTTGT TCCCAGCGGT CCCATCCAAG GTTCGCGGCT AGGTCTCGCG CGGCAGTCAC    9360

TAGAGGCTCA TCTCCGCCGA ACTTCATGAC CAGCATGAAG GGCACGAGCT GCTTCCCAAA    9420

GGCCCCCATC CAAGTATAGG TCTCTACATC GTAGGTGACA AAGAGACGCT CGGTGCGAGG    9480

ATGCGAGCCG ATCGGGAAGA ACTGGATCTC CCGCCACCAA TTGGAGGAGT GGCTATTGAT    9540

GTGGTGAAAG TAGAAGTCCC TGCGACGGGC CGAACACTCG TGCTGGCTTT TGTAAAAACG    9600

TGCGCAGTAC TGGCAGCGGT GCACGGGCTG TACATCCTGC ACGAGGTTGA CCTGACGACC    9660

GCGCACAAGG AAGCAGAGTG GGAATTTGAG CCCCTCGCCT GGCGGGTTTG GCTGGTGGTC    9720

TTCTACTTCG GCTGCTTGTC CTTGACCGTC TGGCTGCTCG AGGGGAGTTA CGGTGGATCG    9780

GACCACCACG CCGCGCGAGC CCAAAGTCCA GATGTCCGCG CGCGGCGGTC GGAGCTTGAT    9840

GACAACATCG CGCAGATGGG AGCTGTCCAT GGTCTGGAGC TCCCGCGGCG TCAGGTCAGG    9900

CGGGAGCTCC TGCAGGTTTA CCTCGCATAG ACGGGTCAGG GCGCGGGCTA GATCCAGGTG    9960

ATACCTAATT TCCAGGGGCT GGTTGGTGGC GGCGTCGATG GCTTGCAAGA GGCCGCATCC   10020

CCGCGGCGCG ACTACGGTAC CGCGCGGCGG GCGGTGGGCC GCGGGGTGT CCTTGGATGA    10080

TGCATCTAAA AGCGGTGACG CGGGCGAGCC CCCGGAGGTA GGGGGGGCTC CGGACCCGCC   10140

GGGAGAGGGG GCAGGGGCAC GTCGGCGCCG CGCGCGGGCA GGAGCTGGTG CTGCGCGCGT   10200

AGGTTGCTGG CGAACGCGAC GACGCGGCGG TTGATCTCCT GAATCTGGCG CCTCTGCGTG   10260

AAGACGACGG GCCCGGTGAG CTTGAGCCTG AAAGAGAGTT CGACAGAATC AATTTCGGTG   10320

TCGTTGACGG CGGCCTGGCG CAAAATCTCC TGCACGTCTC CTGAGTTGTC TTGATAGGCG   10380

ATCTCGGCCA TGAACTGCTC GATCTCTTCC TCCTGGAGAT CTCCGCGTCC GGCTCGCTCC   10440

ACGGTGGCGG CGAGGTCGTT GGAAATGCGG GCCATGAGCT GCGAGAAGGC GTTGAGGCCT   10500

CCCTCGTTCC AGACGCGGCT GTAGACCACG CCCCCTTCGG CATCGCGGGC GCGCATGACC   10560

ACCTGCGCGA GATTGAGCTC CACGTGCCGG GCGAAGACGG CGTAGTTTCG CAGGCGCTGA   10620

AAGAGGTAGT TGAGGGTGGT GGCGGTGTGT TCTGCCACGA AGAAGTACAT AACCCAGCGT   10680

CGCAACGTGG ATTCGTTGAT ATCCCCCAAG GCCTCAAGGC GCTCCATGGC CTCGTAGAAG   10740

TCCACGGCGA AGTTGAAAAA CTGGGAGTTG CGCGCCGACA CGGTTAACTC CTCCTCCAGA   10800

AGACGGATGA GCTCGGCGAC AGTGTCGCGC ACCTCGCGCT CAAAGGCTAC AGGGGCCTCT   10860

TCTTCTTCTT CAATCTCCTC TTCCATAAGG GCCTCCCCTT CTTCTTCTTC TGGCGGCGGT   10920

GGGGGAGGGG GGACACGGCG GCGACGACGG CGCACCGGGA GGCGGTCGAC AAAGCGCTCG   10980

ATCATCTCCC CGCGGCGACG GCGCATGGTC TCGGTGACGG CGCGGCCGTT CTCGCGGGGG   11040

CGCAGTTGGA AGACGCCGCC CGTCATGTCC CGGTTATGGG TTGGCGGGGG GCTGCCATGC   11100

GGCAGGGATA CGGCGCTAAC GATGCATCTC AACAATTGTT GTGTAGGTAC TCCGCCGCCG   11160

AGGGACCTGA GCGAGTCCGC ATCGACCGGA TCGGAAAACC TCTCGAGAAA GGCGTCTAAC   11220

CAGTCACAGT CGCAAGGTAG GCTGAGCACC GTGGCGGGCG GCAGCGGGCG GCGGTCGGGG   11280

TTGTTTCTGG CGGAGGTGCT GCTGATGATG TAATTAAAGT AGGCGGTCTT GAGACGGCGG   11340

ATGGTCGACA GAAGCACCAT GTCCTTGGGT CCGGCCTGCT GAATGCGCAG GCGGTCGGCC   11400

ATGCCCCAGG CTTCGTTTTG ACATCGGCGC AGGTCTTTGT AGTAGTCTTG CATGAGCCTT   11460

TCTACCGGCA CTTCTTCTTC TCCTTCCTCT TGTCCTGCAT CTCTTGCATC TATCGCTGCG   11520

GCGGCGGCGG AGTTTGGCCG TAGGTGGCGC CCTCTTCCTC CCATGCGTGT GACCCCGAAG   11580

CCCCTCATCG GCTGAAGCAG GGCTAGGTCG GCGACAACGC GCTCGGCTAA TATGGCCTGC   11640
```

-continued

```
TGCACCTGCG TGAGGGTAGA CTGGAAGTCA TCCATGTCCA CAAAGCGGTG GTATGCGCCC    11700

GTGTTGATGG TGTAAGTGCA GTTGGCCATA ACGGACCAGT TAACGGTCTG GTGACCCGGC    11760

TGCGAGAGCT CGGTGTACCT GAGACGCGAG TAAGCCCTCG AGTCAAATAC GTAGTCGTTG    11820

CAAGTCCGCA CCAGGTACTG GTATCCCACC AAAAAGTGCG GCGGCGGCTG GCGGTAGAGG    11880

GGCCAGCGTA GGGTGGCCGG GGCTCCGGGG GCGAGATCTT CCAACATAAG GCGATGATAT    11940

CCGTAGATGT ACCTGGACAT CCAGGTGATG CCGGCGGCGG TGGTGGAGGC GCGCGGAAAG    12000

TCGCGGACGC GGTTCCAGAT GTTGCGCAGC GGCAAAAAGT GCTCCATGGT CGGGACGCTC    12060

TGGCCGGTCA GGCGCGCGCA ATCGTTGACG CTCTACCGTG CAAAAGGAGA GCCTGTAAGC    12120

GGGCACTCTT CCGTGGTCTG GTGGATAAAT TCGCAAGGGT ATCATGGCGG ACGACCGGGG    12180

TTCGAGCCCC GTATCCGGCC GTCCGCCGTG ATCCATGCGG TTACCGCCCG CGTGTCGAAC    12240

CCAGGTGTGC GACGTCAGAC AACGGGGAG TGCTCCTTTT GGCTTCCTTC CAGGCGCGGC     12300

GGCTGCTGCG CTAGCTTTTT TGGCCACTGG CCGCGCGCAG CGTAAGCGGT TAGGCTGGAA    12360

AGCGAAAGCA TTAAGTGGCT CGCTCCCTGT AGCCGGAGGG TTATTTTCCA AGGGTTGAGT    12420

CGCGGGACCC CCGGTTCGAG TCTCGGACCG GCCGGACTGC GGCGAACGGG GGTTTGCCTC    12480

CCCGTCATGC AAGACCCCGC TTGCAAATTC CTCCGGAAAC AGGGACGAGC CCCTTTTTTG    12540

CTTTTCCCAG ATGCATCCGG TGCTGCGGCA GATGCGCCCC CCTCCTCAGC AGCGGCAAGA    12600

GCAAGAGCAG CGGCAGACAT GCAGGGCACC CTCCCCTCCT CCTACCGCGT CAGGAGGGGC    12660

GACATCCGCG GTTGACGCGG CAGCAGATGG TGATTACGAA CCCCCGCGGC GCCGGGCCCG    12720

GCACTACCTG GACTTGGAGG AGGGCGAGGG CCTGGCGCGG CTAGGAGCGC CCTCTCCTGA    12780

GCGGTACCCA AGGGTGCAGC TGAAGCGTGA TACGCGTGAG GCGTACGTGC CGCGGCAGAA    12840

CCTGTTTCGC GACCGCGAGG GAGAGGAGCC CGAGGAGATG CGGGATCGAA AGTTCCACGC    12900

AGGGCGCGAG CTGCGGCATG GCCTGAATCG CGAGCGGTTG CTGCGCGAGG AGGACTTTGA    12960

GCCCGACGCG CGAACCGGGA TTAGTCCCGC GCGCGCACAC GTGGCGGCCG CCGACCTGGT    13020

AACCGCATAC GAGCAGACGG TGAACCAGGA GATTAACTTT CAAAAAAGCT TTAACAACCA    13080

CGTGCGTACG CTTGTGGCGC GCGAGGAGGT GGCTATAGGA CTGATGCATC TGTGGGACTT    13140

TGTAAGCGCG CTGGAGCAAA ACCCAAATAG CAAGCCGCTC ATGGCGCAGC TGTTCCTTAT    13200

AGTGCAGCAC AGCAGGGACA ACGAGGCATT CAGGGATGCG CTGCTAAACA TAGTAGAGCC    13260

CGAGGGCCGC TGGCTGCTCG ATTTGATAAA CATCCTGCAG AGCATAGTGG TGCAGGAGCG    13320

CAGCTTGAGC CTGGCTGACA AGGTGGCCGC CATCAACTAT TCCATGCTTA GCCTGGGCAA    13380

GTTTTACGCC CGCAAGATAT ACCATACCCC TTACGTTCCC ATAGACAAGG AGGTAAAGAT    13440

CGAGGGGTTC TACATGCGCA TGGCGCTGAA GGTGCTTACC TTGAGCGACG ACCTGGGCGT    13500

TTATCGCAAC GAGCGCATCC ACAAGGCCGT GAGCGTGAGC CGGCGGCGCG AGCTCAGCGA    13560

CCGCGAGCTG ATGCACAGCC TGCAAAGGGC CCTGGCTGGC ACGGGCAGCG GCGATAGAGA    13620

GGCCGAGTCC TACTTTGACG CGGGCGCTGA CCTGCGCTGG GCCCCAAGCC GACGCGCCCT    13680

GGAGGCAGCT GGGGCCGGAC CTGGGCTGGC GGTGGCACCC GCGCGCGCTG GCAACGTCGG    13740

CGGCGTGGAG GAATATGACG AGGACGATGA GTACGAGCCA GAGGACGGCG AGTACTAAGC    13800

GGTGATGTTT CTGATCAGAT GATGCAAGAC GCAACGGACC CGGCGGTGCG GCGGCGCTG    13860

CAGAGCCAGC CGTCCGGCCT TAACTCCACG GACGACTGGC GCCAGGTCAT GGACCGCATC    13920

ATGTCGCTGA CTGCGCGCAA TCCTGACGCG TTCCGGCAGC AGCCGCAGGC CAACCGGCTC    13980

TCCGCAATTC TGGAAGCGGT GGTCCCGGCG CGCGCAAACC CCACGCACGA GAAGGTGCTG    14040
```

-continued

```
GCGATCGTAA ACGCGCTGGC CGAAAACAGG GCCATCCGGC CCGACGAGGC CGGCCTGGTC    14100

TACGACGCGC TGCTTCAGCG CGTGGCTCGT TACAACAGCG GCAACGTGCA GACCAACCTG    14160

GACCGGCTGG TGGGGGATGT GCGCGAGGCC GTGGCGCAGC GTGAGCGCGC GCAGCAGCAG    14220

GGCAACCTGG GCTCCATGGT TGCACTAAAC GCCTTCCTGA GTACACAGCC CGCCAACGTG    14280

CCGCGGGGAC AGGAGGACTA CACCAACTTT GTGAGCGCAC TGCGGCTAAT GGTGACTGAG    14340

ACACCGCAAA GTGAGGTGTA CCAGTCTGGG CCAGACTATT TTTTCCAGAC CAGTAGACAA    14400

GGCCTGCAGA CCGTAAACCT GAGCCAGGCT TTCAAAAACT TGCAGGGGCT GTGGGGGGTG    14460

CGGGCTCCCA CAGGCGACCG CGCGACCGTG TCTAGCTTGC TGACGCCCAA CTCGCGCCTG    14520

TTGCTGCTGC TAATAGCGCC CTTCACGGAC AGTGGCAGCG TGTCCCGGGA CACATACCTA    14580

GGTCACTTGC TGACACTGTA CCGCGAGGCC ATAGGTCAGG CGCATGTGGA CGAGCATACT    14640

TTCCAGGAGA TTACAAGTGT CAGCCGCGCG CTGGGGCAGG AGGACACGGG CAGCCTGGAG    14700

GCAACCCTAA ACTACCTGCT GACCAACCGG CGGCAGAAGA TCCCCTCGTT GCACAGTTTA    14760

AACAGCGAGG AGGAGCGCAT TTTGCGCTAC GTGCAGCAGA GCGTGAGCCT TAACCTGATG    14820

CGCGACGGGG TAACGCCCAG CGTGGCGCTG GACATGACCG CGCGCAACAT GGAACCGGGC    14880

ATGTATGCCT CAAACCGGCC GTTTATCAAC CGCCTAATGG ACTACTTGCA TCGCGCGGCC    14940

GCCGTGAACC CCGAGTATTT CACCAATGCC ATCTTGAACC CGCACTGGCT ACCGCCCCCT    15000

GGTTTCTACA CCGGGGGATT CGAGGTGCCC GAGGGTAACG ATGGATTCCT CTGGGACGAC    15060

ATAGACGACA GCGTGTTTTC CCCGCAACCG CAGACCCTGC TAGAGTTGCA ACAGCGCGAG    15120

CAGGCAGAGG CGGCGCTGCG AAAGGAAAGC TTCCGCAGGC CAAGCAGCTT GTCCGATCTA    15180

GGCGCTGCGG CCCCGCGGTC AGATGCTAGT AGCCCATTTC CAAGCTTGAT AGGGTCTCTT    15240

ACCAGCACTC GCACCACCCG CCCGCGCCTG CTGGGCGAGG AGGAGTACCT AAACAACTCG    15300

CTGCTGCAGC CGCAGCGCGA AAAAAACCTG CCTCCGGCAT TTCCCAACAA CGGGATAGAG    15360

AGCCTAGTGG ACAAGATGAG TAGATGGAAG ACGTACGCGC AGGAGCACAG GGACGTGCCA    15420

GGCCCGCGCC CGCCCACCCG TCGTCAAAGG CACGACCGTC AGCGGGGTCT GGTGTGGGAG    15480

GACGATGACT CGGCAGACGA CAGCAGCGTC CTGGATTTGG GAGGGAGTGG CAACCCGTTT    15540

GCGCACCTTC GCCCCAGGCT GGGGAGAATG TTTTAAAAAA AAAAAAGCAT GATGCAAAAT    15600

AAAAAACTCA CCAAGGCCAT GGCACCGAGC GTTGGTTTTC TTGTATTCCC CTTAGTATGC    15660

GGCGCGCGGC GATGTATGAG GAAGGTCCTC CTCCCTCCTA CGAGAGTGTG GTGAGCGCGG    15720

CGCCAGTGGC GGCGGCGCTG GGTTCTCCCT TCGATGCTCC CCTGGACCCG CCGTTTGTGC    15780

CTCCGCGGTA CCTGCGGCCT ACCGGGGGGA GAAACAGCAT CCGTTACTCT GAGTTGGCAC    15840

CCCTATTCGA CACCACCCGT GTGTACCTGG TGGACAACAA GTCAACGGAT GTGGCATCCC    15900

TGAACTACCA GAACGACCAC AGCAACTTTC TGACCACGGT CATTCAAAAC AATGACTACA    15960

GCCCGGGGGA GGCAAGCACA CAGACCATCA ATCTTGACGA CCGGTCGCAC TGGGGCGGCG    16020

ACCTGAAAAC CATCCTGCAT ACCAACATGC CAAATGTGAA CGAGTTCATG TTTACCAATA    16080

AGTTTAAGGC GCGGGTGATG GTGTCGCGCT TGCCTACTAA GGACAATCAG GTGGAGCTGA    16140

AATACGAGTG GGTGGAGTTC ACGCTGCCCG AGGGCAACTA CTCCGAGACC ATGACCATAG    16200

ACCTTATGAA CAACGCGATC GTGGAGCACT ACTTGAAAGT GGGCAGACAG AACGGGGTTC    16260

TGGAAAGCGA CATCGGGGTA AAGTTTGACA CCCGCAACTT CAGACTGGGG TTTGACCCCG    16320

TCACTGGTCT TGTCATGCCT GGGGTATATA CAAACGAAGC CTTCCATCCA GACATCATTT    16380
```

-continued

```
TGCTGCCAGG ATGCGGGGTG GACTTCACCC ACAGCCGCCT GAGCAACTTG TTGGGCATCC    16440

GCAAGCGGCA ACCCTTCCAG GAGGGCTTTA GGATCACCTA CGATGATCTG GAGGGTGGTA    16500

ACATTCCCGC ACTGTTGGAT GTGGACGCCT ACCAGGCGAG CTTGAAAGAT GACACCGAAC    16560

AGGGCGGGGG TGGCGCAGGC GGCAGCAACA GCAGTGGCAG CGGCGCGGAA GAGAACTCCA    16620

ACGCGGCAGC CGCGGCAATG CAGCCGGTGG AGGACATGAA CGATCATGCC ATTCGCGGCG    16680

ACACCTTTGC CACACGGGCT GAGGAGAAGC GCGCTGAGGC CGAAGCAGCG GCCGAAGCTG    16740

CCGCCCCCGC TGCGCAACCC GAGGTCGAGA AGCCTCAGAA GAAACGGTG ATCAAACCCC     16800

TGACAGAGGA CAGCAAGAAA CGCAGTTACA ACCTAATAAG CAATGACAGC ACCTTCACCC    16860

AGTACCGCAG CTGGTACCTT GCATACAACT ACGGCGACCC TCAGACCGGA ATCCGCTCAT    16920

GGACCCTGCT TTGCACTCCT GACGTAACCT GCGGCTCGGA GCAGGTCTAC TGGTCGTTGC    16980

CAGACATGAT GCAAGACCCC GTGACCTTCC GCTCCACGCG CCAGATCAGC AACTTTCCGG    17040

TGGTGGGCGC CGAGCTGTTG CCCGTGCACT CCAAGAGCTT CTACAACGAC CAGGCCGTCT    17100

ACTCCCAACT CATCCGCCAG TTTACCTCTC TGACCCACGT GTTCAATCGC TTTCCCGAGA    17160

ACCAGATTTT GGCGCGCCCG CCAGCCCCCA CCATCACCAC CGTCAGTGAA AACGTTCCTG    17220

CTCTCACAGA TCACGGGACG CTACCGCTGC GCAACAGCAT CGGAGGAGTC CAGCGAGTGA    17280

CCATTACTGA CGCCAGACGC CGCACCTGCC CCTACGTTTA CAAGGCCCTG GGCATAGTCT    17340

CGCCGCGCGT CCTATCGAGC CGCACTTTTT GAGCAAGCAT GTCCATCCTT ATATCGCCCA    17400

GCAATAACAC AGGCTGGGGC CTGCGCTTCC CAAGCAAGAT GTTTGGCGGG GCCAAGAAGC    17460

GCTCCGACCA ACACCCAGTG CGCGTGCGCG GGCACTACCG CGCGCCCTGG GGCGCGCACA    17520

AACGCGGCCG CACTGGGCGC ACCACCGTCG ATGACGCCAT CGACGCGGTG GTGGAGGAGG    17580

CGCGCAACTA CACGCCCACG CCGCCACCAG TGTCCACAGT GGACGCGGCC ATTCAGACCG    17640

TGGTGCGCGG AGCCCGGCGC TATGCTAAAA TGAAGAGACG GCGGAGGCGC GTAGCACGTC    17700

GCCACCGCCG CCGACCCGGC ACTGCCGCCC AACGCGCGGC GGCGGCCCTG CTTAACCGCG    17760

CACGTCGCAC CGGCCGACGG GCGGCCATGC GGGCCGCTCG AAGGCTGGCC GCGGGTATTG    17820

TCACTGTGCC CCCCAGGTCC AGGCGACGAG CGGCCGCCGC AGCAGCCGCG GCCATTAGTG    17880

CTATGACTCA GGGTCGCAGG GGCAACGTGT ATTGGGTGCG CGACTCGGTT AGCGGCCTGC    17940

GCGTGCCCGT GCGCACCCGC CCCCCGCGCA ACTAGATTGC AAGAAAAAAC TACTTAGACT    18000

CGTACTGTTG TATGTATCCA GCGGCGGCGG CGCGCAACGA AGCTATGTCC AAGCGCAAAA    18060

TCAAAGAAGA GATGCTCCAG GTCATCGCGC CGGAGATCTA TGGCCCCCCG AAGAAGGAAG    18120

AGCAGGATTA CAAGCCCCGA AAGCTAAAGC GGGTCAAAAA GAAAAAGAAA GATGATGATG    18180

ATGAACTTGA CGACGAGGTG GAACTGCTGC ACGCTACCGC GCCCAGGCGA CGGGTACAGT    18240

GGAAAGGTCG ACGCGTAAAA CGTGTTTTGC GACCCGGCAC CACCGTAGTC TTTACGCCCG    18300

GTGAGCGCTC CACCCGCACC TACAAGCGCG TGTATGATGA GGTGTACGGC GACGAGGACC    18360

TGCTTGAGCA GGCCAACGAG CGCCTCGGGG AGTTTGCCTA CGGAAAGCGG CATAAGGACA    18420

TGCTGGCGTT GCCGCTGGAC GAGGGCAACC CAACACCTAG CCTAAAGCCC GTAACACTGC    18480

AGCAGGTGCT GCCCGCGCTT GCACCGTCCG AAGAAAAGCG CGGCCTAAAG CGCGAGTCTG    18540

GTGACTTGGC ACCCACCGTG CAGCTGATGG TACCCAAGCG CCAGCGACTG GAAGATGTCT    18600

TGGAAAAAAT GACCGTGGAA CCTGGGCTGG AGCCCGAGGT CCGCGTGCGG CCAATCAAGC    18660

AGGTGGCGCC GGGACTGGGC GTGCAGACCG TGGACGTTCA GATACCCACT ACCAGTAGCA    18720

CCAGTATTGC CACCGCCACA GAGGGCATGG AGACACAAAC GTCCCCGGTT GCCTCAGCGG    18780
```

```
TGGCGGATGC CGCGGTGCAG GCGGTCGCTG CGGCCGCGTC CAAGACCTCT ACGGAGGTGC    18840

AAACGGACCC GTGGATGTTT CGCGTTTCAG CCCCCCGGCG CCCGCGCGGT TCGAGGAAGT    18900

ACGGCGCCGC CAGCGCGCTA CTGCCCGAAT ATGCCCTACA TCCTTCCATT GCGCCTACCC    18960

CCGGCTATCG TGGCTACACC TACCGCCCCA GAAGACGAGC AACTACCCGA CGCCGAACCA    19020

CCACTGGAAC CCGCCGCCGC CGTCGCCGTC GCCAGCCCGT GCTGGCCCCG ATTTCCGTGC    19080

GCAGGGTGGC TCGCGAAGGA GGCAGGACCC TGGTGCTGCC AACAGCGCGC TACCACCCCA    19140

GCATCGTTTA AAAGCCGGTC TTTGTGGTTC TTGCAGATAT GGCCCTCACC TGCCGCCTCC    19200

GTTTCCCGGT GCCGGGATTC CGAGGAAGAA TGCACCGTAG GAGGGGCATG GCCGGCCACG    19260

GCCTGACGGG CGGCATGCGT CGTGCGCACC ACCGGCGGCG GCGCGCGTCG CACCGTCGCA    19320

TGCGCGGCGG TATCCTGCCC CTCCTTATTC CACTGATCGC CGCGGCGATT GGCGCCGTGC    19380

CCGGAATTGC ATCCGTGGCC TTGCAGGCGC AGAGACACTG ATTAAAAACA AGTTGCATGT    19440

GGAAAAATCA AAATAAAAAG TCTGGACTCT CACGCTCGCT TGGTCCTGTA ACTATTTTGT    19500

AGAATGGAAG ACATCAACTT TGCGTCTCTG GCCCCGCGAC ACGGCTCGCG CCCGTTCATG    19560

GGAAACTGGC AAGATATCGG CACCAGCAAT ATGAGCGGTG GCGCCTTCAG CTGGGGCTCG    19620

CTGTGGAGCG GCATTAAAAA TTTCGGTTCC ACCGTTAAGA ACTATGGCAG CAAGGCCTGG    19680

AACAGCAGCA CAGGCCAGAT GCTGAGGGAT AAGTTGAAAG AGCAAAATTT CCAACAAAAG    19740

GTGGTAGATG GCCTGGCCTC TGGCATTAGC GGGGTGGTGG ACCTGGCCAA CCAGGCAGTG    19800

CAAAATAAGA TTAACAGTAA GCTTGATCCC CGCCCTCCCG TAGAGGAGCC TCCACCGGCC    19860

GTGGAGACAG TGTCTCCAGA GGGGCGTGGC GAAAAGCGTC CGCGCCCCGA CAGGGAAGAA    19920

ACTCTGGTGA CGCAAATAGA CGAGCCTCCC TCGTACGAGG AGGCACTAAA GCAAGGCCTG    19980

CCCACCACCC GTCCCATCGC GCCCATGGCT ACCGGAGTGC TGGGCCAGCA CACACCCGTA    20040

ACGCTGGACC TGCCTCCCCC CGCCGACACC CAGCAGAAAC CTGTGCTGCC AGGCCCGACC    20100

GCCGTTGTTG TAACCCGTCC TAGCCGCGCG TCCCTGCGCC GCGCCGCCAG CGGTCCGCGA    20160

TCGTTGCGGC CCGTAGCCAG TGGCAACTGG CAAAGCACAC TGAACAGCAT CGTGGGTCTG    20220

GGGGTGCAAT CCCTGAAGCG CCGACGATGC TTCTGAATAG CTAACGTGTC GTATGTGTGT    20280

CATGTATGCG TCCATGTCGC CGCCAGAGGA GCTGCTGAGC CGCCGCGCGC CCGCTTTCCA    20340

AGATGGCTAC CCCTTCGATG ATGCCGCAGT GGTCTTACAT GCACATCTCG GGCCAGGACG    20400

CCTCGGAGTA CCTGAGCCCC GGGCTGGTGC AGTTTGCCCG CGCCACCGAG ACGTACTTCA    20460

GCCTGAATAA CAAGTTTAGA AACCCCACGG TGGCGCCTAC GCACGACGTG ACCACAGACC    20520

GGTCCCAGCG TTTGACGCTG CGGTTCATCC CTGTGGACCG TGAGGATACT GCGTACTCGT    20580

ACAAGGCGCG GTTCACCCTA GCTGTGGGTG ATAACCGTGT GCTGGACATG GCTTCCACGT    20640

ACTTTGACAT CCGCGGCGTG CTGGACAGGG GCCCTACTTT TAAGCCCTAC TCTGGCACTG    20700

CCTACAACGC CCTGGCTCCC AAGGGTGCCC CAAATCCTTG CGAATGGGAT GAAGCTGCTA    20760

CTGCTCTTGA AATAAACCTA GAAGAAGAGG ACGATGACAA CGAAGACGAA GTAGACGAGC    20820

AAGCTGAGCA GCAAAAAACT CACGTATTTG GGCAGGCGCC TTATTCTGGT ATAAATATTA    20880

CAAAGGAGGG TATTCAAATA GGTGTCGAAG GTCAAACACC TAAATATGCC GATAAAACAT    20940

TTCAACCTGA ACCTCAAATA GGAGAATCTC AGTGGTACGA AACTGAAATT AATCATGCAG    21000

CTGGGAGAGT CCTTAAAAAG ACTACCCCAA TGAAACCATG TTACGGTTCA TATGCAAAAC    21060

CCACAAATGA AAATGGAGGG CAAGGCATTC TTGTAAAGCA ACAAAATGGA AAGCTAGAAA    21120
```

```
GTCAAGTGGA AATGCAATTT TTCTCAACTA CTGAGGCGAC CGCAGGCAAT GGTGATAACT   21180

TGACTCCTAA AGTGGTATTG TACAGTGAAG ATGTAGATAT AGAAACCCCA GACACTCATA   21240

TTTCTTACAT GCCCACTATT AAGGAAGGTA ACTCACGAGA ACTAATGGGC CAACAATCTA   21300

TGCCCAACAG GCCTAATTAC ATTGCTTTTA GGGACAATTT TATTGGTCTA ATGTATTACA   21360

ACAGCACGGG TAATATGGGT GTTCTGGCGG GCCAAGCATC GCAGTTGAAT GCTGTTGTAG   21420

ATTTGCAAGA CAGAAACACA GAGCTTTCAT ACCAGCTTTT GCTTGATTCC ATTGGTGATA   21480

GAACCAGGTA CTTTTCTATG TGGAATCAGG CTGTTGACAG CTATGATCCA GATGTTAGAA   21540

TTATTGAAAA TCATGGAACT GAAGATGAAC TTCCAAATTA CTGCTTTCCA CTGGGAGGTG   21600

TGATTAATAC AGAGACTCTT ACCAAGGTAA AACCTAAAAC AGGTCAGGAA AATGGATGGG   21660

AAAAAGATGC TACAGAATTT TCAGATAAAA ATGAAATAAG AGTTGGAAAT AATTTTGCCA   21720

TGGAAATCAA TCTAAATGCC AACCTGTGGA GAAATTTCCT GTACTCCAAC ATAGCGCTGT   21780

ATTTGCCCGA CAAGCTAAAG TACAGTCCTT CCAACGTAAA AATTTCTGAT AACCCAAACA   21840

CCTACGACTA CATGAACAAG CGAGTGGTGG CTCCCGGGTT AGTGGACTGC TACATTAACC   21900

TTGGAGCACG CTGGTCCCTT GACTATATGG ACAACGTCAA CCCATTTAAC CACCACCGCA   21960

ATGCTGGCCT GCGCTACCGC TCAATGTTGC TGGGCAATGG TCGCTATGTG CCCTTCCACA   22020

TCCAGGTGCC TCAGAAGTTC TTTGCCATTA AAAACCTCCT TCTCCTGCCG GGCTCATACA   22080

CCTACGAGTG GAACTTCAGG AAGGATGTTA ACATGGTTCT GCAGAGCTCC CTAGGAAATG   22140

ACCTAAGGGT TGACGGAGCC AGCATTAAGT TTGATAGCAT TTGCCTTTAC GCCACCTTCT   22200

TCCCCATGGC CCACAACACC GCCTCCACGC TTGAGGCCAT GCTTAGAAAC GACACCAACG   22260

ACCAGTCCTT TAACGACTAT CTCTCCGCCG CCAACATGCT CTACCCTATA CCCGCCAACG   22320

CTACCAACGT GCCCATATCC ATCCCCTCCC GCAACTGGGC GGCTTTCCGC GGCTGGGCCT   22380

TCACGCGCCT TAAGACTAAG GAAACCCCAT CACTGGGCTC GGGCTACGAC CCTTATTACA   22440

CCTACTCTGG CTCTATACCC TACCTAGATG GAACCTTTTA CCTCAACCAC ACCTTTAAGA   22500

AGGTGGCCAT TACCTTTGAC TCTTCTGTCA GCTGGCCTGG CAATGACCGC CTGCTTACCC   22560

CCAACGAGTT TGAAATTAAG CGCTCAGTTG ACGGGGAGGG TTACAACGTT GCCCAGTGTA   22620

ACATGACCAA AGACTGGTTC CTGGTACAAA TGCTAGCTAA CTACAACATT GGCTACCAGG   22680

GCTTCTATAT CCCAGAGAGC TACAAGGACC GCATGTACTC CTTCTTTAGA AACTTCCAGC   22740

CCATGAGCCG TCAGGTGGTG GATGATACTA AATACAAGGA CTACCAACAG GTGGGCATCC   22800

TACACCAACA CAACAACTCT GGATTTGTTG GCTACCTTGC CCCCACCATG CGCGAAGGAC   22860

AGGCCTACCC TGCTAACTTC CCCTATCCGC TTATAGGCAA GACCGCAGTT GACAGCATTA   22920

CCCAGAAAAA GTTTCTTTGC GATCGCACCC TTTGGCGCAT CCCATTCTCC AGTAACTTTA   22980

TGTCCATGGG CGCACTCACA GACCTGGGCC AAAACCTTCT CTACGCCAAC TCCGCCCACG   23040

CGCTAGACAT GACTTTTGAG GTGGATCCCA TGGACGAGCC CACCCTTCTT TATGTTTTGT   23100

TTGAAGTCTT TGACGTGGTC CGTGTGCACC GGCCGCACCG CGGCGTCATC GAAACCGTGT   23160

ACCTGCGCAC GCCCTTCTCG GCCGGCAACG CCACAACATA AAGAAGCAAG CAACATCAAC   23220

AACAGCTGCC GCCATGGGCT CCAGTGAGCA GGAACTGAAA GCCATTGTCA AGATCTTGG   23280

TTGTGGGCCA TATTTTTTGG GCACCTATGA CAAGCGCTTT CCAGGCTTTG TTTCTCCACA   23340

CAAGCTCGCC TGCGCCATAG TCAATACGGC CGGTCGCGAG ACTGGGGGCG TACACTGGAT   23400

GGCCTTTGCC TGGAACCCGC ACTCAAAAAC ATGCTACCTC TTTGAGCCCT TTGGCTTTTC   23460

TGACCAGCGA CTCAAGCAGG TTTACCAGTT TGAGTACGAG TCACTCCTGC GCCGTAGCGC   23520
```

```
CATTGCTTCT TCCCCCGACC GCTGTATAAC GCTGGAAAAG TCCACCCAAA GCGTACAGGG    23580

GCCCAACTCG GCCGCCTGTG GACTATTCTG CTGCATGTTT CTCCACGCCT TTGCCAACTG    23640

GCCCCAAACT CCCATGGATC ACAACCCCAC CATGAACCTT ATTACCGGGG TACCCAACTC    23700

CATGCTCAAC AGTCCCCAGG TACAGCCCAC CCTGCGTCGC AACCAGGAAC AGCTCTACAG    23760

CTTCCTGGAG CGCCACTCGC CCTACTTCCG CAGCCACAGT GCGCAGATTA GGAGCGCCAC    23820

TTCTTTTTGT CACTTGAAAA ACATGTAAAA ATAATGTACT AGAGACACTT TCAATAAAGG    23880

CAAATGCTTT TATTTGTACA CTCTCGGGTG ATTATTTACC CCCACCCTTG CCGTCTGCGC    23940

CGTTTAAAAA TCAAAGGGGT TCTGCCGCGC ATCGCTATGC GCCACTGGCA GGGACACGTT    24000

GCGATACTGG TGTTTAGTGC TCCACTTAAA CTCAGGCACA ACCATCCGCG GCAGCTCGGT    24060

GAAGTTTTCA CTCCACAGGC TGCGCACCAT CACCAACGCG TTTAGCAGGT CGGGCGCCGA    24120

TATCTTGAAG TCGCAGTTGG GGCCTCCGCC CTGCGCGCGC GAGTTGCGAT ACACAGGGTT    24180

GCAGCACTGG AACACTATCA GCGCCGGGTG GTGCACGCTG GCCAGCACGC TCTTGTCGGA    24240

GATCAGATCC GCGTCCAGGT CCTCCGCGTT GCTCAGGGCG AACGGAGTCA ACTTTGGTAG    24300

CTGCCTTCCC AAAAAGGGCG CGTGCCCAGG CTTTGAGTTG CACTCGCACC GTAGTGGCAT    24360

CAAAAGGTGA CCGTGCCCGG TCTGGGCGTT AGGATACAGC GCCTGCATAA AAGCCTTGAT    24420

CTGCTTAAAA GCCACCTGAG CCTTTGCGCC TTCAGAGAAG AACATGCCGC AAGACTTGCC    24480

GGAAAACTGA TTGGCCGGAC AGGCCGCGTC GTGCACGCAG CACCTTGCGT CGGTGTTGGA    24540

GATCTGCACC ACATTTCGGC CCCACCGGTT CTTCACGATC TTGGCCTTGC TAGACTGCTC    24600

CTTCAGCGCG CGCTGCCCGT TTTCGCTCGT CACATCCATT TCAATCACGT GCTCCTTATT    24660

TATCATAATG CTTCCGTGTA GACACTTAAG CTCGCCTTCG ATCTCAGCGC AGCGGTGCAG    24720

CCACAACGCG CAGCCCGTGG GCTCGTGATG CTTGTAGGTC ACCTCTGCAA ACGACTGCAG    24780

GTACGCCTGC AGGAATCGCC CCATCATCGT CACAAAGGTC TTGTTGCTGG TGAAGGTCAG    24840

CTGCAACCCG CGGTGCTCCT CGTTCAGCCA GGTCTTGCAT ACGGCCGCCA GAGCTTCCAC    24900

TTGGTCAGGC AGTAGTTTGA AGTTCGCCTT TAGATCGTTA TCCACGTGGT ACTTGTCCAT    24960

CAGCGCGCGC GCAGCCTCCA TGCCCTTCTC CCACGCAGAC ACGATCGGCA CACTCAGCGG    25020

GTTCATCACC GTAATTTCAC TTTCCGCTTC GCTGGGCTCT TCCTCTTCCT CTTGCGTCCG    25080

CATACCACGC GCCACTGGGT CGTCTTCATT CAGCCGCCGC ACTGTGCGCT TACCTCCTTT    25140

GCCATGCTTG ATTAGCACCG GTGGGTTGCT GAAACCCACC ATTTGTAGCG CCACATCTTC    25200

TCTTTCTTCC TCGCTGTCCA CGATTACCTC TGGTGATGGC GGGCGCTCGG GCTTGGGAGA    25260

AGGGCGCTTC TTTTTCTTCT TGGGCGCAAT GGCCAAATCC GCCGCCGAGG TCGATGGCCG    25320

CGGGCTGGGT GTGCGCGGCA CCAGCGCGTC TTGTGATGAG TCTTCCTCGT CCTCGGACTC    25380

GATACGCCGC CTCATCCGCT TTTTTGGGGG CGCCCGGGGA GGCGGCGGCG ACGGGACGG    25440

GGACGACACG TCCTCCATGG TTGGGGACG TCGCGCCGCA CCGCGTCCGC GCTCGGGGT    25500

GGTTTCGCGC TGCTCCTCTT CCCGACTGGC CATTTCCTTC TCCTATAGGC AGAAAAGAT    25560

CATGGAGTCA GTCGAGAAGA AGGACAGCCT AACCGCCCCC TCTGAGTTCG CCACCACCGC    25620

CTCCACCGAT GCCGCCAACG CGCCTACCAC CTTCCCCGTC GAGGCACCCC CGCTTGAGGA    25680

GGAGGAAGTG ATTATCGAGC AGGACCCAGG TTTTGTAAGC GAAGACGACG AGGACCGCTC    25740

AGTACCAACA GAGGATAAAA AGCAAGACCA GGACAACGCA GAGGCAAACG AGGAACAAGT    25800

CGGGCGGGGG GACGAAAGGC ATGGCGACTA CCTAGATGTG GGAGACGACG TGCTGTTGAA    25860
```

-continued

```
GCATCTGCAG CGCCAGTGCG CCATTATCTG CGACGCGTTG CAAGAGCGCA GCGATGTGCC    25920

CCTCGCCATA GCGGATGTCA GCCTTGCCTA CGAACGCCAC CTATTCTCAC CGCGCGTACC    25980

CCCCAAACGC CAAGAAAACG GCACATGCGA GCCCAACCCG CGCCTCAACT TCTACCCCGT    26040

ATTTGCCGTG CCAGAGGTGC TTGCCACCTA TCACATCTTT TTCCAAAACT GCAAGATACC    26100

CCTATCCTGC CGTGCCAACC GCAGCCGAGC GGACAAGCAG CTGGCCTTGC GGCAGGGCGC    26160

TGTCATACCT GATATCGCCT CGCTCAACGA AGTGCCAAAA ATCTTTGAGG GTCTTGGACG    26220

CGACGAGAAG CGCGCGGCAA ACGCTCTGCA ACAGGAAAAC AGCGAAAATG AAAGTCACTC    26280

TGGAGTGTTG GTGGAACTCG AGGGTGACAA CGCGCGCCTA GCCGTACTAA AACGCAGCAT    26340

CGAGGTCACC CACTTTGCCT ACCCGGCACT TAACCTACCC CCCAAGGTCA TGAGCACAGT    26400

CATGAGTGAG CTGATCGTGC GCCGTGCGCA GCCCCTGGAG AGGGATGCAA ATTTGCAAGA    26460

ACAAACAGAG GAGGGCCTAC CCGCAGTTGG CGACGAGCAG CTAGCGCGCT GGCTTCAAAC    26520

GCGCGAGCCT GCCGACTTGG AGGAGCGACG CAAACTAATG ATGGCCGCAG TGCTCGTTAC    26580

CGTGGAGCTT GAGTGCATGC AGCGGTTCTT TGCTGACCCG GAGATGCAGC GCAAGCTAGA    26640

GGAAACATTG CACTACACCT TTCGACAGGG CTACGTACGC CAGGCCTGCA AGATCTCCAA    26700

CGTGGAGCTC TGCAACCTGG TCTCCTACCT TGGAATTTTG CACGAAAACC GCCTTGGGCA    26760

AAACGTGCTT CATTCCACGC TCAAGGGCGA GGCGCGCCGC GACTACGTCC GCGACTGCGT    26820

TTACTTATTT CTATGCTACA CCTGGCAGAC GGCCATGGGC GTTTGGCAGC AGTGCTTGGA    26880

GGAGTGCAAC CTCAAGGAGC TGCAGAAACT GCTAAAGCAA AACTTGAAGG ACCTATGGAC    26940

GGCCTTCAAC GAGCGCTCCG TGGCCGCGCA CCTGGCGGAC ATCATTTTCC CCGAACGCCT    27000

GCTTAAAACC CTGCAACAGG GTCTGCCAGA CTTCACCAGT CAAAGCATGT TGCAGAACTT    27060

TAGGAACTTT ATCCTAGAGC GCTCAGGAAT CTTGCCCGCC ACCTGCTGTG CACTTCCTAG    27120

CGACTTTGTG CCCATTAAGT ACCGCGAATG CCCTCCGCCG CTTTGGGGCC ACTGCTACCT    27180

TCTGCAGCTA GCCAACTACC TTGCCTACCA CTCTGACATA ATGGAAGACG TGAGCGGTGA    27240

CGGTCTACTG GAGTGTCACT GTCGCTGCAA CCTATGCACC CCGCACCGCT CCCTGGTTTG    27300

CAATTCGCAG CTGCTTAACG AAAGTCAAAT TATCGGTACC TTTGAGCTGC AGGGTCCCTC    27360

GCCTGACGAA AAGTCCGCGG CTCCGGGGTT GAAACTCACT CCGGGGCTGT GGACGTCGGC    27420

TTACCTTCGC AAATTTGTAC CTGAGGACTA CCACGCCCAC GAGATTAGGT TCTACGAAGA    27480

CCAATCCCGC CCGCCAAATG CGGAGCTTAC CGCCTGCGTC ATTACCCAGG GCCACATTCT    27540

TGGCCAATTG CAAGCCATCA ACAAAGCCCG CCAAGAGTTT CTGCTACGAA AGGGACGGGG    27600

GGTTTACTTG GACCCCCAGT CCGGCGAGGA GCTCAACCCA ATCCCCCCGC CGCCGCAGCC    27660

CTATCAGCAG CAGCCGCGGG CCCTTGCTTC CCAGGATGGC ACCCAAAAAG AAGCTGCAGC    27720

TGCCGCCGCC ACCCACGGAC GAGGAGGAAT ACTGGGACAG TCAGGCAGAG GAGGTTTTGG    27780

ACGAGGAGGA GGAGGACATG ATGGAAGACT GGGAGAGCCT AGACGAGGAA GCTTCCGAGG    27840

TCGAAGAGGT GTCAGACGAA ACACCGTCAC CCTCGGTCGC ATTCCCCTCG CCGGCGCCCC    27900

AGAAATCGGC AACCGGTTCC AGCATGGCTA CAACCTCCGC TCCTCAGGCG CCGCCGGCAC    27960

TGCCCGTTCG CCGACCCAAC CGTAGATGGG ACACCACTGG AACCAGGCC GGTAAGTCCA    28020

AGCAGCCGCC GCCGTTAGCC CAAGAGCAAC AACAGCGCCA AGGCTACCGC TCATGGCGCG    28080

GGCACAAGAA CGCCATAGTT GCTTGCTTGC AAGACTGTGG GGGCAACATC TCCTTCGCCC    28140

GCCGCTTTCT TCTCTACCAT CACGGCGTGG CCTTCCCCCG TAACATCCTG CATTACTACC    28200

GTCATCTCTA CAGCCCATAC TGCACCGGCG GCAGCGGCAG CGGCAGCAAC AGCAGCGGCC    28260
```

-continued

```
ACACAGAAGC AAAGGCGACC GGATAGCAAG ACTCTGACAA AGCCCAAGAA ATCCACAGCG    28320

GCGGCAGCAG CAGGAGGAGG AGCGCTGCGT CTGGCGCCCA ACGAACCCGT ATCGACCCGC    28380

GAGCTTAGAA ACAGGATTTT TCCCACTCTG TATGCTATAT TTCAACAGAG CAGGGGCCAA    28440

GAACAAGAGC TGAAAATAAA AAACAGGTCT CTGCGATCCC TCACCCGCAG CTGCCTGTAT    28500

CACAAAAGCG AAGATCAGCT TCGGCGCACG CTGGAAGACG CGGAGGCTCT CTTCAGTAAA    28560

TACTGCGCGC TGACTCTTAA GGACTAGTTT CGCGCCCTTT CTCAAATTTA AGCGCGAAAA    28620

CTACGTCATC TCCAGCGGCC ACACCCGGCG CCAGCACCTG TCGTCAGCGC CATTATGAGC    28680

AAGGAAATTC CCACGCCCTA CATGTGGAGT TACCAGCCAC AAATGGGACT TGCGGCTGGA    28740

GCTGCCCAAG ACTACTCAAC CCGAATAAAC TACATGAGCG CGGGACCCCA CATGATATCC    28800

CGGGTCAACG GAATCCGCGC CCACCGAAAC CGAATTCTCT TGGAACAGGC GGCTATTACC    28860

ACCACACCTC GTAATAACCT TAATCCCCGT AGTTGGCCCG CTGCCCTGGT GTACCAGGAA    28920

AGTCCCGCTC CCACCACTGT GGTACTTCCC AGAGACGCCC AGGCCGAAGT TCAGATGACT    28980

AACTCAGGGG CGCAGCTTGC GGGCGGCTTT CGTCACAGGG TGCGGTCGCC CGGGCAGGGT    29040

ATAACTCACC TGACAATCAG AGGGCGAGGT ATTCAGCTCA ACGACGAGTC GGTGAGCTCC    29100

TCGCTTGGTC TCCGTCCGGA CGGGACATTT CAGATCGGCG GCGCCGGCCG TCCTTCATTC    29160

ACGCCTCGTC AGGCAATCCT AACTCTGCAG ACCTCGTCCT CTGAGCCGCG CTCTGGAGGC    29220

ATTGGAACTC TGCAATTTAT TGAGGAGTTT GTGCCATCGG TCTACTTTAA CCCCTTCTCG    29280

GGACCTCCCG GCCACTATCC GGATCAATTT ATTCCTAACT TTGACGCGGT AAAGGACTCG    29340

GCGGACGGCT ACGACTGAAT GTTAATTAAG TTCCTGTCCA TCCGCACCCA CTATCTTCAT    29400

GTTGTTGCAG ATGAAGCGCG CAAGACCGTC TGAAGATACC TTCAACCCCG TGTATCCATA    29460

TGACACGGAA ACCGGTCCTC CAACTGTGCC TTTTCTTACT CCTCCCTTTG TATCCCCCAA    29520

TGGGTTTCAA GAGAGTCCCC CTGGGGTACT CTCTTTGCGC CTATCCGAAC CTCTAGTTAC    29580

CTCCAATGGC ATGCTTGCGC TCAAAATGGG CAACGGCCTC TCTCTGGACG AGGCCGGCAA    29640

CCTTACCTCC CAAAATGTAA CCACTGTGAG CCCACCTCTC AAAAAAACCA AGTCAAACAT    29700

AAACCTGGAA ATATCTGCAC CCCTCACAGT TACCTCAGAA GCCCTAACTG TGGCTGCCGC    29760

CGCACCTCTA ATGGTCGCGG GCAACACACT CACCATGCAA TCACAGGCCC CGCTAACCGT    29820

GCACGACTCC AAACTTAGCA TTGCCACCCA AGGACCCCTC ACAGTGTCAG AAGGAAAGCT    29880

AGCCCTGCAA ACATCAGGCC CCCTCACCAC CACCGATAGC AGTACCCTTA CTATCACTGC    29940

CTCACCCCCT CTAACTACTG CCACTGGTAG CTTGGGCATT GACTTGAAAG AGCCCATTTA    30000

TACACAAAAT GGAAAACTAG GACTAAAGTA CGGGGCTCCT TTGCATGTAA CAGACGACCT    30060

AAACACTTTG ACCGTAGCAA CTGGTCCAGG TGTGACTATT AATAATACTT CCTTGCAAAC    30120

TAAAGTTACT GGAGCCTTGG GTTTTGATTC ACAAGGCAAT ATGCAACTTA ATGTAGCAGG    30180

AGGACTAAGG ATTGATTCTC AAAACAGACG CCTTATACTT GATGTTAGTT ATCCGTTTGA    30240

TGCTCAAAAC CAACTAAATC TAAGACTAGG ACAGGGCCCT CTTTTTATAA ACTCAGCCCA    30300

CAACTTGGAT ATTAACTACA ACAAAGGCCT TTACTTGTTT ACAGCTTCAA ACAATTCCAA    30360

AAAGCTTGAG GTTAACCTAA GCACTGCCAA GGGGTTGATG TTTGACGCTA CAGCCATAGC    30420

CATTAATGCA GGAGATGGGC TTGAATTTGG TTCACCTAAT GCACCAAACA CAAATCCCCT    30480

CAAAACAAAA ATTGGCCATG GCCTAGAATT TGATTCAAAC AAGGCTATGG TTCCTAAACT    30540

AGGAACTGGC CTTAGTTTTG ACAGCACAGG TGCCATTACA GTAGGAAACA AAAATAATGA    30600
```

```
TAAGCTAACT TTGTGGACCA CACCAGCTCC ATCTCCTAAC TGTAGACTAA ATGCAGAGAA    30660

AGATGCTAAA CTCACTTTGG TCTTAACAAA ATGTGGCAGT CAAATACTTG CTACAGTTTC    30720

AGTTTTGGCT GTTAAAGGCA GTTTGGCTCC AATATCTGGA ACAGTTCAAA GTGCTCATCT    30780

TATTATAAGA TTTGACGAAA ATGGAGTGCT ACTAAACAAT TCCTTCCTGG ACCCAGAATA    30840

TTGGAACTTT AGAAATGGAG ATCTTACTGA AGGCACAGCC TATACAAACG CTGTTGGATT    30900

TATGCCTAAC CTATCAGCTT ATCCAAAATC TCACGGTAAA ACTGCCAAAA GTAACATTGT    30960

CAGTCAAGTT TACTTAAACG GAGACAAAAC TAAACCTGTA ACACTAACCA TTACACTAAA    31020

CGGTACACAG GAAACAGGAG ACACAACTCC AAGTGCATAC TCTATGTCAT TTTCATGGGA    31080

CTGGTCTGGC CACAACTACA TTAATGAAAT ATTTGCCACA TCCTCTTACA CTTTTTCATA    31140

CATTGCCCAA GAATAAAGAA TCGTTTGTGT TATGTTTCAA CGTGTTTATT TTTCAATTGC    31200

AGAAAATTTC AAGTCATTTT TCATTCAGTA GTATAGCCCC ACCACCACAT AGCTTATACA    31260

GATCACCGTA CCTTAATCAA ACTCACAGAA CCCTAGTATT CAACCTGCCA CCTCCCTCCC    31320

AACACACAGA GTACACAGTC CTTTCTCCCC GGCTGGCCTT AAAAAGCATC ATATCATGGG    31380

TAACAGACAT ATTCTTAGGT GTTATATTCC ACACGGTTTC CTGTCGAGCC AAACGCTCAT    31440

CAGTGATATT AATAAACTCC CCGGGCAGCT CACTTAAGTT CATGTCGCTG TCCAGCTGCT    31500

GAGCCACAGG CTGCTGTCCA ACTTGCGGTT GCTTAACGGG CGGCGAAGGA GAAGTCCACG    31560

CCTACATGGG GGTAGAGTCA TAATCGTGCA TCAGGATAGG GCGGTGGTGC TGCAGCAGCG    31620

CGCGAATAAA CTGCTGCCGC CGCCGCTCCG TCCTGCAGGA ATACAACATG GCAGTGGTCT    31680

CCTCAGCGAT GATTCGCACC GCCCGCAGCA TAAGGCGCCT TGTCCTCCGG GCACAGCAGC    31740

GCACCCTGAT CTCACTTAAA TCAGCACAGT AACTGCAGCA CAGCACCACA ATATTGTTCA    31800

AAATCCCACA GTGCAAGGCG CTGTATCCAA AGCTCATGGC GGGGACCACA GAACCCACGT    31860

GGCCATCATA CCACAAGCGC AGGTAGATTA AGTGGCGACC CCTCATAAAC ACGCTGGACA    31920

TAAACATTAC CTCTTTTGGC ATGTTGTAAT TCACCACCTC CCGGTACCAT ATAAACCTCT    31980

GATTAAACAT GGCGCCATCC ACCACCATCC TAAACCAGCT GGCCAAAACC TGCCCGCCGG    32040

CTATACACTG CAGGGAACCG GGACTGGAAC AATGACAGTG GAGAGCCCAG GACTCGTAAC    32100

CATGGATCAT CATGCTCGTC ATGATATCAA TGTTGGCACA ACACAGGCAC ACGTGCATAC    32160

ACTTCCTCAG GATTACAAGC TCCTCCCGCG TTAGAACCAT ATCCCAGGGA ACAACCCATT    32220

CCTGAATCAG CGTAAATCCC ACACTGCAGG GAAGACCTCG CACGTAACTC ACGTTGTGCA    32280

TTGTCAAAGT GTTACATTCG GGCAGCAGCG GATGATCCTC CAGTATGGTA GCGCGGGTTT    32340

CTGTCTCAAA AGGAGGTAGA CGATCCCTAC TGTACGGAGT GCGCCGAGAC AACCGAGATC    32400

GTGTTGGTCG TAGTGTCATG CCAAATGGAA CGCCGGACGT AGTCATATTT CCTGAAGCAA    32460

AACCAGGTGC GGGCGTGACA AACAGATCTG CGTCTCCGGT CTCGCCGCTT AGATCGCTCT    32520

GTGTAGTAGT TGTAGTATAT CCACTCTCTC AAAGCATCCA GGCGCCCCCT GGCTTCGGGT    32580

TCTATGTAAA CTCCTTCATG CGCCGCTGCC CTGATAACAT CCACCACCGC AGAATAAGCC    32640

ACACCCAGCC AACCTACACA TTCGTTCTGC GAGTCACACA CGGGAGGAGC GGGAAGAGCT    32700

GGAAGAACCA TGTTTTTTTT TTTATTCCAA AAGATTATCC AAAACCTCAA AATGAAGATC    32760

TATTAAGTGA ACGCGCTCCC CTCCGGTGGC GTGGTCAAAC TCTACAGCCA AGAACAGAT    32820

AATGGCATTT GTAAGATGTT GCACAATGGC TTCCAAAAGG CAAACGGCCC TCACGTCCAA    32880

GTGGACGTAA AGGCTAAACC CTTCAGGGTG AATCTCCTCT ATAAACATTC CAGCACCTTC    32940

AACCATGCCC AAATAATTCT CATCTCGCCA CCTTCTCAAT ATATCTCTAA GCAAATCCCG    33000
```

-continued

```
AATATTAAGT CCGGCCATTG TAAAAATCTG CTCCAGAGCG CCCTCCACCT TCAGCCTCAA    33060

GCAGCGAATC ATGATTGCAA AAATTCAGGT TCCTCACAGA CCTGTATAAG ATTCAAAAGC    33120

GGAACATTAA CAAAAATACC GCGATCCCGT AGGTCCCTTC GCAGGGCCAG CTGAACATAA    33180

TCGTGCAGGT CTGCACGGAC CAGCGCGGCC ACTTCCCCGC CAGGAACCTT GACAAAAGAA    33240

CCCACACTGA TTATGACACG CATACTCGGA GCTATGCTAA CCAGCGTAGC CCCGATGTAA    33300

GCTTTGTTGC ATGGGCGGCG ATATAAAATG CAAGGTGCTG CTCAAAAAAT CAGGCAAAGC    33360

CTCGCGCAAA AAGAAAGCA CATCGTAGTC ATGCTCATGC AGATAAAGGC AGGTAAGCTC    33420

CGGAACCACC ACAGAAAAAG ACACCATTTT TCTCTCAAAC ATGTCTGCGG GTTTCTGCAT    33480

AAACACAAAA TAAAATAACA AAAAAACATT TAAACATTAG AAGCCTGTCT TACAACAGGA    33540

AAAACAACCC TTATAAGCAT AAGACGGACT ACGGCCATGC CGGCGTGACC GTAAAAAAAC    33600

TGGTCACCGT GATTAAAAAG CACCACCGAC AGCTCCTCGG TCATGTCCGG AGTCATAATG    33660

TAAGACTCGG TAAACACATC AGGTTGATTC ATCGGTCAGT GCTAAAAAGC GACCGAAATA    33720

GCCCGGGGGA ATACATACCC GCAGGCGTAG AGACAACATT ACAGCCCCCA TAGGAGGTAT    33780

AACAAAATTA ATAGGAGAGA AAAACACATA AACACCTGAA AAACCCTCCT GCCTAGGCAA    33840

AATAGCACCC TCCCGCTCCA GAACAACATA CAGCGCTTCA CAGCGGCAGC CTAACAGTCA    33900

GCCTTACCAG TAAAAAAGAA AACCTATTAA AAAAACACCA CTCGACACGG CACCAGCTCA    33960

ATCAGTCACA GTGTAAAAAA GGGCCAAGTG CAGAGCGAGT ATATATAGGA CTAAAAAATG    34020

ACGTAACGGT TAAAGTCCAC AAAAAACACC CAGAAAACCG CACGCGAACC TACGCCCAGA    34080

AACGAAAGCC AAAAAACCCA CAACTTCCTC AAATCGTCAC TTCCGTTTTC CCACGTTACG    34140

TAACTTCCCA TTTTAAGAAA ACTACAATTC CCAACACATA CAAGTTACTC CGCCCTAAAA    34200

CCTACGTCAC CCGCCCCGTT CCCACGCCCC GCGCCACGTC ACAAACTCCA CCCCCTCATT    34260

ATCATATTGG CTTCAATCCA AAATAAGGTA TATTATTGAT GAT                     34303
```

(2) INFORMATION FOR SEQ ID NO:5:

(i) SEQUENCE CHARACTERISTICS:
        (A) LENGTH: 380 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

```
CCAGGCTTTA CACTTTATGC TTCCGGCTCG TATGTTGTGT GGAATTGTGA GCGGATAACA     60

ATTTCACACA GGAAACAGCT ATGACCATGA TTACGCCAAG CGCGCAATTA ACCCTCACTA    120

AAGGGAACAA AAGCTGGGTA CCGGGCCCCC CCTCGAGGTC GACGGTATCG ATAAGCTTAC    180

GCGTGGCCTA GCGGCCGAA TTCCTGCAGC CCGGGGGATC CACTAGTTCT AGAGCGGCCG    240

CCACCGCGGC GCCTTAATTA ATACGTAAGC TCCAATTCGC CCTATAGTGA GTCGTATTAC    300

GCGCGCTCAC TGGCCGTCGT TTTACAACGT CGTGACTGGG AAAACCCTGG CGTTACCCAA    360

CTTAATCGCC TTGCAGCACA                                                380
```

(2) INFORMATION FOR SEQ ID NO:6:

(i) SEQUENCE CHARACTERISTICS:
        (A) LENGTH: 21 base pairs
        (B) TYPE: nucleic acid (C) STRANDEDNESS: single
          (D) TOPOLOGY: linear (ii) MOLECULE TYPE: other nucleic acid
         (A) DESCRIPTION: /desc = "DNA"

(xi) SEQUENCE DESCRIPTION: SEQ ID NO:6:

```
TGCCGCAGCA CCGGATGCAT C                                              21
```

(2) INFORMATION FOR SEQ ID NO:7:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:7:

```
GCGTCCGGAG GCTGCCATGC GGCAGGG                                        27
```

(2) INFORMATION FOR SEQ ID NO:8:

(i) SEQUENCE CHARACTERISTICS:
         (A) LENGTH: 1481 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:8:

```
GGCTGCCATG CGGCAGGGAT ACGGCGCTAA CGATGCATCT CAACAATTGT TGTGTAGGTA      60
CTCCGCCGCC GAGGGACCTG AGCGAGTCCG CATCGACCGG ATCGGAAAAC CTCTCGAGAA     120
AGGCGTCTAA CCAGTCACAG TCGCAAGGTA GGCTGAGCAC CGTGGCGGGC GGCAGCGGGC     180
GGCGGTCGGG GTTGTTTCTG GCGGAGGTGC TGCTGATGAT GTAATTAAAG TAGGCGGTCT     240
TGAGACGGCG GATGGTCGAC AGAAGCACCA TGTCCTTGGG TCCGGCCTGC TGAATGCGCA     300
GGCGGTCGGC CATGCCCCAG GCTTCGTTTT GACATCGGCG CAGGTCTTTG TAGTAGTCTT     360
GCATGAGCCT TTCTACCGGC ACTTCTTCTT CTCCTTCCTC TTGTCCTGCA TCTCTTGCAT     420
CTATCGCTGC GGCGGCGGCG GAGTTTGGCC GTAGGTGGCG CCCTCTTCCT CCCATGCGTG     480
TGACCCCGAA GCCCCTCATC GGCTGAAGCA GGGCTAGGTC GGCGACAACG CGCTCGGCTA     540
ATATGGCCTG CTGCACCTGC GTGAGGGTAG ACTGGAAGTC ATCCATGTCC ACAAAGCGGT     600
GGTATGCGCC CGTGTTGATG GTGTAAGTGC AGTTGGCCAT AACGGACCAG TTAACGGTCT     660
GGTGACCCGG CTGCGAGAGC TCGGTGTACC TGAGACGCGA GTAAGCCCTC GAGTCAAATA     720
CGTAGTCGTT GCAAGTCCGC ACCAGGTACT GGTATCCCAC CAAAAAGTGC GGCGGCGGCT     780
GGCGGTAGAG GGGCCAGCGT AGGGTGGCCG GGGCTCCGGG GGCGAGATCT TCCAACATAA     840
GGCGATGATA TCCGTAGATG TACCTGGACA TCCAGGTGAT GCCGGCGGCG GTGGTGGAGG     900
CGCGCGGAAA GTCGCGGACG CGGTTCCAGA TGTTGCGCAG CGGCAAAAAG TGCTCCATGG     960
TCGGGACGCT CTGGCCGGTC AGGCGCGCGC AATCGTTGAC GCTCTACCGT GCAAAAGGAG    1020
AGCCTGTAAG CGGGCACTCT TCCGTGGTCT GGTGGATAAA TTCGCAAGGG TATCATGGCG    1080
GACGACCGGG GTTCGAGCCC CGTATCCGGC CGTCCGCCGT GATCCATGCG GTTACCGCCC    1140
GCGTGTCGAA CCCAGGTGTG CGACGTCAGA CAACGGGGGA GTGCTCCTTT TGGCTTCCTT    1200
```

```
CCAGGCGCGG CGGCTGCTGC GCTAGCTTTT TTGGCCACTG GCCGCGCGCA GCGTAAGCGG    1260

TTAGGCTGGA AAGCGAAAGC ATTAAGTGGC TCGCTCCCTG TAGCCGGAGG GTTATTTTCC    1320

AAGGGTTGAG TCGCGGGACC CCCGGTTCGA GTCTCGGACC GGCCGGACTG CGGCGAACGG    1380

GGGTTTGCCT CCCCGTCATG CAAGACCCCG CTTGCAAATT CCTCCGGAAA CAGGGACGAG    1440

CCCCTTTTTT GCTTTTCCCA GATGCATCCG GTGCTGCGGC A                       1481
```

(2) INFORMATION FOR SEQ ID NO:9:

(i) SEQUENCE CHARACTERISTICS:
        (A) LENGTH: 3364 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

```
GAATTCCCCA TCCTGGTCTA TAGAGAGAGT TCCAGAACAG CCAGGGCTAC AGATAAACCC      60

ATCTGGAAAA ACAAAGTTGA ATGACCCAAG AGGGGTTCTC AGAGGGTGGC GTGTGCTCCC     120

TGGCAAGCCT ATGACATGGC CGGGGCCTGC CTCTCTCTGC CTCTGACCCT CAGTGGCTCC     180

CATGAACTCC TTGCCCAATG GCATCTTTTT CCTGCGCTCC TTGGGTTATT CCAGTCTCCC     240

CTCAGCATTC CTTCCTCAGG GCCTCGCTCT TCTCTCTGCT CCCTCCTTGC ACAGCTGGCT     300

CTGTCCACCT CAGATGTCAC AGTGCTCTCT CAGAGGAGGA AGGCACCATG TACCCTCTGT     360

TTCCCAGGTA AGGGTTCAAT TTTTAAAAAT GGTTTTTTGT TTGTTTGTTT GTTTGTTTGT     420

TTGTTTGTTT TTCAAGACAG GGCTCCTCTG TGTAGTCCTA ACTGTCTTGA AACTCCCTCT     480

GTAGACCAGG TCGACCTCGA ACTCTTGAAA CCTGCCACGG ACCACCCAGT CAGGTATGGA     540

GGTCCCTGGA ATGAGCGTCC TCGAAGCTAG GTGGGTAAGG GTTCGGCGGT GACAAACAGA     600

AACAAACACA GAGGCAGTTT GAATCTGAGT GTATTTTGCA GCTCTCAAGC AGGGGATTTT     660

ATACATAAAA AAAAAAAAAA AAAAAAAACC AAACATTACA TCTCTTAGAA ACTATATCCA     720

ATGAAACAAT CACAGATACC AACCAAAACC ATTGGGCAGA GTAAAGCACA AAAATCATCC     780

AAGCATTACA ACTCTGAAAC CATGTATTCA GTGAATCACA AACAGAACAG GTAACATCAT     840

TATTAATATA AATCACCAAA ATATAACAAT TCTAAAAGGA TGTATCCAGT GGGGGCTGTC     900

GTCCAAGGCT AGTGGCAGAT TTCCAGGAGC AGGTTAGTAA ATCTTAACCA CTGAACTAAC     960

TCTCCAGCCC CATGGTCAAT TATTATTTAG CATCTAGTGC CTAATTTTTT TTTATAAATC    1020

TTCACTATGT AATTTAAAAC TATTTTAATT CTTCCTAATT AAGGCTTTCT TTACCATATA    1080

CCAAAATTCA CCTCCAATGA CACACGCGTA GCCATATGAA ATTTTATTGT TGGGAAAATT    1140

TGTACCTATC ATAATAGTTT TGTAAATGAT TTAAAAAGCA AAGTGTTAGC CGGGCGTGGT    1200

GGCACACGCC TTTAATCCCT GCACTCGGGA GGCAGGGCA GGAGGATTTC TGAGTTTGAG     1260

GCCAGCCTGG TCTACAGAGT GAGTTCCAGG ACAGCCAGGG CTACACAGAG AAACCCTGTC    1320

TCGAACCCCC CACCCCCCAA AAAAAGCAAA GTGTTGGTTT CCTTGGGGAT AAAGTCATGT    1380

TAGTGGCCCA TCTCTAGGCC CATCTCACCC ATTATTCTCG CTTAAGATCT TGGCCTAGGC    1440

TACCAGGAAC ATGTAAATAA GAAAAGGAAT AAGAGAAAAC AAAACAGAGA GATTGCCATG    1500

AGAACTACGG CTCAATATTT TTTCTCTCCG GCGAAGAGTT CCACAACCAT CTCCAGGAGG    1560

CCTCCACGTT TTGAGGTCAA TGGCCTCAGT CTGTGGAACT TGTCACACAG ATCTTACTGG    1620
```

```
AGGTGGTGTG GCAGAAACCC ATTCCTTTTA GTGTCTTGGG CTAAAAGTAA AAGGCCCAGA      1680

GGAGGCCTTT GCTCATCTGA CCATGCTGAC AAGGAACACG GGTGCCAGGA CAGAGGCTGG      1740

ACCCCAGGAA CACCTTAAAC ACTTCTTCCC TTCTCCGCCC CCTAGAGCAG GCTCCCCTCA      1800

CCAGCCTGGG CAGAAATGGG GGAAGATGGA GTGAAGCCAT ACTGGCTACT CCAGAATCAA      1860

CAGAGGGAGC CGGGGGCAAT ACTGGAGAAG CTGGTCTCCC CCCAGGGGCA ATCCTGGCAC      1920

CTCCCAGGCA GAAGAGGAAA CTTCCACAGT GCATCTCACT TCCATGAATC CCCTCCTCGG      1980

ACTCTGAGGT CCTTGGTCAC AGCTGAGGTG CAAAAGGCTC CTGTCATATT GTGTCCTGCT      2040

CTGGTCTGCC TTCCACAGCT TGGGGCCAC CTAGCCCACC TCTCCCTAGG GATGAGAGCA       2100

GCCACTACGG GTCTAGGCTG CCCATGTAAG GAGGCAAGGC CTGGGACAC CCGAGATGCC       2160

TGGTTATAAT TAACCCAGAC ATGTGGCTGC CCCCCCCCC CCAACACCTG CTGCCTGAGC       2220

CTCACCCCCA CCCCGGTGCC TGGGTCTTAG GCTCTGTACA CCATGGAGGA GAAGCTCGCT      2280

CTAAAAATAA CCCTGTCCCT GGTGGATCCA GGGTGAGGGG CAGGCTGAGG GCGGCCACTT      2340

CCCTCAGCCG CAGGTTTGTT TTCCCAAGAA TGGTTTTTCT GCTTCTGTAG CTTTTCCTGT      2400

CAATTCTGCC ATGGTGGAGC AGCCTGCACT GGGCTTCTGG GAGAAACCAA ACCGGGTTCT      2460

AACCTTTCAG CTACAGTTAT TGCCTTTCCT GTAGATGGGC GACTACAGCC CCACCCCCAC      2520

CCCCGTCTCC TGTATCCTTC CTGGGCCTGG GGATCCTAGG CTTTCACTGG AAATTTCCCC      2580

CCAGGTGCTG TAGGCTAGAG TCACGGCTCC CAAGAACAGT GCTTGCCTGG CATGCATGGT      2640

TCTGAACCTC CAACTGCAAA AAATGACACA TACCTTGACC CTTGGAAGGC TGAGGCAGGG      2700

GGATTGCCAT GAGTGCAAAG CCAGACTGGG TGGCATAGTT AGACCCTGTC TCAAAAAACC      2760

AAAAACAATT AAATAACTAA AGTCAGGCAA GTAATCCTAC TCGGGAGACT GAGGCAGAGG      2820

GATTGTTACA TGTCTGAGGC CAGCCTGGAC TACATAGGGT TTCAGGCTAG CCCTGTCTAC      2880

AGAGTAAGGC CCTATTTCAA AAACACAAAC AAAATGGTTC TCCCAGCTGC TAATGCTCAC      2940

CAGGCAATGA AGCCTGGTGA GCATTAGCAA TGAAGGCAAT GAAGGAGGGT GCTGGCTACA      3000

ATCAAGGCT TGGGGACTG AGGGCAGGCT GTAACAGGCT TGGGGGCCAG GGCTTATACG       3060

TGCCTGGGAC TCCCAAAGTA TTACTGTTCC ATGTTCCCGG CGAAGGGCCA GCTGTCCCCC      3120

GCCAGCTAGA CTCAGCACTT AGTTTAGGAA CCAGTGAGCA AGTCAGCCCT TGGGGCAGCC      3180

CATACAAGGC CATGGGGCTG GGCAAGCTGC ACGCCTGGGT CCGGGGTGGG CACGGTGCCC      3240

GGGCAACGAG CTGAAAGCTC ATCTGCTCTC AGGGGCCCCT CCCTGGGGAC AGCCCCTCCT      3300

GGCTAGTCAC ACCCTGTAGG CTCCTCTATA TAACCCAGGG GCACAGGGGC TGCCCCCGGG      3360

TCAC                                                                  3364

(2) INFORMATION FOR SEQ ID NO:10:

(i) SEQUENCE CHARACTERISTICS:
        (A) LENGTH: 174 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

GGTACCACTA CGGGTCTAGG CTGCCCATGT AAGGAGGCAA GGCCTGGGGA CACCCGAGAT        60

GCCTGGTTAT AATTAACCCC AACACCTGCT GCCCCCCCCC CCCCAACACC TGCTGCCTGA       120

GCCTGAGCGG TTACCCCACC CCGGTGCCTG GGTCTTAGGC TCTGTACACC ATGG            174
```

(2) INFORMATION FOR SEQ ID NO:11:

(i) SEQUENCE CHARACTERISTICS:
        (A) LENGTH: 699 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

```
AGATCTTCCT AGAAATTCGC TGTCTGCGAG GGCCGGCTGT TGGGGTGAGT ACTCCCTCTC      60

AAAAGCGGGC ATGACTTCTG CGCTAAGATT GTCAGTTTCC AAAAACGAGG AGGATTTGAT     120

ATTCACCTGG CCCGCGGTGA TGCCTTTGAG GGTGGCCGCG TCCATCTGGT CAGAAAAGAC     180

AATCTTTTTG TTGTCAAGCT TGAGGTGTGG CAGGCTTGAG ATCGATCTGG CCATACACTT     240

GAGTGACAAT GACATCCACT TTGCCTTTCT CTCCACAGGT GTCCACTCCC AGGTCCAACC     300

GCGGATCTCC CGGGACCATG CCCAAGAAGA AGAGGAAGGT GTCCAATTTA CTGACCGTAC     360

ACCAAAATTT GCCTGCATTA CCGGTCGATG CAACGAGTGA TGAGGTTCGC AAGAACCTGA     420

TGGACATGTT CAGGGATCGC CAGGCGTTTT CTGAGCATAC CTGGAAAATG CTTCTGTCCG     480

TTTGCCGGTC GTGGGCGGCA TGGTGCAAGT TGAATAACCG GAAATGGTTT CCCGCAGAAC     540

CTGAAGATGT TCGCGATTAT CTTCTATATC TTCAGGCGCG CGGTCTGGCA GTAAAAACTA     600

TCCAGCAACA TTTGGGCCAG CTAAACATGC TTCATCGTCG GTCCGGGCTG CCACGACCAA     660

GTGACAGCAA TGCTGTTTCA CTGGTTATGC GGCGGATCC                           699
```

(2) INFORMATION FOR SEQ ID NO:12:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

```
GAAGATCTAT AACTTCGTAT AATGTATGCT ATACGAAGTT ATTACCGAAG AAATGGCTCG      60

AGATCTTC                                                              68
```

(2) INFORMATION FOR SEQ ID NO:13:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

```
GAAGATCTCG AGCCATTTCT TCGGTAATAA CTTCGTATAG CATACATTAT ACGAAGTTAT      60

AGATCTTC                                                              68
```

(2) INFORMATION FOR SEQ ID NO:14:

(i) SEQUENCE CHARACTERISTICS:

-continued

```
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

CCACATGTAT AACTTCGTAT AGCATACATT ATACGAAGTT ATACATGTGG          50

(2) INFORMATION FOR SEQ ID NO:15:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

CCACATGTAT AACTTCGTAT AATGTATGCT ATACGAAGTT ATACATGTGG          50
```

ADENOVIRUS VECTORS

This is a Continuation of copending application Ser. No. 08/735,609 filed on Oct. 23, 1996.

FIELD OF THE INVENTION

The invention relates to improved adenovirus vectors, and more specifically, adenovirus vectors useful for gene therapy.

BACKGROUND

Adenoviruses (Ad) are double-stranded DNA viruses. The genome of adenoviruses (~36 kb) is complex and contains over 50 open reading frames (ORFs). These ORFs are overlapping and genes encoding one protein are often embedded within genes coding for other Ad proteins. Expression of Ad genes is divided into an early and a late phase. Early genes are those transcribed prior to replication of the genome while late genes are transcribed after replication. The early genes comprise E1a, E1b, E2a, E2b, E3 and E4. The E1a gene products are involved in transcriptional regulation; the E1b gene products are involved in the shut-off of host cell functions and mRNA transport. E2a encodes the a DNA-binding protein (DBP); E2b encodes the viral DNA polymerase and preterminal protein (pTP). The E3 gene products are not essential for viral growth in cell culture. The E4 region encodes regulatory protein involved in transcriptional and post-transcriptional regulation of viral gene expression; a subset of the E4 proteins are essential for viral growth. The products of the late genes (e.g., L1-5) are predominantly components of the virion as well as proteins involved in the assembly of virions. The VA genes produce VA RNAs which block the host cell from shutting down viral protein synthesis.

Adenoviruses or Ad vectors have been exploited for the delivery of foreign genes to cells for a number of reasons including the fact that Ad vectors have been shown to be highly effective for the transfer of genes into a wide variety of tissues in vivo and the fact that Ad infects both dividing and non-dividing cells; a number of tissues which are targets for gene therapy comprise largely non-dividing cells.

The current generation of Ad vectors suffer from a number of limitations which preclude their widespread clinical use including: 1) immune detection and elimination of cells infected with Ad vectors, 2) a limited carrying capacity (about 8.5 kb) for the insertion of foreign genes and regulatory elements, and 3) low-level expression of Ad genes in cells infected with recombinant Ad vectors (generally, the expression of Ad proteins is toxic to cells).

The latter problem was thought to be solved by using vectors containing deletions in the E1 region of the Ad genome (E1 gene products are required for viral gene expression and replication). However, even with such vectors, low-level expression of Ad genes is observed. It is now thought that most mammalian cells contain E1-like factors which can substitute for the missing Ad E1 proteins and permit expression of Ad genes remaining on the E1 deleted vectors.

What is needed is an approach that overcomes the problem of low level expression of Ad genes. Such an approach needs to ensure that adenovirus vectors are safe and non-immunogenic.

SUMMARY OF THE INVENTION

The present invention contemplates two approaches to improving adenovirus vectors. The first approach generally contemplates a recombinant plasmid, together with a helper adenovirus, in a packaging cell line. The helper adenovirus is rendered safe by utilization of loxP sequences. In the second approach, "damaged" adenoviruses are employed. While the "damaged" adenovirus is capable of self-propagation in a packaging cell line, it is not capable of expressing certain genes (e.g., the DNA polymerase gene and/or the adenovirus preterminal protein gene).

In one embodiment of the first approach, the present invention contemplates a recombinant plasmid, comprising in operable combination: a) a plasmid backbone, comprising an origin of replication, an antibiotic resistance gene and a eukaryotic promoter element; b) the left and right inverted terminal repeats (ITRs) of adenovirus, said ITRs each having a 5' and a 3' end and arranged in a tail to tail orientation on said plasmid backbone; c) the adenovirus packaging sequence, said packaging sequence having a 5' and a 3' end and linked to one of said ITRs; and d) a first gene of interest operably linked to said promoter element.

While it is not intended that the present invention be limited by the precise size of the plasmid, it is generally desirable that the recombinant plasmid have a total size of between 27 and 40 kilobase pairs. It is preferred that the total size of the DNA packaged into an EAM derived from these recombinant plasmids is about the length of the wild-type adenovirus genome (~36 kb). It is well known in the art that DNA representing about 105% of the wild-type length may be packaged into a viral particle; thus the EAM derived from recombinant plasmid may contain DNA whose length exceeds by ~105% the size of the wild-type genome. The size of the recombinant plasmid may be adjusted using reporter genes and genes of interest having various sizes (including the use of different sizes of introns within these genes) as well as through the use of irrelevant or non-coding DNA fragment which act as "stuffer" fragments (e.g., portions of bacteriophage genomes).

In one embodiment of the recombinant plasmid, said 5' end of said packaging sequence is linked to said 3' end of said left ITR. In this embodiment, said first gene of interest is linked to said 3' end of said packaging sequence. It is not intended that the present invention be limited by the nature of the gene of interest; a variety of genes (including both cDNA and genomic forms) are contemplated; any gene having therapeutic value may be inserted into the recombinant plasmids of the present invention. For example, the transfer of the adenosine deaminase (ADA) gene is useful for the treatment of ADA-patients; the transfer of the CFTR gene is useful for the treatment of cystitic fibrosis. A wide variety of diseases are known to be due to a defect in a single gene. The plasmids, vectors and EAMs of the present invention are useful for the transfer of a non-mutated form of a gene which is mutated in a patient thereby resulting in disease. The present invention is illustrated using recombinant plasmids capable of generating encapsidated adenovirus minichromosomes (EAMs) containing the dystrophin cDNA gene (the cDNA form of this gene is preferred due to the large size of this gene); the dystrophin gene is non-functional in muscular dystrophy (MD) patients. However, the present invention is not limited toward the use of the dystrophin gene for treatment of MD; the use of the utrophin (also called the dystrophin related protein) gene is also contemplated for gene therapy for the treatment of MD [Tinsley et al. (1993) Curr. Opin. Genet. Dev. 3:484 and (1992) Nature 360:591]; the utrophin gene protein has been reported to be capable of functionally substituting for the dystrophin gene [Tinsley and Davies (1993) Neuromusc. Disord. 3:539]. As the utrophin gene product is expressed in the muscle of muscular dystrophy patients, no immune response would be directed against the utrophin gene product expressed in cells of a host (including a human) containing the recombinant plasmids, Ad vectors or EAMs of the present invention. While the present invention is illustrated using plasmids containing the dystrophin gene, the plasmids, Ad vectors and EAMs of the present invention have broad application for the transfer of any gene whose gene product is missing or altered in activity in cells.

Embodiments are contemplated wherein the recombinant plasmid further comprises a second gene of interest. In one embodiment, said second gene of interest is linked to said 3' end of said right ITR. In one embodiment, said second gene of interest is a reporter gene. A variety of reporter genes are contemplated, including but not limited to E. coli β-galactosidase gene, the human placental alkaline phosphatase gene, the green fluorescent protein gene and the chloramphenicol acetyltransferase gene.

As mentioned above, the first approach also involves the use of a helper adenovirus in combination with the recombinant plasmid. In one embodiment, the present invention contemplates a helper adenovirus comprising i) first and a second loxP sequences, and ii) the adenovirus packaging sequence, said packaging sequence having a 5' and a 3' end. It is preferred that said first loxP sequence is linked to the 5' end of said packaging sequence and said second loxP sequence is linked to said 3' end of said packaging sequence. In one embodiment, the helper virus comprises at least one adenovirus gene coding region.

The present invention contemplates a mammalian cell line containing the above-described recombinant plasmid and the above-described helper virus. It is preferred that said cell line is a 293-derived cell line. Specifically, in one embodiment, the present invention contemplates a mammalian cell line, comprising: a) a recombinant plasmid, comprising, in operable combination: i) a plasmid backbone, comprising an origin of replication, an antibiotic resistance gene and a eukaryotic promoter element, ii) the left and right inverted terminal repeats (ITRs) of adenovirus, said ITRs each having a 5' and a 3' end and arranged in a tail to tail orientation on said plasmid backbone, iii) the adenovirus packaging sequence, said packaging sequence having a 5' and a 3' end and linked to one of said ITRs, and iv) a first gene of interest operably linked to said promoter element; and b) a helper adenovirus comprising i) first and a second loxP sequences, and ii) the adenovirus packaging sequence, said packaging sequence having a 5' and a 3' end. As noted previously, said helper can further comprise at least one adenovirus gene coding region.

Overall, the first approach allows for a method of producing an adenovirus minichromosome. In one embodiment, this method comprises: A) providing a mammalian cell line containing: a) a recombinant plasmid, comprising, in operable combination, i) a plasmid backbone, comprising an origin of replication, an antibiotic resistance gene and a eukaryotic promoter element, ii) the left and right inverted terminal repeats. (ITRs) of adenovirus, said ITRs each having a 5' and a 3' end and arranged in a tail to tail orientation on said plasmid backbone, iii) the adenovirus packaging sequence, said packaging sequence having a 5' and a 3' end and linked to one of the ITRs, and iv) a first gene of interest operably linked to said promoter element; and b) a helper adenovirus comprising i) first and a second loxP sequences, ii) at least one adenovirus gene coding region, and iii) the adenovirus packaging sequence, said packaging sequence having a 5' and a 3' end; and B) growing said cell line under conditions such that said adenovirus gene coding region is expressed and said recombinant plasmid directs the production of at least one adenoviral minichromosome. It is desired that said adenovirus minichromosome is encapsidated.

In one embodiment, the present invention contemplates recovering said encapsidated adenovirus minichromosome and, in turn, purifying said recovered encapsidated adenovirus minichromosome. Thereafter, said purified encapsidated adenovirus minichromosome can be administered to a host (e.g., a mammal). Human therapy is thereby contemplated.

It is not intended that the present invention be limited by the nature of the administration of said minichromosomes. All types of administration are contemplated, including direct injection (intramuscular, intravenous, subcutaneous, etc.), inhalation, etc.

As noted above, the present invention contemplates a second approaches to improving adenovirus vectors. In the second approach, "damaged" adenoviruses are employed. In one embodiment, the present invention contemplates a recombinant adenovirus comprising the adenovirus E2b region having a deletion, said adenovirus capable of self-propagation in a packaging cell line and said E2b region comprising the DNA polymerase gene and the adenovirus preterminal protein gene. In this embodiment, said deletion can be within the adenovirus DNA polymerase gene. Alternatively, said deletion is within the adenovirus preterminal protein gene. Finally, the present invention also contemplates embodiments wherein said deletion is within the adenovirus DNA polymerase and preterminal protein genes.

The present invention further provides cell lines capable of supporting the propagation of Ad virus containing deletions within the E2b region. In one embodiment the invention provides a mammalian cell line stably and constitutively expressing the adenovirus E1 gene products and the adenovirus DNA polymerase. In one embodiment, these cell lines comprise a recombinant adenovirus comprising a deletion within the E2b region, this E2b-deleted recombinant adenovirus being capable of self-propagation in the cell line. The present invention is not limited by the nature of the deletion within the E2b region. In one embodiment, the deletion is within the adenoviral DNA polymerase gene.

The present invention provides cells lines stably expressing E1 proteins and the adenoviral DNA polymerase, wherein the genome of the cell line contains a nucleotide sequence encoding adenovirus DNA polymerase operably linked to a heterologous promoter. In a particularly preferred embodiment, the cell line is selected from the group consisting of the B-6, B-9, C-1, C-4, C-7, C-13, and C-14 cell lines.

The present invention further provides cell lines which further constitutively express the adenovirus preterminal protein (pTP) gene product (in addition to E1 proteins and DNA polymerase). In one embodiment, these pTP-expressing cell lines comprise a recombinant adenovirus comprising a deletion within the E2b region, the recombinant adenovirus being capable of self-propagation in the pTP-expressing cell line. In a preferred embodiment, the deletion within the E2b region comprises a deletion within the adenoviral preterminal protein gene. In another preferred embodiment, the deletion within the E2b region comprises a deletion within the adenoviral (Ad) DNA polymerase and preterminal protein genes.

In a preferred embodiment, the cell lines coexpressing pTP and Ad DNA polymerase, contain within their genome, a nucleotide sequence encoding adenovirus preterminal protein operably linked to a heterologous promoter. In the invention is not limited by the nature of the heterologous promoter chosen. The art knows well how to select a suitable heterologous promoter to achieve expression in the desired host cell (e.g., 293 cells or derivative thereof). In a particularly preferred embodiment, the pTP- and Ad polymerase-expressing cell line is selected from the group consisting of the C-1, C-4, C-7, C-13, and C-14 cell lines.

The present invention provides a method of producing infectious recombinant adenovirus particles containing an adenoviral genome containing a deletion within the E2b region, comprising: a) providing: i) a mammalian cell line stably and constitutively expressing the adenovirus E1 gene products and the adenovirus DNA polymerase; ii) a recombinant adenovirus comprising a deletion within the E2b region, the recombinant adenovirus being capable of self-propagation in said cell line; b) introducing the recombinant adenovirus into the cell line under conditions such that the recombinant adenovirus is propagated to form infectious recombinant adenovirus particles; and c) recovering the infectious recombinant adenovirus particles. In a preferred embodiment, the method further comprises d) purifying the recovered infectious recombinant adenovirus particles. In yet another preferred embodiment, the method further comprises e) administering the purified recombinant adenovirus particles to a host which is preferably a mammal and most preferably a human.

In another preferred embodiment the mammalian cell line employed in the above method further constitutively expresses the adenovirus preterminal protein.

The present invention further provides a recombinant plasmid capable of replicating in a bacterial host comprising adenoviral E2b sequences, the E2b sequences containing a deletion within the polymerase gene, the deletion resulting in reduced polymerase activity. The present invention is not limited by the specific deletion employed to reduce polymerase activity. In a preferred embodiment, the deletion comprises a deletion of nucleotides 8772 to 9385 in SEQ ID NO:4. In one preferred embodiment, the recombinant plasmid has the designation pΔpol. In another preferred embodiment, the recombinant plasmid has the designation pBHG11Δpol.

The present invention also provides a recombinant plasmid capable of replicating in a bacterial host comprising adenoviral E2b sequences, the E2b sequences containing a deletion within the preterminal protein gene, the deletion resulting in the inability to express functional preterminal protein without disruption of the VA RNA genes. The present invention is not limited by the specific deletion employed to render the pTP inactive; any deletion within the pTP coding region which does not disrupt the ability to express the Ad VA RNA genes may be employed. In a preferred embodiment, the deletion comprises a deletion of nucleotides 10,705 to 11,134 in SEQ ID NO:4. In one preferred embodiment, the recombinant plasmid has the designation pΔpTP. In another preferred embodiment, the recombinant plasmid has the designation pBHG11ΔpTP.

In a preferred embodiment, the recombinant plasmid containing a deletion with the pTP region further comprises a deletion within the polymerase gene, this deletion resulting in reduced (preferably absent) polymerase activity. The present invention is not limited by the specific deletion employed to inactivate the polymerase and pTP genes. In a preferred embodiment, the deletion comprises a deletion of nucleotides 8,773 to 9586 and 11,067 to 12,513 in SEQ ID NO:4. In one preferred embodiment, the recombinant plasmid has the designation pAXBΔpolΔpTPVARNA+t13. In another preferred embodiment, the recombinant plasmid has the designation pBHG11ΔpolΔpTPVARNA+t13.

BRIEF DESCRIPTION OF THE FIGURES

FIG. 1A is a schematic representation of the Ad polymerase expression plasmid pRSV-pol indicating that the Ad2 DNA polymerase sequences are under the transcriptional control of the RSV-LTR/promoter element and are flanked on the 3' end by the SV-40 small t intron and SV-40 polyadenylation addition site.

FIG. 1B is a schematic representation of the expression plasmid pRSV-pTP indicating that the Ad2 preterminal protein sequences are under the transcriptional control of the RSV-LTR/promoter element and are flanked on the 3' end by the SV40 small-t intron and SV-40 polyadenylation signals.

FIGS. 15A–B are western blot (immunoblot) analyses of protein extracts from mdx myoblasts and myotubes demonstrating the expression of β-galactosidase (A) and dystrophin (B) in cells infected with Ad5βdys EAMs.

DEFINITIONS

Figure 2:
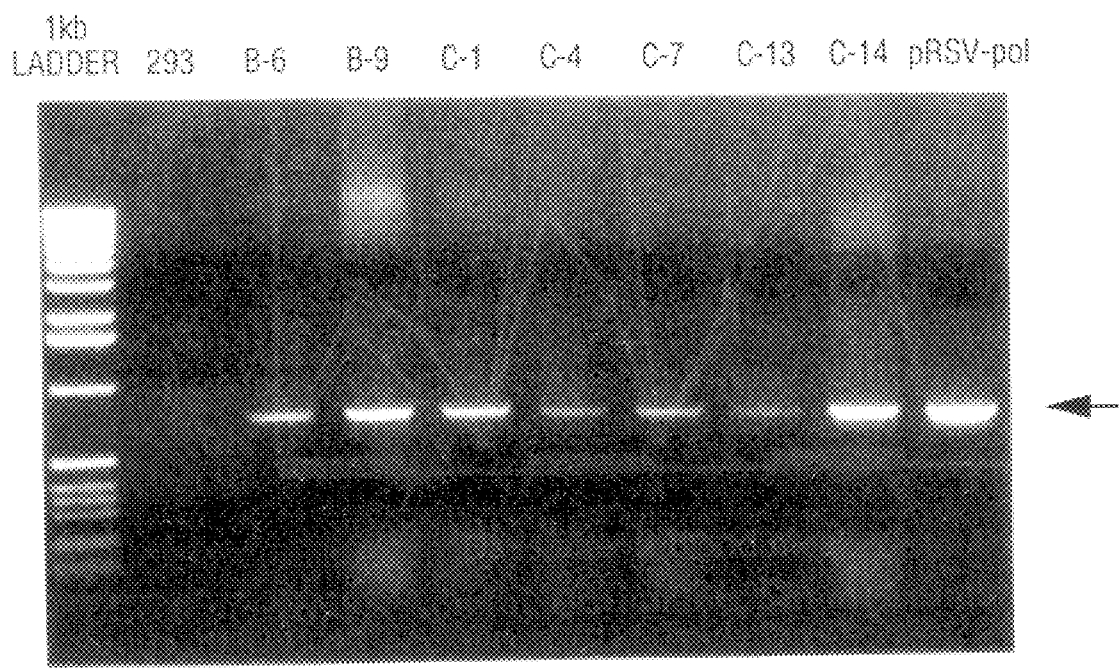
FIG. 2 is an ethidium bromide-stained gel depicting the presence of Ad pol DNA sequences in genomic DNA from LP-293 cells and several hygromycin-resistant cell lines. The ~750 bp PCR products are indicated by the arrow.

To facilitate understanding of the invention, a number of terms are defined below.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained. The term "gene" encompasses both cDNA and genomic forms of a given gene.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eucaryotes comprise "promoter" and "enhancer" elements. Promoters and enhancers consist of short arrays of DNA sequences that interact specifically with cellular proteins involved in transcription [Maniatis, T. et al., Science 236:1237 (1987)]. Promoter and enhancer elements have been isolated from a variety of eukaryotic sources including genes in yeast, insect and mammalian cells and viruses (analogous control elements, i.e., promoters, are also found in procaryotes). The selection of a particular promoter and enhancer depends on what cell type is to be used to express the protein of interest. Some eukaryotic promoters and enhancers have a broad host range while others are functional in a limited subset of cell types [for review see Voss, S. D. et al., Trends Biochem. Sci., 11:287 (1986) and Maniatis, T. et al., supra (1987)].

The term "recombinant DNA vector" as used herein refers to DNA sequences containing a desired coding sequence and appropriate DNA sequences necessary for the expression of the operably linked coding sequence in a particular host organism (e.g. mammal). DNA sequences necessary for expression in procaryotes include a promoter, optionally an operator sequence, a ribosome binding site and possibly other sequences. Eukaryotic cells are known to utilize promoters, polyadenlyation signals and enhancers.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "genetic cassette" as used herein refers to a fragment or segment of DNA containing a particular grouping of genetic elements. The cassette can be removed and inserted into a vector or plasmid as a single unit. A plasmid backbone refers to a piece of DNA containing at least plasmid origin of replication and a selectable marker gene (e.g., an antibiotic resistance gene) which allows for selection of bacterial hosts containing the plasmid; the plasmid backbone may also include a polylinker region to facilitate the insertion of genetic elements within the plasmid. When a particular plasmid is modified to contain non-plasmid elements (e.g., insertion of Ad sequences and/or a eukaryotic gene of interest linked to a promoter element), the plasmid sequences are referred to as the plasmid backbone.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad Sci. USA* 46:461 (1960) have been followed by the refinement of this process into an essential tool of modem biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template"are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, viruses, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery). Adenoviruses, as noted above, are double-stranded DNA viruses. The left and right inverted terminal repeats (ITRs) are short elements located at the 5' and 3' termini of the linear Ad genome, respectively and are required for replication of the viral DNA. The left ITR is located between 1–130 bp in the Ad genome (also referred to as 0–0.5 mu). The right ITR is located from ~3,7500 bp to the end of the genome (also referred to as 99.5–100 mu). The two ITRs are inverted repeats of each other. For clarity, the left ITR or 5' end is used define the 5' and 3' ends of the ITRs. The 5' end of the left ITR is located at the extreme 5' end of the linear adenoviral genome; picturing the left ITR (LITR) as an arrow extending from the 5' end of the genome, the tail of the 5' ITR is located at mu 0 and the head of the left ITR is located at ~0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at ~mu 99.5; the head of the right ITR is referred to as the 5' end of the right ITR and the tail of the right ITR is referred to as the 3' end of the right ITR (RITR). In the linear Ad genome, the ITRs face each other with the head of each ITR pointing inward toward the bulk of the genome. When arranged in a "tail to tail orientation" the tails of each ITR (which comprise the 5' end of the LITR and the 3' end of the RITR) are located in proximity to one another while the heads of each ITR are separated and face outward (see for example, the arrangement of the ITRs in the EAM shown in FIG. 10 herein). The "adenovirus packaging sequence" refers to the Ψ sequence which comprises five (AI–AV) packaging signals and is required for encapsidation of the mature linear genome; the packaging signals are located from ~194 to 358 bp in the Ad genome (about 0.5–1.0 mu).

The phrase "at least one adenovirus gene coding region" refers to a nucleotide sequence containing more than one adenovirus gene coding gene. A "helper adenovirus" or "helper virus" refers to an adenovirus which is replication-competent in a particular host cell (the host may provide Ad gene products such as E1 proteins), this replication-competent virus is used to supply in trans functions (e.g., proteins) which are lacking in a second replication-incompetent virus; the first replication-competent virus is said to "help" the second replication-incompetent virus thereby permitting the propagation of the second viral genome in the cell containing the helper and second viruses.

The term "containing a deletion within the E2b region" refers to a deletion of at least one basepair (preferably more than one bp and preferably at least 100 and most preferably more than 300 bp) within the E2b region of the adenovirus genome. An E2b deletion is a deletion that prevents expression of at least one E2b gene product and encompasses deletions within exons encoding portions of E2b-specific proteins as well as deletions within promoter and leader sequences.

An "adenovirus minichromosome" refers to a linear molecule of DNA containing the Ad ITRs on each end which is generated from a plasmid containing the ITRs and one or more gene of interest. The term "encapsidated adenovirus minichromosome" or "EAM" refers to an adenovirus minichromosome which has been packaged or encapsidated into a viral particle; plasmids containing the Ad ITRs and the packaging signal are shown herein to produce EAMs. When used herein, "recovering" encapsidated adenovirus minichromosomes refers to the collection of EAMs from a cell containing an EAM plasmid and a helper virus; this cell will direct the encapsidation of the minichromosome to produce EAMs. The EAMs may be recovered from these cells by lysis of the cell (e.g., freeze-thawing) and pelleting of the cell debris to a cell extract as described in Example 1 (Ex. 1 describes the recovery of Ad virus from a cell, but the same technique is used to recover EAMs from a cell). "Purifying" such minichromosomes refers to the isolation of the recovered EAMs in a more concentrated form (relative to the cell lysate) on a density gradient as described in Example 7; purification of recovered EAMs permits the physical separation of the EAM from any helper virus (if present).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

As used herein, the term "gene of interest" refers to a gene inserted into a vector or plasmid whose expression is desired in a host cell. Genes of interest include genes having therapeutic value as well as reporter genes. A variety of such genes are contemplated, including genes of interest encoding a protein which provides a therapeutic function (such as the dystrophin gene, which is capable of correcting the defect seen in the muscle of MD patients), the utrophin gene, the CFTR gene (capable of correcting the defect seen in cystitic fibrosis patients), etc.

The term "reporter gene" indicates a gene sequence that encodes a reporter molecule (including an enzyme). A "reporter molecule" is detectable in any detection system, including, but not limited to enzyme (e.g., ELISA, as well as enzyme-based histochemical assays), fluorescent, radioactive, and luminescent systems. In one embodiment, the present invention contemplates the *E. coli* β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene; other reporter genes are known to the art and may be employed.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DESCRIPTION OF THE INVENTION

The present invention provides improved adenovirus vectors for the delivery of recombinant genes to cells in vitro and in vivo. As noted above, the present invention contemplates two approaches to improving adenovirus vectors. The first approach generally contemplates a recombinant plasmid containing the minimal region of the Ad genome required for replication and packaging (i.e., the left and right ITR and the packaging or Ψ sequence) along with one or more genes of interest; this recombinant plasmid is packaged into an encapsidated adenovirus minichromosome (EAM) when grown in parallel with an E1-deleted helper virus in a cell line expressing the E1 proteins (e.g., 293 cells). The recombinant adenoviral minichromosome is preferentially packaged. To prevent the packaging of the helper virus, a helper virus containing loxP sequences flanking the Ψ sequence is employed in conjunction with 293 cells expressing Cre recombinase; Cre-loxP mediated recombination removes the packaging sequence from the helper genome thereby preventing packaging of the helper during the production of EAMs. In the second approach, "damaged" or "deleted" adenoviruses containing deletions within the E2b region are employed. While the "damaged" adenovirus is capable of self-propagation in a packaging cell line expressing the appropriate E2b protein(s), the E2b-deleted recombinant adenovirus are incapable of replicating and expressing late viral gene products outside of the packaging cell line.

In one embodiment, the self-propagating recombinant adenoviruses contain deletions in the E2b region of the adenovirus genome. In another embodiment, "gutted" viruses are contemplated; these viruses lack all viral coding regions. In addition, packaging cell lines co-expressing E1 and E2b gene products are provided which allow the production of infectious recombinant virus containing deletions in the E1 and E2b regions without the use of helper virus.

The Description of the Invention is divided into the following sections: I. Self-Propagating Adenovirus Vectors; II. Packaging Cell Lines; and III. Encapsidated Adenoviral Minichromosomes.

I. Self-Propagating Adenovirus Vectors

Self-propagating adenovirus (Ad) vectors have been extensively utilized to deliver foreign genes to a great variety of cell types in vitro and in vivo. "Self-propagating viruses" are those which can be produced by transfection of a single piece of DNA (the recombinant viral genome) into a single packaging cell line to produce infectious virus; self-propagating viruses do not require the use of helper virus for propagation.

Existing Ad vectors have been shown to be problematic in vivo. This is due in part because current or first generation Ad vectors are deleted for only the early region 1 (E1) genes. These vectors are crippled in their ability to replicate normally without the trans-complementation of E1 functions provided by human 293 cells, a packaging cell line [ATCC CRL 1573; Graham et al. (1977) J. Gen. Virol. 36:59]. Unfortunately, with the use of high titres of E1 deleted vectors, and the fact that there are E1-like factors present in many cell types, E1 deleted vectors can overcome the block to replication and express other viral gene products [Imperiale et al. (1984) Mol. Cell Biol. 4:867; Nevins (1981) Cell 26:213; and Gaynor and Berk (1983) Cell 33:683]. The expression of viral proteins in the infected target cells elicits a swift host immune response, that is largely T-cell mediated [Yang and Wilson (1995) J. Immunol. 155:2564 and Yang et al. (1994) Proc. Natl. Acad. Sci. U.S.A. 91:4407]. The transduced cells are subsequently eliminated, along with the transferred foreign gene. In inmmuno-incompetent animals, Ad delivered genes can be expressed for periods of up to one year [Yang et al. (1994), supra; Vincent et al. (1993) Nature Genetics 5:130; and Yang et al. (1995) Proc. Natl. Acad. Sci. U.S.A. 92:7257].

Another shortcoming of first generation Ad vectors is that a single recombination event between the genome of an Ad vector and the integrated E1 sequences present in 293 cells can generate replication competent Ad (RCA), which can readily contaminate viral stocks.

In order to further cripple viral protein expression, and also to decrease the frequency of generating RCA, the present invention provides Ad vectors containing deletions in the E2b region. Propagation of these E2b-deleted Ad vectors requires cell lines which express the deleted E2b gene products. The present invention provides such packaging cell lines and for the first time demonstrates that the E2b gene products, DNA polymerase and preterminal protein, can be constitutively expressed in 293 cells along with the E1 gene products. With every gene that can be constitutively expressed in 293 cells comes the opportunity to generate new versions of Ad vectors deleted for the respective genes. This has immediate benefits; increased carrying capacity, since the combined coding sequences of the polymerase and preterminal proteins that can be theoretically deleted approaches 4.6 kb and a decreased incidence of RCA generation, since two or more independent recombination events would be required to generate RCA. Therefore, the novel E1, Ad polymerase and preterminal protein expressing cell lines of the present invention enable the propagation of Ad vectors with a carrying capacity approaching 13 kb, without the need for a contaminating helper virus [Mitani et al. (1995) Proc. Natl. Acad. Sci. U.S.A. 92:3854]. In addition, when genes critical to the viral life cycle are deleted (e.g., the E2b genes), a further crippling of Ad to replicate and express other viral gene proteins occurs. This decreases immune recognition of virally infected cells, and allows for extended durations of foreign gene expression. The most important attribute of E1, polymerase, and preterminal protein deleted vectors, however, is their inability to express the respective proteins, as well as a predicted lack of expression of most of the viral structural proteins. For example, the major late promoter (MLP) of Ad is responsible for transcription of the late structural proteins L1 through L5 [Doerfler, In *Adenovirus DNA, The Viral Genome and Its Expression* (Martinus Nijhoff Publishing Boston, 1986)]. Though the MLP is minimally active prior to Ad genome replication, the rest of the late genes get transcribed and translated from the MLP only after viral genome replication has occurred [Thomas and Mathews (1980) Cell 22:523]. This cis-dependent activation of late gene transcription is a feature of DNA viruses in general, such as in the growth of polyoma and SV-40. The polymerase and preterminal proteins are absolutely required for Ad replication (unlike the E4 or protein IX proteins) and thus their deletion is extremely detrimental to Ad vector late gene expression.

II. Packaging Cell Lines Constitutively Expressing E2b Gene Products

The present invention addresses the limitations of current or first generation Ad vectors by isolating novel 293 cell lines coexpressing critical viral gene functions. The present invention describes the isolation and characterization of 293 cell lines capable of constitutively expressing the Ad polymerase protein. In addition, the present invention describes the isolation of 293 cells which not only express the E1 and polymerase proteins, but also the Ad-preterminal protein. The isolation of cell lines coexpressing the E1, Ad polymerase and preterminal proteins demonstrates that three genes critical to the life cycle of Ad can be constitutively coexpressed, without toxicity.

In order to delete critical genes from self-propagating Ad vectors, the proteins encoded by the targeted genes have to first be coexpressed in 293 cells along with the E1 proteins. Therefore, only those proteins which are non-toxic when coexpressed constitutively (or toxic proteins inducibly-expressed) can be utilized. Coexpression in 293 cells of the E1 and E4 genes has been demonstrated (utilizing inducible, not constitutive, promoters) [Yeh et al (1996) J. Virol. 70:559; Wang et al. (1995) Gene Therapy 2:775; and Gorziglia et al. (1996) J. Virol. 70:4173]. The E1 and protein IX genes (a virion structural protein) have been coexpressed [Caravokyri and Leppard (1995) J. Virol. 69:6627], and coexpression of the E1, E4, and protein IX genes has also been described [Krougliak and Graham (1995) Hum. Gene Ther. 6:1575].

The present invention provides for the first time, cell lines coexpressing E1 and E2b gene products. The E2b region encodes the viral replication proteins which are absolutely required for Ad genome replication [Doerfler, supra and Pronk et al. (1992) Chromosoma 102:S39–S45]. The present invention provides 293 cells which constitutively express the 140 kD Ad-polymerase. While other researchers have reported the isolation of 293 cells which express the Ad-preterminal protein utilizing an inducible promoter [Schaack et al. (1995) J. Virol. 69:4079], the present invention is the first to demonstrate the high-level, constitutive coexpression of the E1, polymerase, and preterminal proteins in 293 cells, without toxicity. These novel cell lines permit the propagation of novel Ad vectors deleted for the E1, polymerase, and preterminal proteins.

III. Encapsidated Adenoviral Minichromosomes

The present invention also provides encapsidated adenovirus minichromosome (EAM) consisting of an infectious encapsidated linear genome containing Ad origins of replication, packaging signal elements, a reporter gene (e.g., a β-galactosidase reporter gene cassette) and a gene of interest (e.g., a full length (14 kb) dystrophin cDNA regulated by a muscle specific enhancer/promoter). EAMs are generated by cotransfecting 293 cells with supercoiled plasmid DNA (e.g., pAd5βdys) containing an embedded inverted origin of replication (and the remaining above elements) together with linear DNA from E1-deleted virions expressing human placental alkaline phosphatase (hpAP) (a helper virus). All proteins necessary for the generation of EAMs are provided in trans from the hpAP virions and the two can be separated from each other on equilibrium CsCl gradients. These EAMs are useful for gene transfer to a variety of cell types both in vitro and in vivo.

Adenovirus-mediated gene transfer to muscle is a promising technology for gene therapy of Duchenne muscular dystrophy (DMD). However, currently available recombinant adenovirus vectors have several limitations, including a limited cloning capacity of 8.5 kb, and the induction of a host immune response that leads to transient gene expression of 3 to 4 weeks in immunocompetent animals. Gene therapy for DMD could benefit from the development of adenoviral vectors with an increased cloning capacity to accommodate a full length (~14 kb) dystrophin cDNA. This increased capacity should also accommodate gene regulatory elements to achieve expression of transduced genes in a tissue-specific manner. Additional vector modifications that eliminate adenoviral genes, expression of which is associated with development of a host immune response, might greatly increase long term expression of virally delivered genes in vivo. The constructed encapsidated adenovirus minichromosomes of the present invention are capable of delivering up to 35 kb of non-viral exogenous DNA. These minichromosomes are derived from bacterial plasmids containing two fused inverted adenovirus origins of replication embedded in a circular genome, the adenovirus packaging signals, a βgalactosidase reporter gene and a full length dystrophin cDNA regulated by a muscle specific enhancer/promoter. The encapsidated minichromosomes are propagated in vitro by trans-complementation with a replication defective (E1+ E3 deleted) helper virus. These minichromosomes can be propagated to high titer (>10$^8$/ml) and purified on CsCl gradients due to their buoyancy difference relative to helper virus. These vectors are able to transduce myogenic cell cultures and express dystrophin in myotubes. These results demonstrate that encapsidated adenovirus minichromosomes are useful for gene transfer to muscle and other tissues.

The present invention further provides methods for modifying the above-described EAM system to enable the generation of high titer stocks of EAMs with minimal helper virus contamination. Preferably the EAM stocks contain helper virus representing less than 1%, preferably less than 0.1% and most preferably less than 0.01% (including 0.0%) of the final viral isolate.

The amount of helper virus present in the EAM preparations is reduced in two ways. The first is by selectively controlling the relative packaging efficiency of the helper virus versus the EAM virus. The Cre-loxP excision method is employed to remove the packaging signals from the helper virus thereby preventing the packaging of the helper virus used to provide in trans viral proteins for the encapsidation of the recombinant adenovirus minichromosomes. The second approach to reducing or eliminating helper virus in EAM stocks is the use of improved physical methods for separating EAM from helper virus.

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); mol (moles); mmol (millimoles); μmol (micromoles); nmol (nanomoles); mu or m.u. (map unit); g (gravity); gm (grams); mg (milligrams); μg (micrograms); pg (picograms); L (liters); ml (milliliters); μl (microliters); cm (centimeters); mm (millimeters); μm (micrometers); nm (nanometers); hr (hour); min (minute); msec (millisecond); °C (degrees Centigrade); AMP (adenosine 5'-monophosphate); cDNA (copy or complimentary DNA); DTT (dithiotheritol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl] piperazine-N-[2-ethanesulfonic acid]); HBS (HEPES buffered saline); SDS (sodium dodecyl sulfate); Tris-HCl (tris [Hydroxymethyl]aminomethanehydrochloride); rpm (revolutions per minute); ligation buffer (50 mM Tris-HCl, 10 mM MgCl$_2$, 10 mM dithiothreitol, 25 μg/ml bovine serum albumin, and 26 μM NAD+, and pH 7.8); EGTA (ethylene glycol-bis(β-aminoethyl ether) N, N, N', N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DMEM (Dulbecco's modified Eagle's medium); ABI (Applied Biosystems Inc., Foster City, Calif.); Amersham (Amersham Corporation, Arlington Heights, Ill.); ATCC (American Type Culture Collection, Rockville, Md.); Beckman (Beckman Instruments Inc., Fullerton Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); CRI (Collaborative Research Inc. Bedford, Me.); Eastman Kodak (Eastman Kodak Co., Rochester, N.Y.); Eppendorf (Eppendorf, Eppendorf North America, Inc., Madison, Wis.); Falcon (Becton Dickenson Labware, Lincoln Park, N.J.); IBI (International Biotechnologies, Inc., New Haven, Conn.); ICN (ICN Biomedicals, Inc., Costa Mesa, Calif.); Invitrogen (Invitrogen, San Diego, Calif.); New Brunswick (New Brunswick Scientific Co. Inc., Edison, N.J.); NEB (New England BioLabs Inc., Beverly, Me.); NEN (Du Pont NEN Products, Boston, Mass.); Pharmacia (Pharmacia LKB Gaithersburg, Md.); Promega (Promega Corporation, Madison, Wis.); Stratagene (Stratagene Cloning Systems, La Jolla, Calif.); UVP (UVP, Inc., San Gabreil, Calif.); USB (United States Biochemical Corp., Cleveland, Ohio); and Whatman (Whatman Lab. Products Inc, Clifton, N.J.).

Unless otherwise indicated, all restriction enzymes and DNA modifying enzymes were obtained from New England Biolabs (NEB) and used according to the manufacturers directions.

EXAMPLE 1

Generation of Packaging Cell Lines that Coexpress the Adenovirus E1 and DNA Polymerase Proteins In this example, packaging cell lines coexpressing Ad E1 and polymerase proteins were described. These cell lines were shown to support the replication and growth of H5ts36, an Ad with a temperature-sensitive mutation of the Ad polymerase protein. These polymerase-expressing packaging cell lines can be used to prepare Ad vectors deleted for the E1 and polymerase functions.

a) Tissue Culture and Virus Growth

LP-293 cells (Microbix Biosystems, Toronto) were grown and serially passaged as suggested by the supplier.

Plaque assays were performed in 60 mm dishes containing cell monolayers at ~90% confluency. The appropriate virus dilution in a 2% DMEM solution was dripped onto the cells, and the plates incubated at the appropriate temperature for one hour. The virus containing media was aspirated, the monolayer was overlaid with 10 mls of a pre-warmed EMEM agar overlay solution (0.8% Noble agar, 4% fetal calf serum, and antibiotics) and allowed to solidify. After the appropriate incubation time (usually 7 days for incubations at 38.5° C. and 10–12 days for incubations at 32° C.), five mls of the agar-containing solution containing 1.3% neutral red was overlaid onto the infected dishes and plaques were counted the next day. An aliquot of the virus H5ts36 [Freimuth and Ginsberg (1986) Proc. Natl. Acad. Sci. U.S.A. 83:7816] was utilized to produce high titre stocks after infection of 293 cells at 32° C. H5ts36 is an Ad5-derived virus defective for viral replication at the nonpermissive temperature [Miller and Williams (1987) J. Virol. 61:3630].

The infected cells were harvested after the onset of extensive cytopathic effect, pelleted by centrifugation and resuspended in 10 mM Tris-Cl, pH 8.0. The lysate was freeze-thawed three times and centrifuged to remove the cell debris. The cleared lysate was applied to $CsCl_2$ step gradients (heavy CsCl at density of 1.45 g/ml, the light CsCl at density of 1.20 g/ml), ultracentrifuged, and purified using standard techniques [Graham and Prevec (1991) In *Methods in Molecular Biology*, Vol 7. *Gene Transfer and Expression Protocols*, Murray (ed.), Humana Press, Clifton, N.J., pp. 109–128]. The concentration of plaque forming units (pfu) of this stock was determined at 32° C. as described above. Virion DNA was extracted from the high titre stock by pronase digestion, phenol-chloroform extraction, and ethanol precipitation. The leakiness of this stock was found to be <1 in 2000 pfu at the non-permissive temperature, consistent with previous reports [Miller and Williams (1987), supra].

b) Plasmids

The expression plasmid pRSV-pol [Zhao and Padmanabhan (1988) Cell 55:1005] contains sequences encoding the Ad2 polymerase mRNA (including the start codon from the exon at map unit 39) under the transcriptional control of the Rous Sarcoma Virus LTR/promoter element; the Ad2 DNA polymerase sequences are flanked on the 3' end by the SVA40 small t intron and SV40 polyadenylation addition site (see FIG. 1A). FIG. 1A provides a schematic representation of the Ad polymerase expression plasmid pRSV-pol. pRSV-pol includes the initiator methionine and amino-terminal peptides encoded by the exon at m.u. 39 of the Ad genome. The location of the PCR primers p602a and p2158c, the two ScaI 1 kb probes utilized for Northern analyses, the polymerase terminator codon, and the polyadenylation site of the IVa2 gene (at 11.2 m.u. of the Ad genome) are indicated.

The expression plasmid pRSV-pTP [Zhao and Padmanabhan (1988), supra) contains sequences encoding the Ad2 preterminal protein (including the amino terminal peptides encoded by the exon at map unit 39 of the As genome) under the transcriptional control of the Rous Sarcoma Virus LTR/promoter element; the pTP sequences are flanked on the 3' end by the SV40 small-t intron and SV-40 polyadenylation signals (see FIG. 1B for a schematic of pRSV-PTP). FIG. 1B also shows the location of the EcoRV subfragment utilized as a probe in the genomic DNA and cellular RNA evaluations, as well as the initiator methionine codon present from map unit 39 in the Ad5 genome. The locations of the H5in190 and H5sub100 insertions are shown relative to the preterminal protein open-reading frame. The following abbreviations are used in FIG. 1: ORF, open reading frame; small-t, small tumor antigen. and m.u., map unit.

pCEP4 is a plasmid containing a hygromycin expression cassette (Invitrogen).

pFG140 (Microbix Biosystems Inc. Toronto, Ontario) is a plasmid containing sequences derived from Ad5dl309 which contain a deletion/substitution in the E3 region [Jones and Shek (1979) Cell 17:683]. pFG140 is infectious in single transfections of 293 cells and is used as a control for transfection efficiency.

c) Transfection of 293 Cells

LP-293 cells were cotransfected with BamHI linearized pRSV-pol and BamHI linearized pCEP4 at a molar ratio of 10:1 using a standard $CaPO_4$ precipitation method [Sambrook et al. (1989) Molecular Cloning: A Laboratory Manual, Cold Spring Harbor Press, Plainview, N.Y., pp.16.33–16.36]. In addition, 293 cells were cotransfected with or with BamHI linearized pRSV-pol, BamHI linearized pRSV-pTP and pCEP using a molar ratio of 10:1 (non-selectable:selectable plasmids).

Forty-eight hours after transfection, the cells were passaged into media containing hygromycin at 100 μg/mL. Individual hygromycin resistant colonies were isolated and expanded.

d) Isolation of Ad Polymerase Expressing 293 Cell Lines

Twenty hygromycin resistant cell lines were expanded and screened for the ability to express the Ad polymerase protein. Initially, the individual cell lines were assayed for the ability to support growth of the viral polymerase mutant H5ts36 using the plaque assay described in section a) above. It was speculated that constitutive expression of the wild type Ad polymerase protein in a clonal population of 293 cells should allow the growth of H5ts36 at 38.5° C. However, it was unclear if constitutive expression of the Ad polymerase would be toxic when coexpressed with the E1 proteins present in 293 cells. Similar toxicity problems have been observed with the Ad ssDBP, and the pTP [Klessig et al. (1984) Mol. Cell. Biol. 4:1354 and Schaack et al. (1995) J. Virol. 69:4079].

Of the twenty hygromycin resistant cell lines isolated, seven were able to support plaque formation with H5ts36 at the non-permissive temperature, unlike the parental LP-293 cells; these cell lines were named B-6, B-9, C-1, C-4, C-7, C-13 and C-14 (see Table 1) (the B-6 and B-9 cell lines received only the pRSV-pol and CEP4 plasmids; C-1, C-4, C-7, C-13 and C-14 cell lines received the pRSV-pol, pRSV-pTP and CEP4 plasmids). For the results shown in Table 1, dishes (60 mm) of near confluent cells of each cell line were infected with the same dilution of H5ts36 at the temperature indicated, overlaid with agar media, and stained for plaques as outlined in section a. Passage number refers to the number of serial passages after initial transfection with the plasmid pRSV-pol.

The cell line B-6 produced plaques one day earlier than the other Ad polymerase-expressing cell lines, which may reflect increased polymerase expression (see below). Cell line B-9 demonstrated an increased doubling time whereas each of the other cell lines displayed no growth disadvantages relative to the parental LP-293 cells. As shown in Table 1, even after multiple passages (in some instances up to four months of serial passaging) the cells were still capable of H5ts36 plaque formation at the non-permissive temperature, indicating that the RSV-LTR/promoter remained active for extended periods of time. However, the cell lines B-9 and C-13 displayed a decreased ability to plaque the virus at 32° C. as well as at 38.5° C., suggesting that a global viral complementation defect had occurred in these cell lines after extended passaging. The remaining cell lines screened at later passages demonstrated no such defect, even after 20 passages (e.g., cell line B-6, Table 1).

TABLE I

Plaquing Ability Of H5ts36 At The Non-Permissive Temperature Utilizing 293-Ad Polymerase Expressing Cell Lines

| Cell Line | Passage Number | Number Of Plaques At: | |
|---|---|---|---|
| | | 32.0° C. | 38.5° C. |
| 293 | — | >500 | 0 |
| B-6 | 9 | >500 | >500 |
| | 20 | >500 | >500 |
| B-9 | 5 | >500 | >500 |
| | 14 | 90 | 18 |
| C-1 | 5 | >500 | >500 |
| | 13 | >500 | >500 |
| C-4 | 5 | >500 | >500 |
| | 14 | >500 | >500 |
| C-7 | 5 | >500 | >500 |
| | 14 | >500 | >500 |
| C-13 | 5 | >500 | >500 |
| | 27 | 120 | 4 |
| C-14 | 5 | >500 | >500 |
| | 27 | >500 | 370 | e) Genomic Analysis of Ad Polymerase-Expressing Cell Lines

Genomic DNA from LP-293 cells and each of the seven cell lines able to complement H5ts36 at 38.5° C. were analyzed by PCR for the presence of pRSV-pol derived sequences. Genomic DNA from LP-293 cells and the hygromycin resistant cell lines were harvested using standard protocols (Sambrook et al., supra) and 200 ng of DNA from each cell line was analyzed by PCR in a solution containing 2 ng/mL of primers p602a and p2158c, 10 mM Tris'HCl, pH 8.3, 50 mM KCl, 1.5 mM $MgCl_2$, and 0.001% gelatin. The forward primer, p602a [5'-TTCATTTTATGTTTCAGGTTCAGGG-3' (SEQ ID NO:2)] is located in the SV-40 polyadenylation sequence. The reverse primer p2158c [5'-TTACCGCCACACTCGCAGGG-3' (SEQ ID NO:3)] is Ad-sequence specific with the 5' nucleotide located at position 3394 of the Ad 5 genome [numbering according to Doerfler (1986) *Adenovirus DNA, The Viral Genome and Its Expression*, Nijhoff, Boston, Me., pp. 1–95].

PCR was performed with a Perkin Elmer 9600 Thermocycler utilizing the following cycling parameters: initial-denaturation at 94° C. for 3 min, 3 cycles of denaturation at 94° C. for 30 sec, annealing at 50° C. for 30 sec, and extension at 72° C. for 60 sec, followed by another 27 cycles with an increased annealing temperature at 56° C., with a final extension at 72° C. for 10 minutes. PCR products were separated on a 1.0 % agarose gel and visualized with ethidium bromide staining (FIG. 2). A 1 kb ladder (Gibco-BRL) was used as a size marker, and the plasmid pRSV-pol was used as a positive control. The ~750 bp PCR products are indicated by an arrow in FIG. 2

As shown in FIG. 2, all cell lines capable of H5ts36 plaque formation at 38.5° C. contained the Ad pol DNA sequences, whereas the LP-293 cells did not yield any amplification product with these primers. This result demonstrates that each of the selected cell lines stably co-integrated not only the hygromycin resistance plasmid pCEP4, but also pRSV-pol.

f) Complementation of the Replication Defect of H5ts36 By Ad Polymerase Expressing Cell Lines The C to T transition at position 7623 of the H5ts36 genome alters the DNA binding affinity of the Ad polymerase protein, rendering it defective for viral replication at non-permissive temperatures [Chen et al. (1994) Virology 205:364; Miller and Williams (1987) J. Virol. 61:3630; and Wilkie et al. (1973) Virology 51 :499]. To analyze the functional activity of the Ad polymerase protein expressed by each of the packaging cell lines, a viral replication-complementation assay was performed. LP-293 cells or the hygromycin resistant cell lines were seeded onto 60 mM dishes at densities of 2.5–3.0'$10^6$ per dish, infected with H5ts36 at a multiplicity of infection (MOI) of 10, and incubated for 24 hours at 38.5° C., or 48 hours at 32° C. Total DNA was harvested from each plate, then 2 $\mu$g of each sample were digested with HindIII, separated on a 1.0% agarose gel, transferred to a nylon membrane, and hybridized with $^{32}$P-labeled H5ts36 virion DNA. Densitometric analysis of the 8,010 bp HindIII fragment in each lane was performed on a phophoroimager (Molecular Dynamics) utilizing a gel image processing system (IP Lab Version 1.5, Sunnyvale, Calif.).

Figure 3:
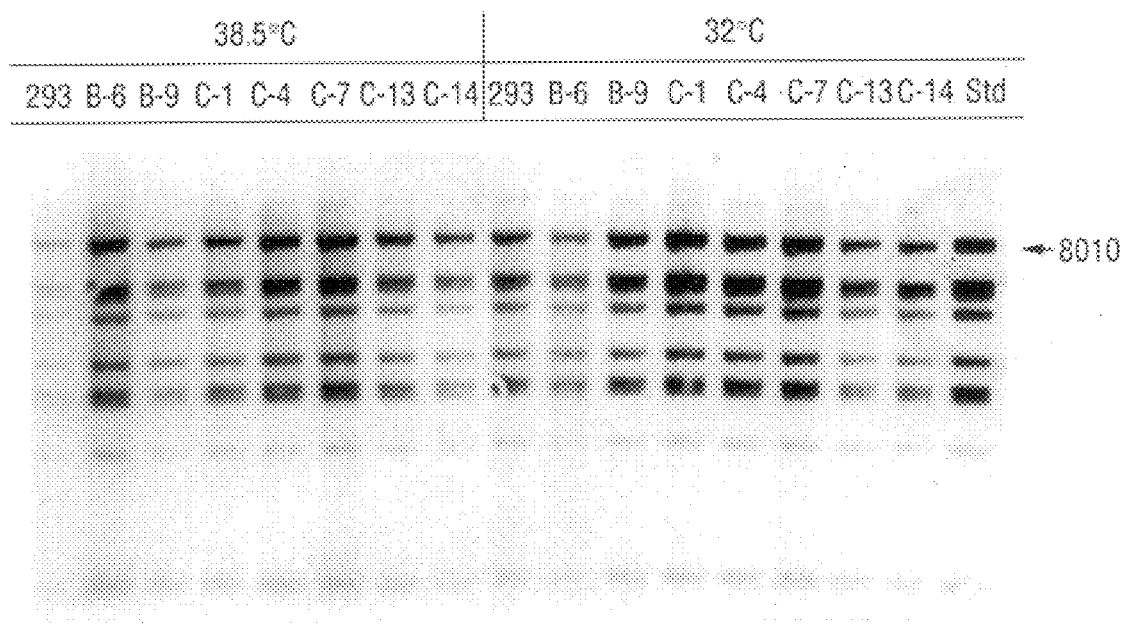
FIG. 3 is an autoradiograph depicting the results of a viral replication-complementation assay analyzing the functional activity of the Ad polymerase protein expressed by LP-293 cells and several hygromycin resistant cell lines. The 8,010 bp HindIII fragments analyzed by densitometry are indicated by an arrow.

The resulting autoradiograph is shown in FIG. 3. In FIG. 3, the lane marked "Std." (standard) contains 1 $\mu$g of HindIII-digested H5ts36 virion DNA. The 8,010 bp HindIII fragments analyzed by densitometry are indicated by an arrow.

As shown in FIG. 3, H5ts36 had a diminished ability to replicate in LP-293 cells at the non-permissive temperature. In contrast, all seven of the previously selected cell lines were able to support replication of H5ts36 virion DNA at 38.5° C. to levels approaching those occurring in LP-293 cells at 32° C.

A densitometric analysis of the amount of H5ts36 viral DNA replicated in each of the cell lines at permissive and nonpermissive temperatures is presented in Table 2 below. For this assay, the relative amounts of the 8,010 bp HindIII fragment were compared. The relative levels of H5ts36 virion DNA replication determined by densitometric analysis of the 8,010 bp HindIII fragment isolated from each of the cell line DNA samples. The surface area of the 8,010 bp fragment in 293 cells incubated at 38.5° C. was designated as 1, and includes some replicated H5ts36 virion DNA. The numbers in each column represent the ratio between the densities of the 8,010 bp fragment isolated in the indicated cell line and the density of the same band present in LP-293 cells at 38.5° C.

As shown in Table 2, the levels of replication at the permissive temperature were all within four-fold of each other, regardless of which cell line was analyzed, but at the non-permissive temperature LP-293 cells reveal the H5ts36 replication defect. The viral bands that were present in the LP-293 DNA sample at 38° C. represented input virion DNA as well as low level replication of H5ts36 DNA, which is generated due to the leakiness of the ts mutation at the high MOI utilized in this experiment. The Ad polymerase-expressing cell lines were all found to be capable of augmenting H5ts36 genome replication. Although one cell line (13–9) allowed H5ts36 replication to levels only 16 fold greater than LP-293 cells, this was the same cell line that was observed to display poor growth properties. Each of the remaining Ad polymerase-expressing cell lines allowed substantially greater replication of H5ts36 at non-permissive temperatures, compared to LP-293 cells (Table 2). An enhancement of replication up to 75 fold above that of LP-293 cells was observed with the cell line C-7 at 38.5° C. A substantially more rapid onset of viral cytopathic effect in Ad polymerase-expressing cell lines was observed at either temperature. These estimates of H5ts36 replication-complementation are conservative, since they have not been adjusted for the low level replication of H5ts36 at 33.5° C. [Miller and Williams (1937), supra]. The leakiness of the H5ts36 mutation could potentially be overcome with the use of a virus deleted for the Ad polymerase gene.

TABLE 2

Densitometric Analysis Of H5ts36 Replication

| Cell Line | Ratios Of 8,010 bp HindIII Fragment Generated At: | |
|---|---|---|
| | 32.0° C. | 38.5° C. |
| LP-293 | 42.6 | 1.0 |
| B-6 | 27.3 | 57.2 |
| B-9 | 69.0 | 15.8 |
| C-1 | 113.6 | 34.1 |
| C-4 | 100.2 | 65.5 |
| C-7 | 114.9 | 75.0 |
| C-13 | 43.1 | 42.2 |
| C-14 | 46.7 | 27.8 | g) RNA Analysis of Ad Polymerase-Expressing Cell Lines

Figure 4:
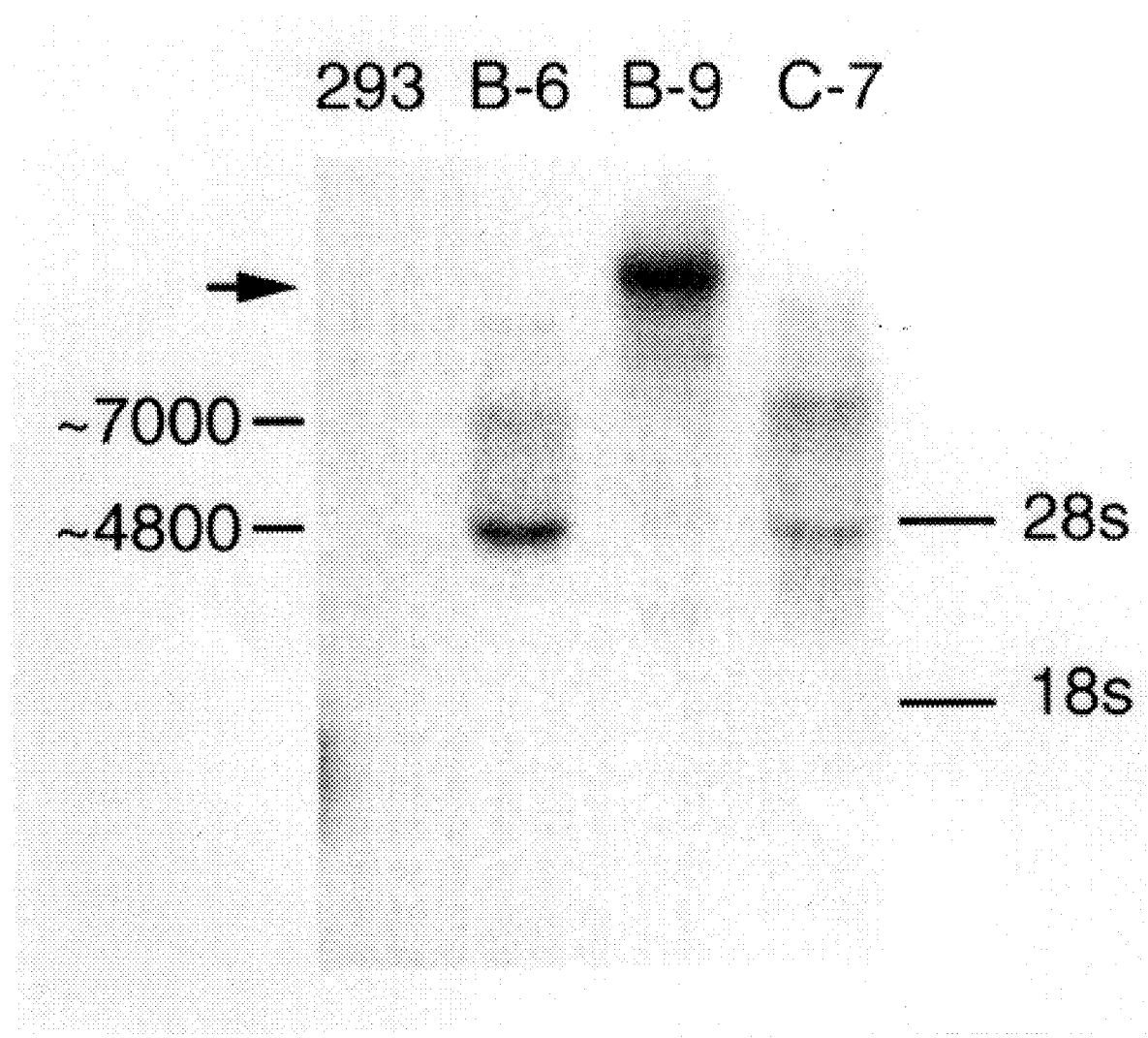
FIG. 4 is an autoradiograph indicating that cell lines B-6 and C-7 contained a smaller and a larger species of Ad polymerase mRNA while LP-293 derived RNA had no detectable hybridization signal. The location of the two species of Ad polymerase mRNA are indicated relative to the 28S and 18S ribosomal RNAs, and the aberrant transcript expressed by the B-9 cell line is indicated by an arrow.

Total RNA was extracted from each of the cell lines using the RNAzol method (Teltest, Inc., Friendswood, Tex. 77546; Chomczynski and Sacchi (1987) Anal. Biochem. 162:156]. Fifteen micrograms of RNA from each cell line was electrophoresed on a 0.8% agarose-formaldehyde gel, and transferred to a Nytran membrane (Schleicher & Schuell) by blotting. The filter was UV crosslinked, and analyzed by probing with the two $^{32}$P-labeled 1 kb ScaI subfragments of Ad which span positions 6095–8105 of the Ad5 genome (see FIG. 1A). These two ScaI subfragments of the Ad genome are complimentary to the 5' end of the Ad polymerase mRNA. The resulting autoradiograph is shown in FIG. 4. In FIG. 4, the location of the smaller and larger species of Ad polymerase mRNA are indicated relative to the 28S and 18S ribosomal RNAs. The aberrant transcript expressed by the B-9 cell line is indicated by an arrow.

The results shown in FIG. 4 revealed that the RNA derived from cell lines B-6 and C-7 contained two species of RNA, estimated to be ~4800 and ~7000 nt in length, while LP-293 derived RNA had no detectable hybridization signal. The presence of two polymerase RNA species suggests that the polyadenylation signal of the Ad IVa2 gene (present in the Ad-pol construct, see FIG. 1A) is being utilized by the cell RNA processing machinery, in addition to the SV-40 polyadenylation signal. Similar analysis of RNA derived from the cell lines C-1, C-4, C-13, and C-14 also detected the same two transcripts as those detected in the RNA of cell lines B-6 and C-7, but at decreased levels, suggesting that even low levels of Ad polymerase mRNA expression can allow for the efficient replication of polymerase mutants such as H5ts36. The cell line B-6 expressed high levels of polymerase transcript and can plaque H5ts36 one day earlier than the other cell lines at 38.5° C., suggesting a causal relationship. It is interesting to note that the two polymerase transcripts are also detected in RNA isolated from cell line B-9, but substantial amounts of a larger RNA transcript (size>10 kb) is also present (see FIG. 4). The high level production of the aberrant message may be related to the increased doubling time previously noted in this cell line.

h) Transfectability of Ad Polymerase-Expressing Cell Lines

The ability of Ad polymerase-expressing 293 cell lines to support production of H5ts36 virions after transfection with H5ts36 genome DNA was examined as follows. 293 cells as well as hygromycin resistant cell lines were grown to near confluency on 60 mm dishes and transfected with either 3 μg of purified H5ts36 virion DNA, or with 3.5 μg of the plasmid pFG140 (Microbix Biosystems), using the cationic lipid Lipofectamine (Gibco-BRL). Cells that received the H5ts36 virion DNA were incubated at 32° C. for 14 days, or 38.5° C. for 10 days. The pFG140 transfected cells were incubated at 37.5° C. for 10 days. All plates were then stained with the neutral red agar overlay and plaques were counted the next day. The results are shown in Table 3.

TABLE 3

Transfection Efficiency Of Ad pol-Expressing Cell Lines

| Cell line | Number Of Plaques At: | |
|---|---|---|
| | 32.0° C. | 38.5° C. |
| LP-293 | >500 | 0 |
| B-6 | >500 | >500 |
| B-9 | n.d.[a] | n.d. |
| C-1 | n.d. | >500 |
| C-4 | n.d. | >500 |
| C-7 | n.d. | >500 |
| C-13 | n.d. | 100 |
| C-14 | n.d. | >500 | n.d. = not determined.

The results shown in Table 3 demonstrated that transfection of H5ts36 DNA at the non-permissive temperature allows for ample plaque production in all of the Ad polymerase-expressing cell lines tested, unlike the parental LP-293 cells. Cell line C-13 was at passage number 29, and demonstrated a somewhat decreased ability to generate plaques at this extended passage number. These same cell lines are also capable of producing plaques when transfected with the plasmid pFG140, a plasmid capable of producing infectious, E1 dependent Ad upon transfection of the parental 293 cells [Ghosh-Choudhury (1986) Gene 50:161]. These observations suggest that the Ad polymerase expressing cell lines should be useful for the production of second generation Ad vectors deleted not only for the E1 genes, but also for the polymerase gene. As shown below in Examples 2 and 3, this is indeed the case.

EXAMPLE 2

Isolation and Characterization of Packaging Cell Lines That Coexpress the Adenovirus E1, DNA Polymerase and Preterminal Proteins In Example 1, packaging cell lines coexpressing Ad E1 and polymerase proteins were described. These cell lines were shown to support the replication and growth of H5ts36, an Ad with a temperature-sensitive mutation of the Ad polymerase protein. These polymerase-expressing packaging cell lines can be used to prepare Ad vectors deleted for the E1 and polymerase functions. In this example, 293 cells cotransfected with both Ad polymerase and preterminal protein expression plasmids are characterized. Cell lines co-expressing the Ad E1, polymerase and preterminal proteins can be used to prepare Ad vectors deleted for the E1, polymerase and preterminal protein (pTP) functions.

a) Tissue Culture and Virus Propagation

The use of LP-293 cells (Microbix Biosystems Inc., Toronto), Ad-polymerase expressing cell lines, and plaquing efficiency assays of Ad viruses was conducted as described in Example 1. All cells were maintained in 10% fetal bovine serum supplemented DMEM media (GIBCO) in the presence of antibiotics. The virus H5sub100 [Freimuth and Ginsberg (1986) Proc. Natl. Acad. Sci. U.S.A. 83:7816] has a temperature sensitive (ts) mutation caused by a three base pair insertion within the amino terminus of the preterminal protein, in addition to a deletion of the E1 sequences (see FIG. 1B). H5sub100 was propagated and titred at 32.0° C. in LP-293 cells; the leakiness of this stock was less than 1 per 1000 plaque-forming units (pfu) at the nonpermissive temperature of 38.5° C. A lower titer cell lysate containing the virus H5in190 (which contains a 12 base-pair insertion within the carboxy-terminus of the preterminal protein as well as a deletion of the E1 region, see FIG. 1B) was provided by Dr. P. Freimuth [Freimuth and Ginsberg (1986), supra]. The polymerase and preterminal protein expressing cell lines were always maintained in media supplemented with hygromycin (Sigma) at 100 μg/mL.

b) Isolation of Ad Polymerase and Preterminal Protein Expressing 293 Cells

The C-1, C-4, C-7, C-13, and C-14 cell lines (Ex. 1), which had been cotransfected with pRSV-pol, pRSV-pTP and CEP4, were screened for presence of pTP sequences and for the ability to support the growth of H5ts36 (ts for the Ad-polymerase), H5in190, and H5sub100 using plaque assays as described in Example 1.

i) Analysis of Genomic DNA and Cellular RNA

Cell lines that had received the preterminal protein expression plasmid were screen for the presence of pRSV-pTP sequences and E1 sequences. Total DNA was isolated from the LP-293, B-6 (transfected with pRSV-pol only) or C-7 (cotransfected with pRSV-pol and pRSV-pTP) cell lines, two micrograms (μg) of each DNA was codigested with the restriction enzymes XbaI and BamHI, electrophoretically separated in a 0.6% agarose gel, and transferred onto a nylon membrane. The membrane was UV crosslinked, probed with both a 1.8 kb BlnI-XbaI fragment (spans the E1 coding region) isolated from the plasmid pFG140, and a 1.8 kb EcoRV subfragment of Ad serotype 5 (spans the preterminal protein coding sequences; see FIG. 1B), both of which were random-primer radiolabeled with $^{32}$P to a specific activity greater than $3.0 \times 10^8$ cpm/μg. The membrane was subsequently exposed to X-ray film with enhancement by a fluorescent screen. The resulting autoradiograph is shown in FIG. 5.

Figure 5:
FIG. 5 is an autoradiograph showing which of the cell lines that received the preterminal protein expression plasmid indicated the presence of pRSV-pTP sequences (arrow labelled "pTP") and E1 sequences (arrow labelled "E1").

In FIG. 5, the preterminal specific sequences migrated as an ~11.0 kb DNA fragment while the E1 containing band migrated as a 2.3 kb DNA fragment. No hybridization of either probe to DNA isolated from either the LP-293 or B-6 cell lines was observed As shown in FIG. 5, only the C-7 cell line genomic DNA had preterminal coding sequences, unlike the parental LP-293 cells, or the Ad-polymerase expressing B-6 cells. In addition, all cell lines had E1 specific sequences present at nearly equivalent amounts, demonstrating that the selection design has not caused the loss of the E1 sequences originally present in the LP-293 cells. The results presented in Example 1 demonstrated that both the B-6 and C-7 cell lines contain polymerase specific sequences within their genomes, unlike the parental LP-293 cells.

To confirm that transcription of preterminal protein was occurring, total RNA was isolated from each of the cell lines, transferred to nylon membranes, and probed to detect preterminal protein-specific mRNA transcripts as follows. Total cellular RNA was isolated from the respective cell lines and 15 μg of total RNA from each cell line was transferred to nylon membranes. The membranes were probed with the 1.8 kb EcoRV radiolabeled subfragment of Ad5 (see FIG. 1B) complementary to the preterminal protein coding region. The resulting autoradiograph is shown in FIG. 6.

Figure 6:
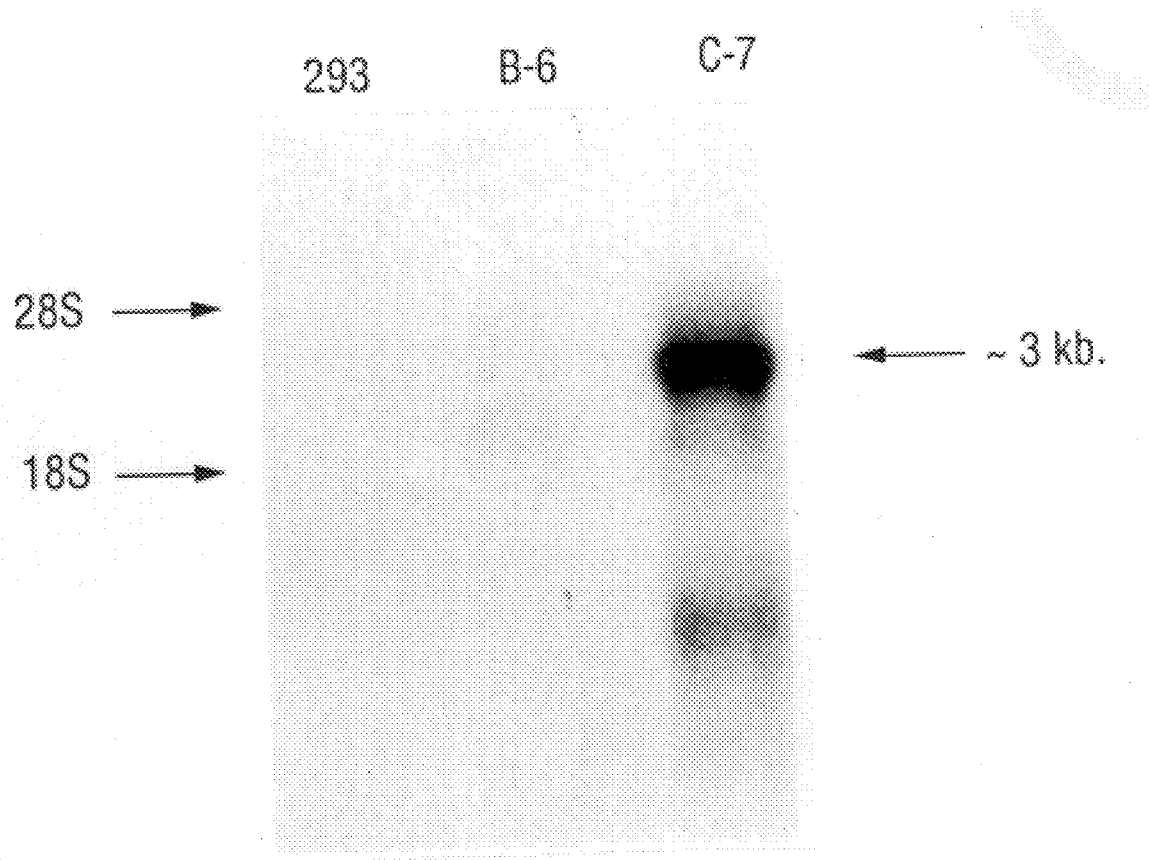
FIG. 6 is an autoradiograph indicating in which of the cell lines transcription of preterminal protein is occurring (arrow labelled "~3kb").

As shown in FIG. 6, a single mRNA of the expected size (~3 kb in length) is detected only in RNA derived from the C-7 cell line. No hybridization was detected in lanes containing RNA derived from the LP-293 or B-6 cell lines. In Example 1, it was demonstrated that the C-7 cell line also expresses high levels of the Ad polymerase mRNA. Thus, the C-7 cell line constitutively expresses both the Ads polymerase and preterminal protein mRNAs along with E1 transcripts.

ii) Plaquing Efficiency of pTP Mutants on pTP-Expressing Cell Lines

The C-7 cell line was screened for the ability to transcomplement the growth of preterminal mutant viruses. The virus H5in190 (contains a 12 base pair insertion located within the carboxy-terminus of the preterminal protein) has been shown to have a severe growth and replication defect, producing less than 10 plaque-forming units per cell [Freimuth and Ginsberg (1986) Proc. Natl. Acad. Sci. U.S.A. 83:7816]. The results are summarized in Table 4 below. For the results shown in Table 4, LP-293, B-6, or C-7 cells were seeded at a density of $2.0-2.5 \times 10^6$ cells per plate. The cells were infected with limiting dilutions of lysates derived from the preterminal protein-mutant viruses H5in190 or H5sub100, incubated at 38.5° C., and plaques counted after six days. As shown in Table 4, only the C-7 cell line could allow efficient plaque formation of H5in190 at 38.5° C. (the H5in190 lysate used to infect the cells was of a low titer, relative to the high titer H5sub100 stock), while both the B-6 and C-7 cell lines had nearly equivalent plaquing efficiencies when H5sub100 was utilized as the infecting virus.

TABLE 4

Plaquing Efficiency Of Preterminal Protein-Mutant Viruses

| Virus | Mutation Location | Plaque Titres (pfu/ml) | | |
|---|---|---|---|---|
| | | LP-293 | B-6 | C-7 |
| H5in190 | carboxy-terminus | $<1 \times 10^2$ | $<1 \times 10^2$ | $1.4 \times 10^5$ |
| H5sub100 | amino-terminus | $<1 \times 10^4$ | $9.0 \times 10^8$ | $4.5 \times 10^8$ |

As shown in Table 4, when equivalent dilutions of H5in190 were utilized, the plaquing efficiency of the C-7 cell line was at least 100-fold greater than that of the B-6 or LP-293 cells. This result demonstrated that the C-7 cell line produces a functional preterminal protein, capable of trans-complementing the defect of the H5in190 derived preterminal protein.

The cell lines were next screened for the ability to trans-complement with the temperature-sensitive virus, H5sub100, at nonpermissive temperatures. H5sub100 has a codon insertion mutation within the amino-terminus of the preterminal protein, as well as an E1 deletion. The mutation is responsible both for a temperature sensitive growth defect, as well as a replication defect [Freimuth and Ginsberg (1986), supra and Schaack et al. (1995) J. Virol.

69:4079). The plaquing efficiency of the cell line C-7 was found to be at least 1000 fold greater than that of the LP-293 cells (at nonpermissive temperatures) (see Table 4). Interestingly, the cell line B-6 was also capable of producing large numbers of H5sub100 derived plaques at 38.5° C., even though it does not express any preterminal protein. This result suggested that the high level expression of the polymerase protein was allowing plaque formation of H5sub100 in the B-6 cell line. To examine this possibility, the nature of H5sub100 growth in the various cell lines was examined.

c) Complementation of the Replication and Growth Defects of H5sub100

The cell lines B-6 and C-7 were shown to overcome the replication defect of H5ts36 (Ex. 1). Since the preterminal and polymerase proteins are known to physically interact with each other [Zhao and Padmanabhan (1988) Cell 55:1005], we investigated whether the expression of the Ad-polymerase could overcome the replication defect of H5sub100 at non-permissive temperatures using the following replication-complementation assay.

Figure 7:
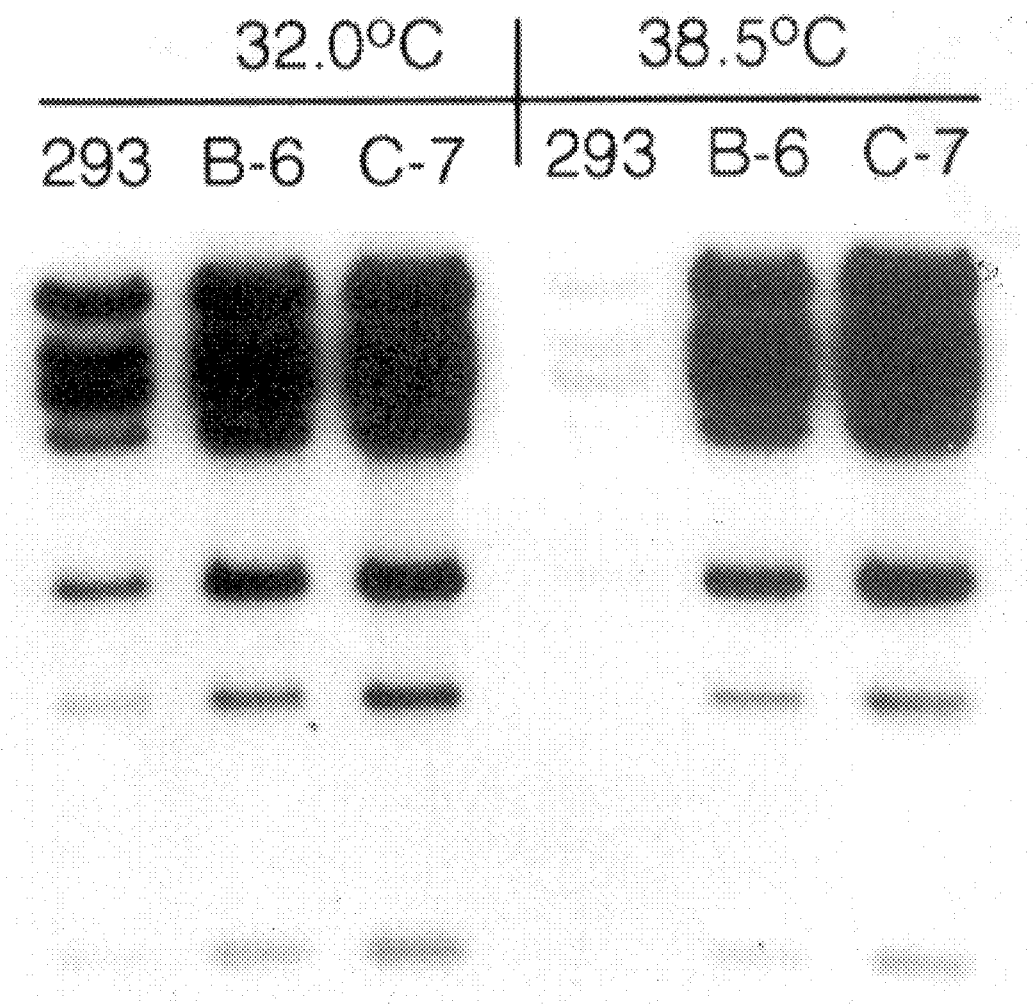
FIG. 7 is an autoradiograph indicating that the expression of the Ad-polymerase could overcome the replication defect of H5sub100 at non-permissive temperatures.

LP-293, B-6, or C-7 cells were seeded onto 60 mM dishes at a density of 2×10 cells per dish and infected the next day with H5sub100 at a multiplicity of infection (MOI) of 0.25, and incubated at 38.5° C. for 16 hours or 32.0° C. for 40 hours. The cells from each infected plate were then harvested and total DNA extracted as described in Example 1. Four micrograms of each DNA sample was digested with HindIII, electrophoresed through a 0.7% agarose gel, transferred to a nylon membrane, and probed with $^{32}$P-labeled H5ts36 virion DNA. The resulting autoradiograph is shown in FIG. 7. As seen in FIG. 7, the H5sub100 replication defect when grown in LP-293 cells at 38.5° C. is seen; this defect is not present when the virus is grown at the same temperature in either B-6 or C-7 cells.

The results depicted in FIG. 7 demonstrates that both cell lines B-6 and C-7 could trans-complement the replication defect of H5sub100. This result demonstrated that the expression of the Ad polymerase in B-6 cells was able to overcome the preterminal protein-mediated replication defect of h5sub100. While not limiting the present invention to any particular mechanism, the ability of Ad polymerase to overcome the preterminal protein-mediated replication defect of H5sub100 may be due to a direct physical interaction of the polymerase with the amino-terminus of the H5sub100-derived preterminal protein.

In support of this hypothesis, it has also been demonstrated that the H5sub100 replication defect can be overcome when LP-293 cells were infected with a 100-fold greater amount of h5sub100. However, complementation of the H5sub100 replication defect is not sufficient to overcome the growth defect of H5sub100, since temperature shift-up experiments have demonstrated that the H5sub100 growth defect is not dependent upon viral replication [Schaack et al. (1995), supra]. Therefore, the overexpression of the Ad-polymerase must have allowed a very low level but detectable production of infectious h5sub100 particles in the B-6 cell line. The reduced growth of H5sub100 is therefore not due to a replication defect, but rather some other critical activity that the preterminal protein has a role in, such as augmention of viral trascription by association with the nuclear matrix [Schaack and Shenk (1989) Curr. Top. Microbiol. Immunol. 144:185 and Hauser and Chamberlain (1996) J. Endo. 149:373]. This was confirmed by assessing the ability of the C-7 cell line to overcome the growth defect of H5sub100 utilizing one-step growth assays performed as follows.

Each of the cell lines (LP-293, B-6 and C-7) were seeded onto 60 mm dishes at 2.0×10$^6$ cells/dish. The cell lines were infected at an MOI of 4 with each of the appropriate viruses (wtAd5, H5ts36, or h5sub100), and incubated at 38.5° C. for 40 hours. The total amount of infectious virions produced in each 60 mm dish was released from the cell lysates by three cycles of freeze-thawing, and the titer was then determined by limiting dilution and plaque assay on B-6 cells at 38.5° C. The results are summarized in FIG. 8.

Figure 8:
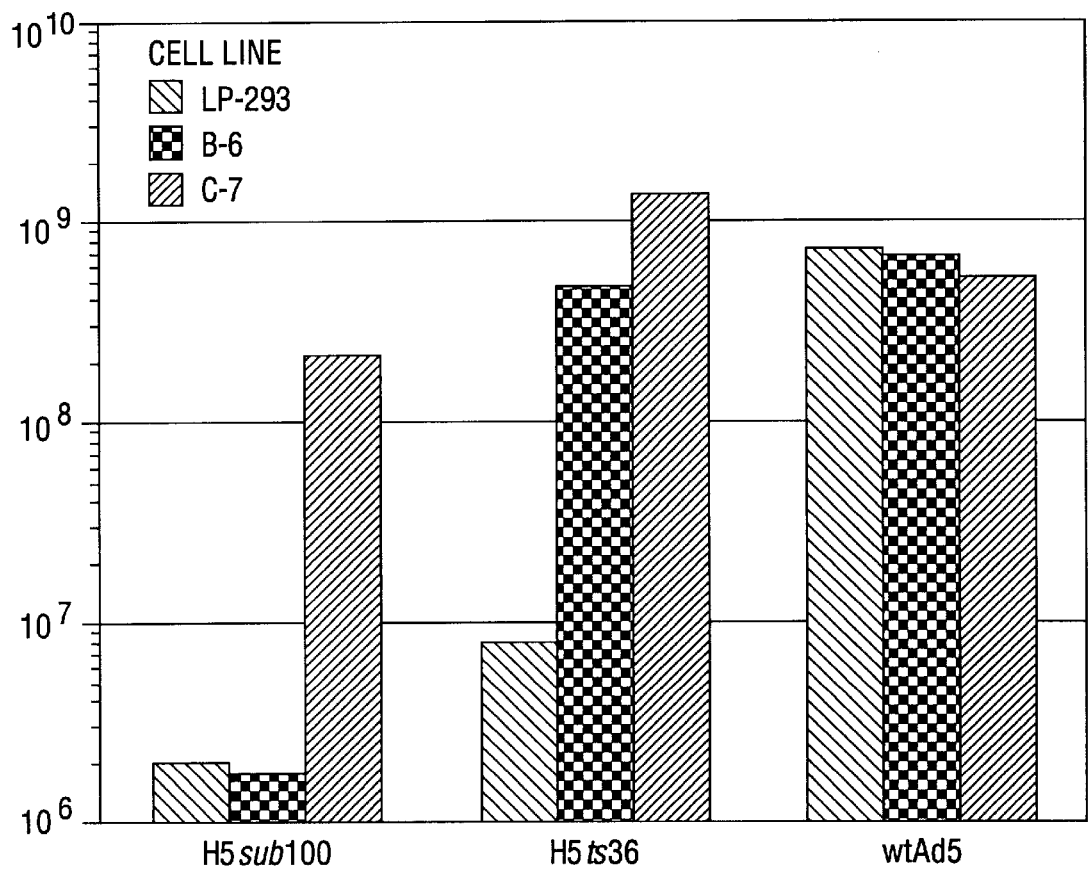
FIG. 8 graphically depicts plaque titre for LP-293, B-6 and C-7 cell lines infected with wtAd5, H5ts36, or H5sub100, and the results demonstrate that the C-7 cell line can be used as a packaging cell line to allow the high level growth of E1, preterminal, and polymerase deleted Ad vectors.

The results shown in FIG. 8, demonstrated that even though the B-6 cell line allowed normal replication and plaque formation of H5sub100 at 38.5° C. (in fact, B-6 cells were utilized to determine the plaque titres depicted in FIG. 8) they could not allow high level growth of h5sub100 and only produced titres of H5sub100 equivalent to that produced by the LP-293 cells. The C-7 cell line produced 100 fold more virus than the LP-293 or B-6 cells, see FIG. 8. Encouragingly, the titre of H5sub100 produced by the C-7 cells approached titres produced by LP-293 cells infected with wild-type virus, Ad5. When the H5sub100 virions produced from infection of the C-7 cells were used to infect LP-293 cells at 38.5° C., all virus produced retained the ts mutation (i.e., at least a 1000 fold drop in pfu was detected when LP-293 cells were respectively infected at 38.5° C. vs. 32.0° C.). This finding effectively rules out the theoretical possibility that the H5sub100 input virus genomes recombined with the preterminal protein sequences present in the C-7 cells.

In addition, the C-7 cell line allowed the high level growth of H5ts36, demonstrating that adequate amounts of the Ad-polymerase protein were also being expressed. The C-7 cell line was capable of trans-complementing the growth of both H5ts36 and H5sub100 after 4 months of serial passaging, demonstrating that the coexpression of the E1, preterminal, and polymerase proteins was not toxic.

These results demonstrate that the constitutive expression of both the polymerase and preterminal proteins is not detrimental to normal virus production, which might have occurred if one or both of the proteins had to be expressed only during a narrow time period during the Ad life cycle. In summary, these results demonstrated that the C-7 cell line can be used as a packaging cell line to allow the high level growth of E1, preterminal, and polymerase deleted Ad vectors.

EXAMPLE 3

Production of Adenovirus Vectors Deleted for E1 and Polymerase Functions

In order to produce an Ad vectors deleted for E1 and polymerase functions, a small, frame-shifting deletion was introduced into the Ad-pol gene contained within an E1-deleted Ad genome. The plasmid pBHG11 (Microbix) was used as the source of an E1-deleted Ad genome. pBHG11 contains a deletion of Ad5 sequences from bp 188 to bp 1339 (0.5–3.7 m.u.); this deletion removes the packaging signals as well as E1 sequences. pBHG11 also contains a large deletion within the E3 region (bp 27865 to bp 30995; 77.5–86.2 m.u.). The nucleotide sequence of pBHG11 is listed in SEQ ID NO:4 [for cross-corrleation between the pBHG11 sequence and the Ad5 genome (SEQ ID NO: 1), it is noted that nucleotide 8,773 in pBHG11 is equivalent to nucleotide 7,269 in Ad5].

pBHG11 was chosen to provide the Ad backbone because this plasmid contains a large deletion within the E3 region (77.5 to 86.2 m.u.) and therefore vectors derived from this plasmid permit the insertion of large pieces of foreign DNA. A large cloning capacity is important when the pol⁻ vectors is to be used to transfer a large gene such as the dystrophin gene (cDNA=13.6 kb). However, the majority of genes are not this large and therefore other Ad backbones containing smaller deletions within the E3 region (e.g., pBHG10 which contains a deletion between 78.3 to 85.8 m.u.; Microbix) may be employed for the construction of pol⁻ vectors using the strategy outlined below.

a) Construction of a Plasmid Containing a Portion of the Adenovirus Genome Containing the Polymerase Gene A fragment of the Ad genome containing the pol gene located on pBHG11 was subcloned to create pBSA-XB. Due to the large size of the Ad genome, this intermediate plasmid was constructed to facilitate the introduction of a deletion within the pol gene the pol deletion. pBSA-XB was constructed as follows. The polylinker region of pBluescript (Stratagene) was modified to include additional restriction enzyme recognition sites (the sequence of the modified polylinker is provided in SEQ ID NO:5; the remainder of pBluescript was not altered); the resulting plasmid was termed pBSX. pBHG11 was digested with XbaI and BamHI and the 20.223 kb fragment containing the pol and pTP coding regions (E2b region) was inserted into pBSX digested with XbaI and BamHI to generate pBSA-XB.

b) Construction of pBHG11Δpol

A deletion was introduced into the pol coding region contained within pBSA-XB in such a manner that other key viral elements were not disturbed (e.g., the major late promoter, the tripartite leader sequences, the pTP gene and other leader sequences critical for normal virus viability). The deletion of the pol sequences was carried out as follows. pBSA-XB was digested with BspEI and the ends were filled in using T4 DNA polymerase. The BspEI-digested, T4 polymerase filled DNA was then digested with BamHI and the 8809 bp BamHI/BspEI(filled) fragment was isolated as follows. The treated DNA was run on a 0.6% agarose gel (TAE buffer) and the 8809 bp fragment was excised from the gel and purified using a QIAEX Gel Extraction Kit according to the manufacturer's instructions (OIAGEN, Chatsworth, Calif.).

A second aliquot of pBSA-XB DNA was digested with BspHI and the ends were filled in with T4 DNA polymerase. The BspHI-digested, T4 polymerase filled DNA was then digested with BamHI and the 13,679 bp BamHI/BspHI (filled) fragment was isolated as described above.

The purified 8809 bp BamHI/BspEI(filled) fragment and the purified 13,679 bp BamHI/BspHI(filled) fragment were ligated to generate pΔpol. pΔpol contains a 612 bp deletion within the pol gene (bp 8772 to 9385; numbering relative to that of pBHG11) and lacks the 11.4 kb BamHI fragment containing the right arm of the Ad genome found within pBHG11.

To provide the right arm of the Ad genome, pΔpol was digested with BamHI followed by treatment with calf intestinal alkaline phosphatase. pBHG11 was digested with BamHI and the 11.4 kb fragment was isolated and purified using a QIAEX Gel Extraction Kit as described above. The purified 11.4 kb BamHI fragment was ligated to the BamHI/ phosphatased pΔpol to generate pBHG11Δpol. Proper construction of pBHG11Δpol was confirmed restriction digestion (HindIII).

c) Rescue and Propagation of Ad5Δpol Virus

The Ad genome contained within pBHG11Δpol lacks the packaging signals. Therefore, in order to recover virus containing the 612 bp deletion within the pol gene from pBHG11Δpol, this plasmid must be cotransfected into packaging cells along with DNA that provides a source of the Ad packaging signals. The Ad packaging signals may be provided by wild-type or mutant Ad viral DNA or alternatively may be provided using a shuttle vector which contains the left-end Ad5 sequences including the packaging signals such as pΔE1sp1A, pΔE1sp1B (Microbix) or pAdBglII (pAdBglII is a standard shuttle vector which contains 0–1 m.u. and 9–16 m.u. of the adenovirus genome).

To rescue virus, pBHG11Δpol was co-transfected with Ad5dl7001 viral DNA. Ad5dl7001 contains a deletion in the E3 region; the E3 deletion contained within Ad5dl100 is smaller than the deletion contained within the Ad genome contained within pBHG11. It is not necessary that Ad5dl7001 be used to recover virus; other adenoviruses, including wild-type adenoviruses, may be used to rescue of virus from pBHG11Δpol.

It has been reported that the generation of recombinant Ads is more efficient if Ad DNA-terminal protein complex (TPC) is employed in conjunction with a plasmid containing the desired deletion [Miyake et al. (1996) Proc. Natl. Acad. Sci. U.S.A. 93:1320]. Accordingly, Ad5dl7001-TPC were prepared as described [Miyake et al. (1996), supra]. Briefly, purified Ad5dl7001 virions (purified through an isopycnic CsCl gradient centered at 1.34 g/ml) were lysed by the addition of an equal volume of 8 M guanidine hydrochloride. The released Ad5dl7001 DNA-TPC was then purified through a buoyant density gradient of 2.8 M CsCl/4 M guanidine hydrochloride by centrifugation for 16 hr at 55,000 rpm in a VTi65 rotor (Beckman). Gradient fractions containing Ad5dl7001 DNA-TPC were identified using an ethidium bromide spot test and then pooled, dialyzed extensively against TE buffer. BSA was then added to a final concentration of 0.5 mg/ml and aliquots were stored at −80° C. The A4dl7001 DNA-TPC was then digested with ScaI and then gel-filtered through a Sephadex G-50 spin column.

One hundred nanograms of the digested Ad5dl7001 DNA-TPC was mixed with 5 μg of pBHG11Δpol and used to transfect pol-expressing 293 cells (i.e., C-7). Approximately 10 days post-transfection, plaques were picked. The recombinant viruses were plaque purified and propagated using standard techniques (Graham and Prevac, supra). Viral DNA was isolated, digested with restriction enzymes and subjected to Southern blotting analysis to determine the organization of the recovered viruses. Two forms of virus containing the 612 bp pol deletion were recovered and termed Ad5ΔpolΔE3I and Ad5ΔpolΔE3II. One form of recombinant pol⁻ virus recovered, Ad5ΔpolΔE3I, underwent a double recombination event with the Ad5dl7001 sequences and contains the E3 deletion contained within Ad5dl7001 at the right end of the genome. The second form of recombinant pol virus, Ad5ΔpolΔE3II, retained pBHG11 sequences at the right end of the genome (i.e., contained the E3 deletion found within pBHG11). These results demonstrate the production of a recombinant Ad vector containing a deletion within the pol gene.

d) Characterization of The E1+, pol− Viruses

Figure 9:
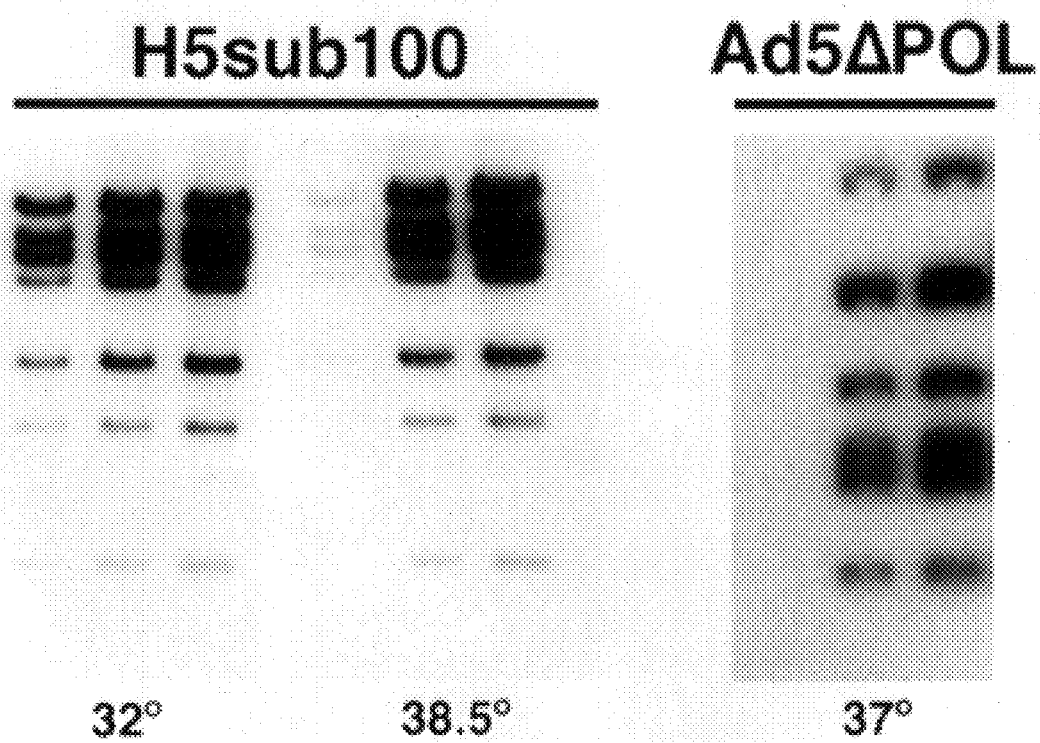
FIG. 9 is an autoradiograph showing that the recombinant pol⁻ virus is viable on pol-expressing 293 cells but not on 293 cells which demonstrates that recombinant Ad viruses containing the 612 bp deletion found within pΔpol lack the ability to express Ad polymerase.

To demonstrate that the deletion contained within these two pol⁻ viruses renders the virus incapable of producing functional polymerase, Ad5ΔpolΔE3I was used to infect 293 cells and pol-expressing 293 cells (B-6 and C-7 cell lines) and a viral replication-complementation assay was performed as described in Example 1e. Briefly, 293, B-6 and C-7 cells were seeded onto 60 mm dishes at a density of 2×10⁶ cells/dish and infected with H5sub100 or Ad5ΔpolΔE3I at an MOI of 0.25. The infected cells were then incubated at 37° C. or 38.5° C. for 16 hours, or at 32.0° C. for 40 hours. Cells from each infected plate were then harvested and total DNA was extracted. Four micrograms of each DNA sample was digested with HindIII, electrophoresised through an agarose gel, transferred to a nylon membrane and probed with $^{32}$P-labeled adenoviral DNA. The resulting autograph is shown in FIG. 9. In FIG. 9, each panel shows, from left to right, DNA extracted from 293, B-6 and C-7 cells, respectively infected with either H5sub100 or Ad5ΔpolΔE3I (labeled Ad5ΔPOL in FIG. 9).

As shown in FIG. 9, the recombinant pol⁻ virus was found to be viable on pol-expressing 293 cells but not on 293 cells. These results demonstrates that recombinant Ad viruses containing the 612 bp deletion found within pΔpol lack the ability to express Ad polymerase. These results also demonstrate that B-6 and C-7 cells efficiently complement the Δpol found within Ad5ΔpolΔE3I and Ad5ΔpolΔE3II. In addition, these results show that replication of the ts pTP mutant H5sub100 can be complemented by high level expression of the Ad polymerase with or without co-expression of pTP.

Because the expression of early genes is required for the expression of the late gene products, the ability of recombinant viruses contain the Δpol deletion to direct the expression of late gene products was examined. 293 and C-7 cells were infected with Ad5ΔpolΔE3I and 24 hours after infection cell extracts were prepared. The cell extracts were serially diluted and examined for the expression of the fiber protein (a late gene product) by immunoblot analysis. The immunoblot was performed as described in Example 3C with the exception that the primary antibody used was an anti-fiber antibody (FIBER-KNOB obtained from Robert Gerard, University of Texas Southwestern Medical School). The results of this immunoblotting analysis revealed that no fiber protein was detected from 293 cells infected with Ad5ΔpolΔE3I (at any dilution of the cell extract). In contrast, even a 1:1000 dilution of cell extract prepared from C-7 cells infected with Ad5ΔpolΔE3I produced a visible band on the immunoblot. Therefore, the pol deletion contained within Ad5ΔpolΔE3I resulted in a greater than 1000-fold decrease in fiber production.

The above results demonstrate that polymerase gene sequences can be deleted from the virus and that the resulting deleted virus will only grow on cells producing Ad-polymerase in trans. Using the pol-expressing cell lines described herein (e.g., B-6 and C-7), large quantities of the pol⁻ viruses can be prepared. A dramatic shut-down in growth and late gene expression is seen when cells which do not express Ad polymerase are infected with the pol⁻ viruses.

e) Generation of E1⁻, Pol⁻ Ad Vectors

Ad5dl7001 used above to recuse virus containing the polymerase deletion is an E1-containing virus. The presence of E1 sequences on the recombinant pol⁻ viruses is undesirable when the recombinant virus is to be used to transfer genes into the tissues of animals; the E1 region encodes the transforming genes and such viruses replicate extremely well in vivo leading to an immune response directed against cells infected with the E1-containing virus.

E1⁻ viruses containing the above-described polymerase deletion are generated as follows. pBHG11Δpol is cotransfected into pol-expressing 293 cells (e.g., B-6 or C-7) along with a shuttle vector containing the left-end Ad5 sequences including the packaging signals. Suitable shuttle vectors include pΔE1sp1A (Microbix), pΔE1sp1B (Microbix) or pAdBglII. The gene of interest is inserted into the polylinker region of the shuttle vector and this plasmid is then cotransfected into B-6 or C-7 cells along with pBHG11Δpol to generate a recombinant E1⁻, pol⁻ Ad vector containing the gene of interest.

EXAMPLE 4

Production of Adenovirus Vectors Deleted For E1 and Preterminal Protein Functions In order to produce an Ad vectors deleted for E1 and preterminal protein functions, a small deletion was introduced into the Ad preterminal protein (pTP) gene contained within an E1-deleted Ad genome. The plasmid pBHG11 (Microbix) was used as the source of an E1-deleted Ad genome to maximize the cloning capacity of the resulting pTP⁻ vector. However, other Ad backbones containing smaller deletions within the E3 region (e.g., pBHG10 which contains a deletion between 78.3 to 85.8 m.u.; Microbix) may be employed for the construction of pTP⁻ vectors using the strategy outlined below.

a) Construction of pΔpTP

A deletion was introduced into the pTP coding region contained within pBSA-XB (Ex. 3) in such a manner that other key viral elements were not disturbed (e.g., the tripartite leader sequences, the i-leader sequences, the VA-RNA I and II genes, the 55 kD gene and the pol gene). The deletion of the pTP sequences was carried out as follows. pBSA-XB was digested with XbaI and EcoRV and the 7.875 kb fragment was isolated as described (Ex. 3). Another aliquot of pBSA-XB was digested with MunI and the ends were filled in using T4 DNA polymerase. The MunI-digested, T4 polymerase filled DNA was then digested with XbaI and the 14.894 kb XbaI/MunI(filled) fragment was isolated as described (Ex. 3). The 7.875 kb MunI fragment and the 14.894 kb XbaI/MunI(filled) fragment were ligated together to generate pΔpTP.

b) Construction of pBHG11ΔpTP pΔpol contains a 429 bp deletion within the pTP gene (bp 10,705 to 11,134; numbering relative to that of pBHG11) and lacks the 11.4 kb BamHI fragment containing the right arm of the Ad genome found within pBHG11.

To provide the right arm of the Ad genome, pΔpTP was digested with BamHI followed by treatment with shrimp alkaline phosphatase (SAP; U.S. Biochemicals, Cleveland, Ohio). pBHG11 was digested with BamHI and the 11.4 kb fragment was isolated and purified using a QIAEX Gel Extraction Kit as described (Ex. 3). The purified 11.4 kb BamHI fragment was ligated to the BamHI/phosphatased pΔpTP to generate pBHG11ΔpTP. Proper construction of pBHG11ΔpTP was confirmed restriction digestion.

c) Rescue and Propagation of Ad Vectors Containing the pTP Deletion

The Ad genome contained within pBHG11ΔpTP lacks the Ad packaging signals. Therefore, in order to recover virus containing the 612 bp deletion within the pol gene from pBHG11Δpol, this plasmid must be cotransfected into packaging cells along with DNA that provides a source of the Ad packaging signals. The Ad packaging signals may be provided by wild-type or mutant Ad viral DNA or alternatively may be provided using a shuttle vector which contains the left-end Ad5 sequences including the packaging signals such as pΔE1sp1A, pΔE1sp1B (Microbix) or pAdBglII.

Recombinant Ad vectors containing the pTP deletion which contain a deletion within the E3 region are generated by cotransfection of pBHG11ΔpTP (the gene of interest is inserted into the unique PacI site of pBHG11ΔpTP) with a E3-deleted Ad virus such as Ad5dl700 into pTP-expressing 293 cells (e.g., C-7); viral DNA-TPC are utilized as described above in Example 3.

Recombinant vectors containing the pTP deletion which also contain deletions within the E1 and E3 regions are generated by cotransfection of pBHG11ΔpTP into pTP-expressing 293 cells (e.g., C-7) along with a shuttle vector containing the left-end Ad5 sequences including the packaging signals. Suitable shuttle vectors include pΔE1sp1A (Microbix), pΔE1sp1B (Microbix) or pAdBglII. The gene of interest is inserted into the polylinker region of the shuttle vector and this plasmid is then cotransfected into B-6 or C-7 cells along with pBHG11ΔpTP to generate a recombinant E1$^-$, pTP$^-$ Ad vector containing the gene of interest.

EXAMPLE 5

Production of Adenovirus Vectors Deleted for E1, Polymerase and Preterminal Protein Functions In order to produce an Ad vectors deleted for E1, polymerase and preterminal protein functions, a deletion encompassing pol and pTP gene sequences was introduced into the Ad sequences contained within an E1-deleted Ad genome. The plasmid pBHG11 ΔE4 was used as the source of an E1-deleted Ad genome to maximize the cloning capacity of the resulting pol$^-$, pTP$^-$ vector. pBHG11 ΔE4 is a modified form of BHG11 which contains a deletion of all E4 genes except for the E4 ORF 6; the E4 region was deleted to create more room for the insertion of a gene of interest and to further disable the virus. However, other E1$^-$ Ad backbones, such as pBHG11 and pBHG1 (Microbix; pBHG10 contains a smaller deletion within the E3 region as compared to pBHG11), may be employed for the construction of pol$^-$, pTP$^-$ vectors using the strategy outlined below.

Due to the complexity of the cloning steps required to introduce a 2.3 kb deletion that removes portions of both the pTP and pol genes, this deletion was generated using several steps as detailed below.

a) Construction of pAXBΔpolΔpTPVARNA+t13

In order to create a plasmid containing Ad sequences that have a deletion within the pol and pTP genes, pAXBΔpolΔpTPVARNA+t13 was constructed as follows.

pBSA-XB was digested with BspEI and the 18 kb fragment was isolated and recircularized to create pAXBΔpolΔpTP; this plasmid contains a deletion of the sequences contained between the BspEI sites located at 8,773 and 12,513 (numbering relative to pBHG11).

A fragment encoding the VA-RNA3 sequence and the third leader of the tripartite leader sequence was prepared using the PCR as follows. The PCR was carried out in a solution containing H5ts36 virion DNA (any Ad DNA, including wild-type Ad, may be used), 2 ng/mL of primers 4005E and 4006E, 10 mM Tris.HCl, pH 8.3, 50 mM KCl, 1.5 mM MgCl$_2$, 0.001% gelatin and Pfu polymerase. The forward primer, 4005E, [5'-TGCCGCAGCACCGGATGCATC-3' (SEQ ID NO:6)] contains sequences complementary to residues 12,551 to 12,571 of pBHG11(SEQ ID NO:4). The reverse primer, 4006E, [5'-GCGTCCGGAGGCTGCCATG CGGCAGGG-3' (SEQ ID NO:7)] is complementary to residues 11,091 to 11,108 of pBHG11 (SEQ ID NO:4) as well as a BspEI site (underlined). The predicted sequence of the ~1.6 kb PCR product is listed in SEQ ID NO:8.

PCR was performed with a Perkin Elmer 9600 Thermocycler utilizing the following cycling parameters: initial denaturation at 94° C. for 3 min, 3 cycles of denaturation at 94° C. for 30 sec, annealing at 50° C. for 30 sec, and extension at 72° C. for 60 sec, followed by another 27 cycles with an increased annealing temperature at 56° C., with a final extension at 72° C. for 10 minutes. The ~1.6 kb PCR product was purified using a QIAEX Gel Extraction Kit as described (Ex. 3).

The purified PCR fragment was then digested with BspEI. pAXBΔpolΔpTP was digested with BspEI followed by treatment with SAP. The BspEI-digested PCR fragment and the BspEI-SAP-treated pAXBΔpolΔpTP were ligated together to create pAXBΔpolΔpTPVARNA+t13.

b) Construction of pBHG11ΔpolΔpTPVARNA+t13 pAXBΔpolΔpTPVARNA+t13 contains a 2.3 kb deletion within the pol and pTP genes (bp 8,773 to 11,091; numbering relative to that of pBHG11) and lacks the 11.4 kb BamHI fragment containing the right arm of the Ad genome.

To provide the right arm of the Ad genome, pAXBΔpolΔpTPVARNA+t13 was digested with BamHI followed by treatment with SAP. pBHG11ΔE4 (PBHG11 or pBHG10 may be used in place of pBHG11ΔE4) was digested with BamHI and the 11.4 kb fragment was isolated and purified using a QIAEX Gel Extraction Kit as described (Ex. 3). The purified 11.4 kb BamHI fragment was ligated to the BamHI/phosphatased pAXBΔpolΔpTPVARNA+t13 to generate pBHG11ΔpolΔpTPVARNA+t13 . Proper construction of pBHG11ΔpolΔpTPVARNA+t13 was confirmed restriction digestion.

c) Rescue and Propagation of Ad Vectors Containing the pol, pTP Double Deletion

The Ad genome contained within pBHG11ΔpolΔpTPVARNA+t13 lacks the Ad packaging signals. Therefore, in order to recover virus containing the 2.3 kb deletion within the pol and pTP genes from pBHG11ΔpolΔpTPVARNA+t13 , this plasmid must be cotransfected into packaging cells along with DNA that provides a source of the Ad packaging signals. The Ad packaging signals may be provided by wild-type or mutant Ad viral DNA or alternatively may be provided using a shuttle vector which contains the left-end Ad5 sequences including the packaging signals such as pΔE1sp1A, pΔE1sp1B (Microbix) or pAdBglII.

Recombinant vectors containing the pol, pTP double deletion which also contain a deletion within the E3 region are generated by cotransfection of pBHG11ΔpolΔpTPVARNA+t13 (the gene of interest is inserted into the unique PacI site of pBHG11ΔpolΔpTPVARNA+t13 ) with a E3-deleted Ad virus such as Ad5dl7001 into pol- and pTP-expressing 293 cells (e.g., C-7); viral DNA-TPC are utilized as described (Ex. 3).

Recombinant vectors containing the pol, pTP double deletion which also contain deletions within the E1 and E3 regions are generated by cotransfection of pBHG11ΔpolΔpTPVARNA+t13 into pol- and pTP-expressing 293 cells (e.g., C-7) along with a shuttle vector containing the left-end Ad5 sequences including the packaging signals. Suitable shuttle vectors include pΔE1sp1A (Microbix), pΔE1sp1B (Microbix) or pAdBglII. The gene of interest is inserted into the polylinker region of the shuttle vector and this plasmid is then cotransfected into B-6 or C-7 cells along with pBHG11ΔpolΔpTPVARNA+t13 to generate a recombinant E1$^-$, pol$^-$, pTP$^-$ Ad vector containing the gene of interest.

EXAMPLE 6

Encapsidated Adenovirus Minichromosomes Containing a Full Length Dystrophin cDNA In this Example, the construction of an encapsidated adenovirus minichromosome (EAM) consisting of an infectious encapsidated linear genome containing Ad origins of replication, packaging signal elements, a β-galactosidase reporter gene cassette and a full length (14 kb) dystrophin cDNA regulated by a muscle specific enhancer/promoter is described. EAMs are generated by cotransfecting 293 cells with supercoiled plasmid DNA (pAd5βdys) containing an embedded inverted origin of replication (and the remaining above elements) together with linear DNA from E1-deleted virions expressing human placental alkaline phosphatase (hpAP). All proteins necessary for the generation of EAMs are provided in trans from the hpAP virions and the two can be separated from each other on equilibrium CsCl gradients. These EAMs are useful for gene transfer to a variety of cell types both in vitro and in vivo.

a) Generation and Propagation of Encapsidated Adenovirus Minichromosomes

To establish a vector system capable of delivering full length dystrophin cDNA clones, the minimal region of Ad5 needed for replication and packaging was combined with a conventional plasmid carrying both dystrophin and a β-galactosidase reporter gene. In the first vector constructed, these elements were arranged such that the viral ITRs flanked (ITRs facing outward) the reporter gene and the dystrophin gene [i.e., the vector contained from 5' to 3' the right or 3' ITR (mu 100 to 99), the dystrophin gene and the reporter gene and the left or 5' ITR and packaging sequence (mu 1 to 0)]. Upon introduction of this vector along with helper virus into 293 cells, no encapsidated adenovirus minichromosomes were recovered.

The second and successful vector, pAd5βdys (FIG. 10) contains 2.1 kb of adenovirus DNA, together with a 14 kb murine dystrophin cDNA under the control of the mouse muscle creatine kinase enhancer/promoter, as well as a β-galactosidase gene regulated by the human cytomegalovirus enhancer/promoter.

Figure 10:
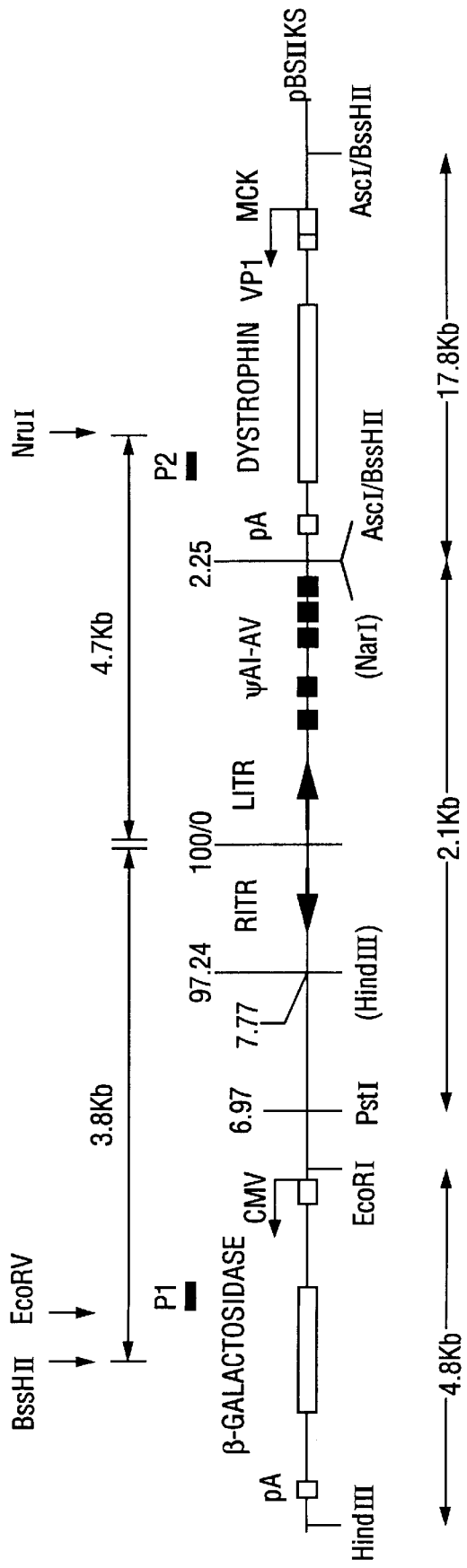
FIG. 10 is a schematic representation of the structure of pAd5βdys wherein the two inverted adenovirus origins of replication are represented by a left and right inverted terminal repeat (LITR/RITR). P1 and P2 represent location of probes used for Southern blot analysis.

FIG. 10 shows the structure of pAd5βdys (27.8 kb). The two inverted adenovirus origins of replication are represented by a left and right inverted terminal repeat (LITR/RITR). Replication from these ITRs generates a linear genome whose termini correspond to the 0 and 100 map unit (mu) locations. Orientation of the origin with respect to wild type adenovirus serotype 5 sequences in mu is indicated above the figure (1 mu=360 bp). Encapsidation of the mature linear genome is enabled by five (AI–AV) packaging signals (Ψ). The E. coli β-galactosidase and M. musculus dystrophin cDNAs are regulated by cytomegalovirus (CMV) and muscle creatine kinase (MCK) enhancer/promoter elements, respectively. Both expression cassettes contain the SV40 polyadenylation (pA) signal. Since the E1A enhancer/promoter overlaps with the packaging signals, pAd5 βdys was engineered such that RNA polymerase transcribing from the E1A enhancer/promoter will encounter the SV40 late polyadenylation signal. Pertinent restriction sites used in constructing pAd5βdys are indicated below the figure. An adenovirus fragment corresponding to mu 6.97 to 7.77 was introduced into pAd5βdys during the cloning procedure (described below). P1 and P2 represent location of probes used for Southern blot analysis. Restriction sites destroyed during the cloning of the Ad5 origin of replication and packaging signal are indicated in parentheses.

pAd5βdys was constructed as follows. pBSX (Ex. 3a) was used as the backbone for construction of pAd5βdys. The inverted fused Ad5 origin of replication and five encapsidation signals were excised as a PstI/XbaI fragment from pAd5ori, a plasmid containing the 6 kb HindIII fragment from pFG140 (Microbix Biosystems). This strategy also introduced a 290 bp fragment from Ad5 corresponding to map units 6.97 to 7.77 adjacent to the right inverted repeat (see FIG. 10). The E. coli β-galactosidase gene regulated by the human CMV immediate early (IE) promoter/enhancer expression cassette was derived as an EcoRI/HindIII fragment from pCMVβ [MacGregor and Caskey (1989) Nucleic Acids Res. 17:2365]; the CMV IE enhancer/promoter is available from a number of suppliers as is the E. coli β-galactosidase gene]. The murine dystrophin expression cassette was derived as a BssHII fragment from pCVAA, and contains a 3.3 kb MCK promoter/enhancer element [Phelps et al. (1995) Hum. Mol. Genet. 4:1251 and Jaynes et al. (1986) Mol. Cell. Biol. 6:2855]. The sequence of the ~3.3 kb MCK promoter/enhancer element is provided in SEQ ID NO:9 (in SEQ ID NO:9, the last nucleotide of SEQ ID NO:9 corresponds to nucleotide +7 of the MCK gene). The enhancer element is contained within a 206 bp fragment located −1256 and −1050 upstream of the transcription start site in the MCK gene.

It was hoped that the pAd5βdys plasmid would be packageable into an encapsidated minichromosome when grown in parallel with an E1-deleted virus due to the inclusion of both inverted terminal repeats (ITR) and the major Ad packaging signals in the plasmid. The ITRs and packaging signals were derived from pFG140 (Microbix), a plasmid that generates E1-defective Ad particles upon transfection of human 293 cells.

hpAP is an E1 deleted Ad5 containing the human placental alkaline phosphatase gene [Muller et al. (1994) Circ. Res. 75:1039]. This virus was chosen to provide the helper functions so that it would be possible to monitor the titer of the helper virus throughout serial passages by quantitative alkaline phosphatase assays.

293 cells were cotransfected with pAd5βdys and hpAP DNA as follows. Low passage 293 cells (Microbix Biosystems) were grown and passaged as suggested by the supplier. Five pAd513dys and hpAP DNA (5 and 0.5 μg, respectively) were dissolved in 70 μl of 20 mM HEPES buffer (pH 7.4) and incubated with 30 μl of DOTAP (BMB) for 15 min. at room temperature. This mixture was resuspended in 2 mls of DMEM supplemented with 2% fetal calf serum (FCS) and added dropwise to a 60 mm plate of 293 cells at 80% confluency. Four hours post-transfection the media was replaced by DMEM with 10% FCS. Cytopathic effect was observed 6–12 days post-transfection.

Figure 11:
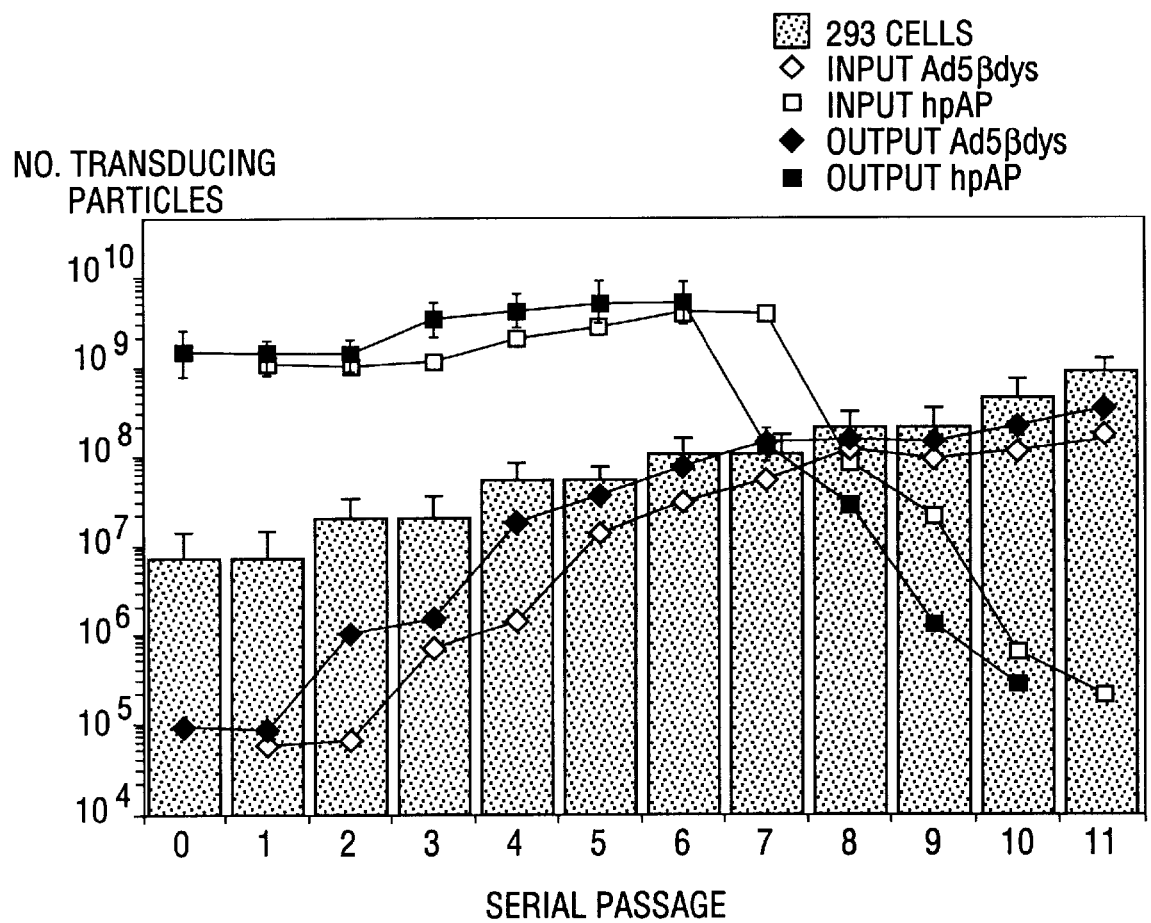
FIG. 11 graphically illustrates the total number of transducing adenovirus particles produced (output) per serial passage on 293 cells, total input virus of either the helper (hpAP) or Ad5βdys, and the total number of cells used in each infection.

Cotransfection of 293 cells with supercoiled pAd5βdys and linear hpAP DNA produced Ad5βdys EAMs (the encapsidated version of pAd5βdys) approximately 6 to 12 days post transfection, as evidenced by the appearance of a cytopathic effect (CPE). Initially, the amount of Ad5βdys EAMs produced was significantly lower than that of hpAP virions so the viral suspension was used to re-infect fresh cultures, from which virus was isolated and used for serial infection of additional cultures (FIG. 11). Infection and serial passaging of 293 cells was carried out as follows.

Lysate from one 60 mm plate of transfected 293 cells was prepared by vigorously washing the cells from the plate and centrifuging at 1 K rpm in a clinical centrifuge. Cells were resuspended in DMEM and 2% FCS, freeze-thawed in a dry ice-ethanol bath, cell debris removed by centrifugation, and approximately 75% of the crude lysate was used to infect 293 cells in DMEM supplemented with 2% FCS for 1 hour and then supplemented with 10% FCS thereafter. Infection was allowed to proceed for 18–20 hrs before harvesting the virus. The total number of cells infected in each serial passage is indicated in FIG. 11.

In FIG. 11, the total number of transducing adenovirus particles produced (output) per serial passage on 293 cells, total input virus of either the helper (hpAP) or Ad5βdys, and the total number of cells used in each infection is presented. The total number of input/output transducing particles were determined by infection of 293 cells plated in 6-well microtiter plates. Twenty four hours post-infection the cells were assayed for alkaline phosphatase or β-galactosidase activity (described below) to determine the number of cells transduced with either Ad5βdys or hpAP. The number of transducing particles were estimated by extrapolation of the mean calculated from 31 randomly chosen 2.5 mm$^2$ sectors of a 961 nm$^2$ plate. The intra-sector differences in total output of each type of virus are presented as the standard deviations, σ, in FIG. 11. For each serial passage, 75% of the total output virus from the previous passage was used for infection.

Alkaline phosphatase or β-galactosidase activity was determined as follows. For detection of alkaline phosphatase, infected 293 cells on Petri dishes were rinsed twice with phosphate buffered saline (PBS) and fixed for 10 minutes in 0.5% glutaraldehyde in PBS. Cells were again rinsed twice with PBS for ten minutes followed by inactivation of endogenous alkaline phosphatase activity at 65° C. for 1 hr. in PBS prior to the addition of the chromogenic substrate BCIP (5-bromo-4-chloro-3-indolyl phosphate) at 0.15 mg/ml and nitro blue tetrazolium at 0.3 mg/ml). Cells were incubated at 37° C. in darkness for 3–24 hrs. For β-galactosidase assays, the cells were fixed and washed as above, then assayed using standard methods [MacGregor et al. (1991) In Murray (ed.), *Methods in Molecular Biology*, Vol. 7: *Gene Transfer and Expression Protocols*, Human Press Inc., Clifton, N.J., pp. 217–225].

As shown in FIG. 11, the rate of increase in titer of Ad5 βdys EAMs between transfection and serial passage 6 was approximately 100 times greater than that for hpAP virions. This result indicated that Ad5βdys has a replication advantage over the helper virus, probably due to the shorter genome length (a difference of approximately 8 kb) and hence an increased rate of packaging.

Interestingly, after serial passage 6 there was a rapid decrease in the total titer of hpAP virions whereas the titer of Ad5βdys EAMs continued to rise. While not limiting the present invention to any particular mechanism, at least two possible mechanisms could be responsible for this observation. Firstly, a buildup of defective hpAP virions due to infections at high multiplicities may slowly out-compete their full length counterparts, a phenomenon that has been previously observed upon serial propagation of adenovirus [Daniell (1976) J. Virol. 19:685; Rosenwirth et al. (1974) Virology 60:431; and Burlingham et al. (1974) Virology 60:419]. Secondly, the emergence of replication competent virions due to recombination events between E1 sequences in cellular DNA and the hpAP genome could lead to a buildup of virus particles defective in expressing alkaline phosphatase [Lochmüller et al. (1994) Hum. Gene Ther. 5:1485].

Figures 12A, 12B:
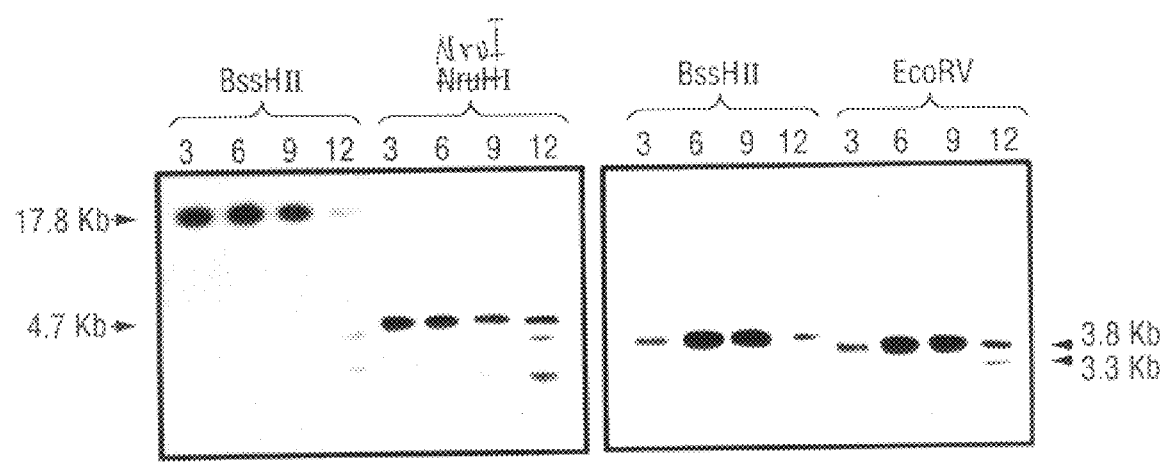
FIGS. 12A–B show Southern blot analyses of viral DNA from lysates 3, 6, 9 and 12, digested with the restriction enzymes BssHII, NruI and EcoRV. For the analyses, fragments from the C terminus of *M. musculus* dystrophin cDNA (A) or the N terminus of *E. coli* β-galactosidase (B) were labeled with dCTP$^{32}$ and used as probes.

Southern analysis of DNA prepared from serial lysates 3, 6, 9 and 12 indicated that full length dystrophin sequences were present in each of these lysates (FIG. 12A). In addition, the correct size restriction fragments were detected using both dystrophin and β-galactosidase probes against lysate DNA digested with several enzymes (FIGS. 12A–B).

FIG. 12 shows a Southern blot analysis of viral DNA from lysates 3, 6, 9 and 12, digested with the restriction enzymes BssHII, NruI and EcoRV, indicating the presence of a full length dystrophin cDNA in all lysates. Fragments from the C terminus of *M. musculus* dystrophin cDNA (A) or the N terminus of *E. coli* β-galactosidase (B) were labeled with dCTP$^{32}$ and used as probes [Sambrook et al, supra]. The position of these probes and the predicted fragments for each digest is indicated in FIG. 10. Note that one end of each fragment (except the 17.8 kb BssHII dystrophin fragment) detected is derived from the end of the linearized Ad5βdys genome (see FIG. 10). Low levels of shorter products, presumably derived from defective virions, become detectable only at high serial passage number.

At the later passages (9 and 12) there appeared to be an emergence of truncated Ad5βdys sequences, suggesting that deletions and/or rearrangements may be occurring at later passages. Hence, most experiments were performed with Ad5βdys EAMs derived from the earlier passages. The possibility of the emergence of replication competent (E1-containing) viruses was also examined by infection of HeLa cells by purified and crude serial lysates, none of which produced any detectable CPE.

b) Purification of Encapsidated Adenovirus Minichromosomes on CsCl Gradients

The ability to separate Ad5βdys EAMs from hpAP virions based on their buoyancy difference (due presumably to their different genome lengths) on CsCl gradients was examined. Repeated fractionation of the viral lysate allows small differences in buoyancy to be resolved. CsCl purification of encapsidated adenovirus minichromosomes was performed as follows. Approximately 25% of the lysate prepared from various passages during serial infections was used to purify virions. Freeze-thawed lysate was centrifuged to remove the cell debris. The cleared lysate was extracted twice with 1,1,2 tricholorotrifluoroethane (Sigma) and applied to CsCl step and self forming gradients.

Purification of virus was initially achieved by passing it twice through CsCl step gradients with densities of ρ=1.45 and ρ=1.20 in a SW28 rotor (Beckman). After isolation of the major band in the lower gradient, the virus was passed through a self forming gradient (initial ρ=1.334) at 37,000 rpm for 24 hrs followed by a relaxation of the gradient by reducing the speed to 10,000 rpm for 10 hrs. in a SW41 rotor (Beckman) at 12° C. [Anet and Strayer (1969) Biochem. Biophys. Res. Commun. 34:328]. The upper band from the gradient (composed mainly of Ad5βdys virions) was isolated using an 18 gauge needle, reloaded on a fourth CsCl gradient (ρ=1.334) and purified at 37,000 rpm for 24 hrs followed by 10,000 rpm for 10 hrs at 12° C.

The Ad5βdys-containing CsCl band was removed in 100 μl fractions from the top of the centrifugation tube and CsCl was removed by chromatography on Sephadex G-50 (Pharmacia). Aliquots from each fraction were used to infect 293 cells followed by β-galactosidase and alkaline phosphatase assays to quantitate the level of contamination by hpAP virions in the final viral isolate.

Figures 13A, 13B:
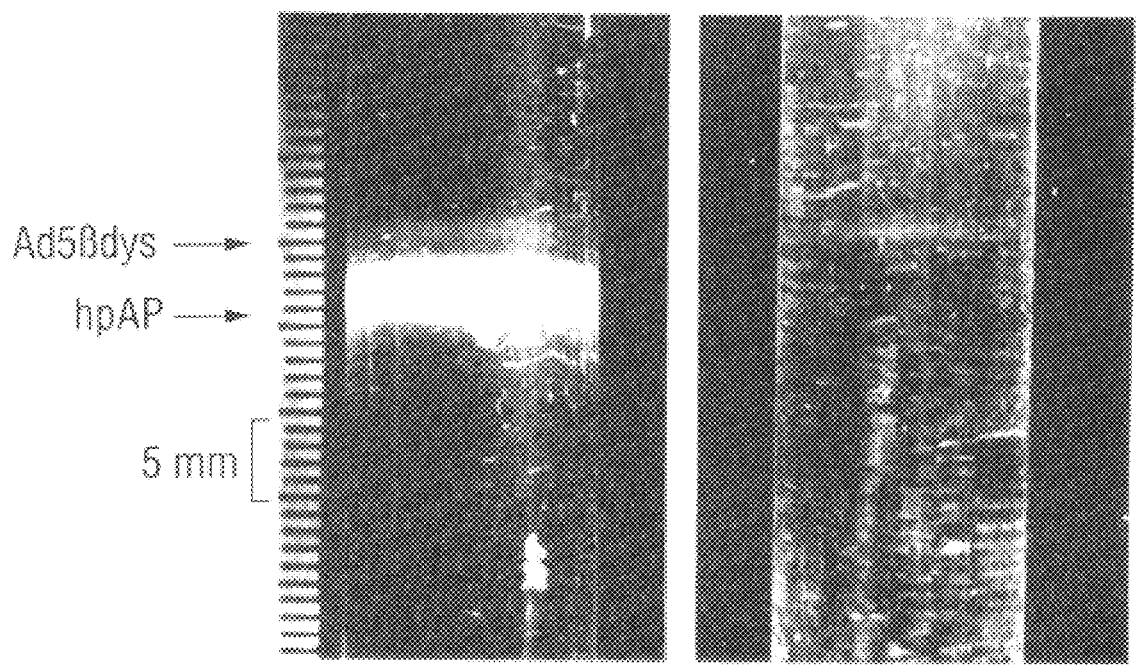
FIGS. 13A–B show the physical separation of Ad5βdys from hpAP virions at the third (A) and final (B) stages of CsCl purification.

Results of the physical separation between Ad5βdys EAMs and hpAP virions are shown in FIG. 13. FIG. 13 shows the physical separation of Ad5βdys from hpAP virions at the third (A) and final (B) stages of CsCl purification (initial p=1.334) in a SW41 tube. Aliquots of Ad5βdys EAMs from the final stage were drawn through the top of the centrifugation tube and assayed for β-galactosidase and alkaline phosphatase expression. Results of these assays are presented in FIG. 14.

Figure 14:
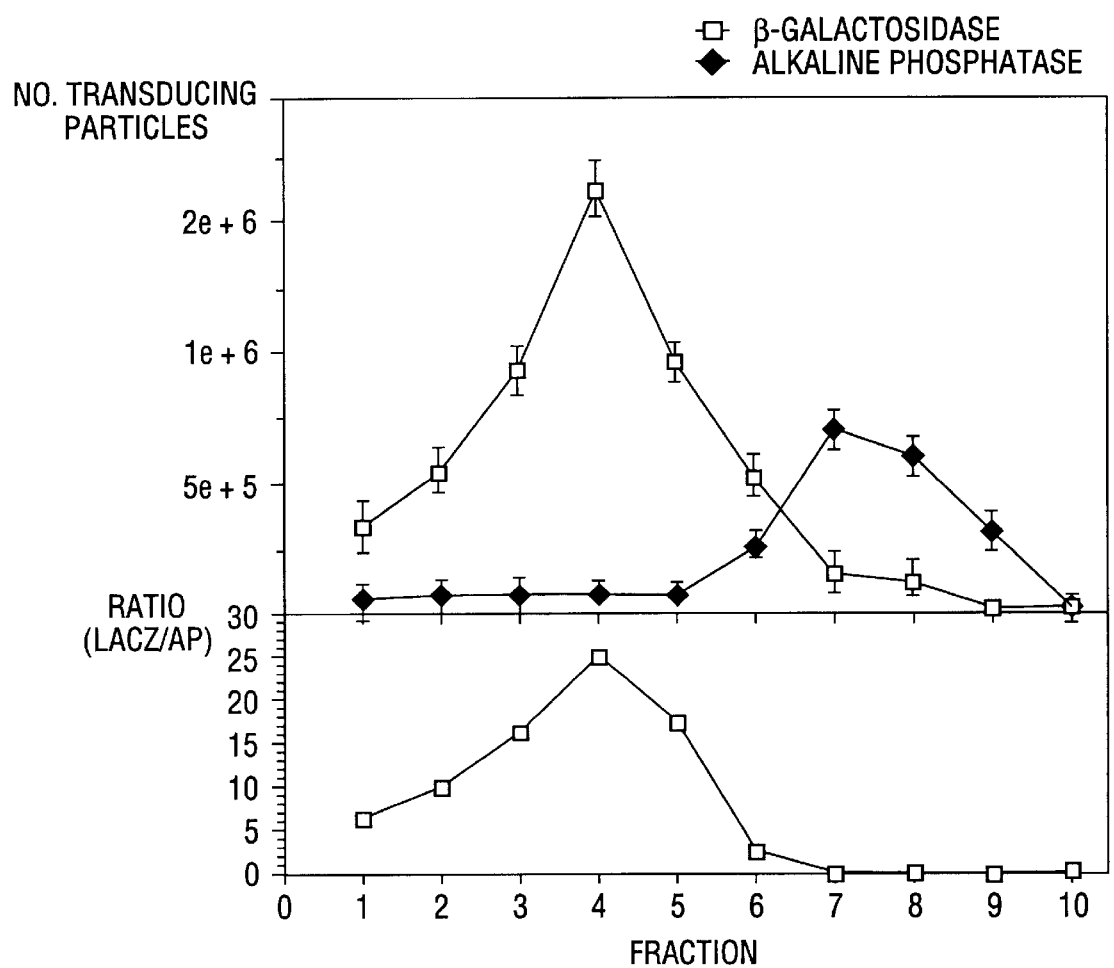
FIG. 14 graphically depicts the level of contamination of Ad5βdys EAMs by hpAP virions obtained from the final stage of CsCl purification as measured by β-galactosidase and alkaline phosphatase expression. The ratio of the two types of virions—Ad5βdys EAMs (LacZ) or hpAP (AP) in each fraction is indicated in the lower graph.

In FIG. 14, shows the level of contamination of Ad5βdys EAMs by hpAP virions obtained from passage 6. Following four cycles of CsCl purification, aliquots were removed from the top of the centrifugation tube and used for infection of 293 cells, which were fixed 24 hrs later and assayed for β-galactosidase or alkaline phosphatase activity (described below). The number of transducing particles are an underestimation of the actual totals as in some cases a positive cell may have been infected by more than one transducing particle. The ratio of the two types of virions—Ad5βdys EAMs (LacZ) or hpAP (AP) in each fraction is indicated in the lower graph.

The maximum ratio of transducing Ad5βdys EAMs to hpAP virions reproducibly achieved in this study was 24.8—a contamination with helper virus corresponding to approximately 4% of the final viral isolate.

c) Dystrophin and β-galactosidase Expression By Encapsidated Adenovirus Minichromosomes in Muscle Cells To determine if the Ad5βdys EAMs were able to express β-galactosidase and dystrophin in muscle cells, mouse myc myogenic cultures were infected with CsCl purified EAMs.

i) Propagation and Infection of Muscle Cells

MM14 and mdx myogenic cell lines were kindly provided by S. Hauschka (University of Washington) and were cultured as previously described [Linkhart et al. (1981) Dev. Biol. 86:19 and Clegg et al. (1987) J. Cell Biol. 105:949]. Briefly, myoblasts were grown on plastic tissue culture plates coated with a 0.1% gelatin in Ham's F-10 medium containing 15% (v/v) horse serum, 0.8 mM $CaCl_2$, 200 ng/ml recombinant human basic fibroblast growth factor (b-FGF) and 60 μg/ml genitimicin (proliferation medium). Cultures were induced to differentiate by switching to growth in the presence of growth medium lacking B-FGF and containing 10% horse serum (differentiation medium). Myoblasts or differentiated myotubes (three days post switching) were infected at a multiplicity of infection of 2.2 Ad5βdys EAMs per cell. Fractions containing minimal contamination with hpAP virions (3, 4 and 5 of passage 6) were used for western and immunofluorescence analysis. Infection was allowed to proceed for 3 days for both the myoblasts and myotubes before harvesting cells.

ii) Total Protein Extraction and Immunoblot Analysis

For protein extraction, muscle cells were briefly trypsinized, transferred to a microcentrifuge tube, centrifuged at 14 K for 3 min at room temp and resuspended two times in PBS. After an additional centrifugation, the cell pellet was resuspended in 80 μl of RIPA buffer (50 mM Tris-Cl, pH 7.5; 150 mM NaCl; 1% Nonidet P40; 0.5% sodium deoxycholate; 0.1% SDS) (Sambrook et al., supra). The sample was briefly sheared using a 22 gauge needle to reduce viscosity and total protein concentration assayed using the bicinconinic acid protein assay reagent (Pierce, Rockford, Ill.). Expression of full length dystrophin or β-galactosidase in infected mdx and MM14 myoblasts or myotubes was analyzed by electrophoresis of 40 μg of total protein extract on a 6% SDS-PAGE gel (in 25 mM Tris, 192 mM glycine, 10 mM β-mercaptoethanol, 0.1% SDS). After transferring to Gelman Biotrace NT membrane (in 25 mM Tris, 192 mM glycine, 10 mM β-mercaptoethanol, 0.05% SDS, 20% methanol), the membrane was blocked with 5% non-fat milk and 1% goat-serum in Tris-buffered saline-Tween (TBS-T) for 12 hrs at 4° C. Immunostaining was done according to the protocol for the ECL western blotting detection reagents (Amersham Life Sciences, Buckingham, UK). The primary antibodies used were Dys-2 (Vector Laboratories) and anti-β-galactosidase (BMB, Indianapolis, Ind.) with a horseradish peroxidase-conjugated anti-mouse secondary antibody.

Western blot analysis of EAM-infected mdx myoblasts and myotubes (three days post-fusion) indicated that EAMs were able to infect both of these cell types (FIG. 15). In FIG. 15, immunoblots of protein extracts from mdx myoblasts and myotubes demonstrating the expression of β-galactosidase (A) and dystrophin (B) in cells infected with Ad5βdys EAMs. Total protein was extracted 3 days post infection in all cases. Myotubes were infected at three days following a switch to differentiation media In FIG. 15A, lane 1 contains total protein extract from 293 cells infected with a virus expressing β-galactosidase as a control (RSV-LacZ); lanes 2–5 contain total protein extracts from uninfected mdx myoblasts, mdx myoblasts infected with Ad5βdys EAMs, mdx myotubes and mdx myotubes derived from mdx myoblasts infected with Ad5βdys EAMs, respectively. In FIG. 15B, lanes 1 and 7 contain total protein from mouse muscle ("C57") while lane 2 contains protein from wild type MM14 myotubes, as controls. Lanes 3–5 contain total protein extracts from uninfected mdx myoblasts, mdx myoblasts infected with Ad5βdys EAMs, mdx myotubes and mdx myotubes derived from mdx myoblasts infected with Ad5βdys EAMs, respectively.

As shown in FIG. 15, expression of β-galactosidase was detected in both the infected mdx myoblasts and myotubes indicating that the CMV promoter was active at both these early stages of differentiation in muscle cells. However, only infected mdx myotubes produced protein detected by dys-2, an antibody recognizing the 17 C-terminal amino acids of dystrophin (FIG. 15). No dystrophin expression was detected in infected myoblasts by western analysis, indicating that the muscle creatine kinase promoter functions minimally, if at all, within the Ad5βdys EAM prior to terminal differentiation of these cells.

Figure 16A:
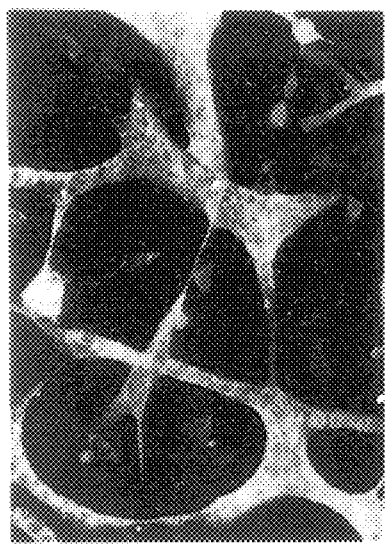
FIGS. 16A–C depict immunofluorescence of dystrophin expression in wild type MM14 myotubes (A), uninfected mdx (B) and infected mdx myotubes (C).
Figure 16B:
Figure 16C:
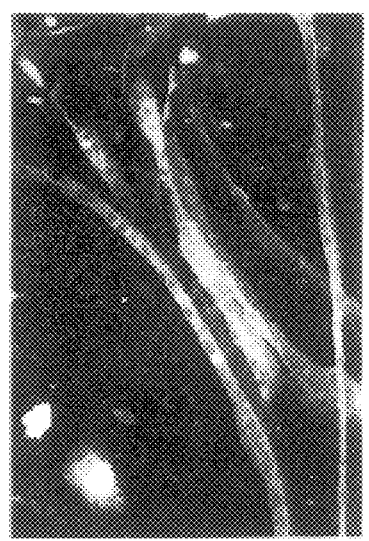

Dystrophin expression in mdx cells infected with EAMs was confirmed by immunofluorescence studies using N-terminal dystrophin antibodies. In agreement with the western analysis, dystrophin expression from the MCK promoter was detected only in differentiated mdx myotubes infected by Ad5βdys EAMs (FIG. 16). FIGS. 16A–C show immunofluorescence of dystrophin in wild type MM14 myotubes (A), uninfected mdx (B) and infected mdx myotubes (C), respectively. The results shown in FIG. 16 demonstrate the transfer and expression of recombinant dystrophin to differentiated mdx cells by Ad5βdys EAMs.

Immunofluorescence of myogenic cells was performed as follows. Approximately $1.5 \times 10^6$ MM14 or mdx myoblasts were plated on Poly-L-lysine (Sigma) coated glass slides (7×3 cm) which had been previously etched with a 0.05% chromium potassium sulfate and 0.1% gelatin solution. For myotube analysis, the cultures were switched to differentiation media [Clegg et al. (1987), supra] 48 hours after plating, immediately infected and then allowed to fuse for 3 days, whereas myoblasts were continuously propagated in proliferation media [Clegg et al. (1987), supra]. Cells were washed three times with PBS at room temperature and fixed in 3.7% formaldehyde. For immunostaining, cells were incubated in 0.5% Triton X-100, blocked with 1% normal goat serum and incubated with an affinity purified antibody against the N-terminus of murine dystrophin for 2 hrs. followed by extensive washing in PBS and 0.1% Tween-20 with gentle shaking. Cells were incubated with a 1:200 dilution of biotin conjugated anti-rabbit antibody (Pierce) for one hour and washed as above. Cells were further incubated with a 1:300 dilution of streptavidin-fluorescein isothiocyanate conjugate (Vectorlabs, Burlingam, Calif.) for one hour and washed as above, followed by extensive washing in PBS.

The above results show that embedded inverted Ad origins of replication coupled to an encapsidation signal can convert circular DNA molecules to linear forms in the presence of helper virus and that these genomes can be efficiently encapsidated and propagated to high titers. Such viruses can be purified on a CsCl gradient and maintain their ability to transduce cells in vitro, and their increased cloning capacity allows the inclusion of large genes and tissue specific gene regulatory elements. The above results also show that the dystrophin gene was expressed in cells transduced by such viruses and that the protein product was correctly localized to the cell membrane. The above method for preparing EAMs theoretically enables virtually any gene of interest to be inserted into an infectious minichromosome by conventional cloning in plasmid vectors, followed by cotransfection with helper viral DNA in 293 cells. This approach is useful for a variety of gene transfer studies in vitro. The observation that vectors completely lacking viral genes can be used to transfer a full-length dystrophin cDNA into myogenic cells indicates that this method may be used for the treatment of DMD using gene therapy.

d) A Modified MCK Enhancer Increases Expression of Linked Genes In Muscle

The DNA fragment containing enhancer/promoter of the MCK gene utilized in the Ad5βdys EAM plasmid is quite large (~3.3. kb). In order to provide a smaller DNA fragment capable of directing high levels of expression of linked genes in muscle cells, portions of the 3.3 kb MCK enhancer/ promoter were deleted and/or modified and inserted in front of a reporter gene (lacZ). The enhancer element of the MCK gene was modified to produce the 2RS5 enhancer; the sequence of the 2RS5 enhancer is provided in SEQ ID NO:10. The first 6 residues of SEQ ID NO:10 represent a KpnI site added for ease of manipulation of the modified MCK enhancer element. Residue number 7 of SEQ ID NO:10 corresponds to residue number 2164 of the wild-type MCK enhancer sequence listed in SEQ ID NO:9 (position 2164 of SEQ ID NO:9 corresponds to position –1256 of the MCK gene). Residue number 174 of SEQ ID NO:10 corresponds to residue number 2266 of the wild-type MCK enhancer sequence listed in SEQ ID NO:9.

Figure 17:
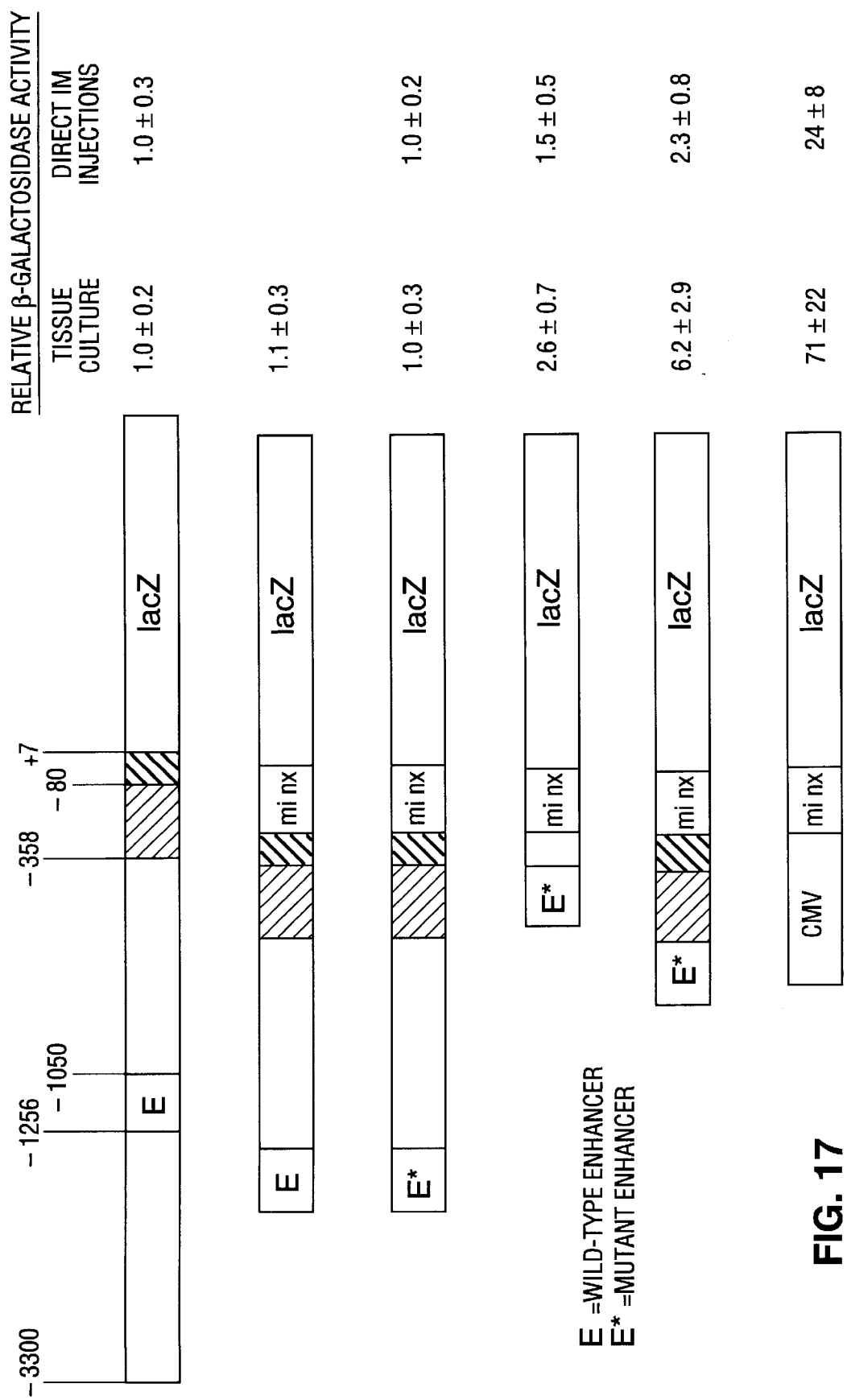
FIG. 17 is a schematic representation of the MCK/lacZ constructs tested to determine what portion of the ~3.3 kb DNA fragment containing the enhancer/promoter of the MCK gene is capable of directing high levels of expression of linked genes in muscle cells.

These MCK/lacZ constructs were used to transfect cells in culture (i.e., myogenic cultures) or were injected as naked DNA into the muscle of mice and β-galactosidase activity was measured. FIG. 17 provides a schematic of the MCK/ lacZ constructs tested. The first construct shown in FIG. 17 contains the 3.3. kb wild-type MCK enhancer/promoter fragment linked to the *E. coli* lacZ gene. The wild-type enhancer element (–1256 to –1056) is depicted by the box containing "E"; the core promoter element (–358 to –80) is indicated by the light cross-hatching and the minimal promoter element (–80 to +7) is indicated by the dark cross-hatching. The core promoter element is required in addition to the minimal promoter element (which is required for basal expression) in order to achieve increased muscle-specific expression in tissue culture [Shield et al. (1996) Mol. Cell. Biol. 16:5058]. The modified enhancer element, the 2RS5 enhancer, is indicated by the box labeled "E*." The box labeled "mi nx" contains a synthetic intron derived from adenovirus and is used to increase expression of the constructs (any intron may be utilized for this purpose). The box labeled "CMV" depicts the CMV IE enhancer/promoter which was used a positive control.

In FIG. 17, β-galactosidase activity is expressed relative to the activity of the wild-type MCK enhancer/promoter construct shown at the top of the figure. As shown in FIG. 17, a construct containing the 2RS5 enhancer (SEQ ID NO:10) linked to either the minimal MCK promoter (a ~261 bp element) or the core and minimal MCK promoter elements (a ~539 bp element) directs higher levels of expression of the reporter gene in muscle cells as compared to the ~3.3 kb fragment containing the wild-type enhancer element. These modified enhancer/promoter elements are considerably smaller than the ~3.3 kb fragment used in the Ad5βdys EAM plasmid and are useful for directing the expression of foreign genes in muscle cells. These smaller elements are particularly useful for driving the expression of genes in the context of self-propagating adenoviral vectors which have more severe constraints on the amount of foreign DNA which can be inserted in comparison to the use of "gutted" adenoviruses such as the EAMs described above.

EXAMPLE 7

Generation of High Titer Stocks of Encapsidated Adenovirus Minichromosomes Containing Minimal Helper Virus Contamination The results presented in Example 6 demonstrated that encapsidated adenovirus minichromosomes (EAMs) can be prepared that lack all viral genes and which can express full-length dystrophin cDNAs in a muscle specific manner. The propagation of these EAMs requires the presence of helper adenoviruses that contaminate the final EAM preparation with conventional adenoviruses (about 4% of the total preparation). In this example the EAM system is modified to enable the generation of high titer stocks of EAMs with minimal helper virus contamination. Preferably the EAM stocks contain helper virus representing less than 1%, preferably less than 0.1% and most preferably less than 0.01% of the final viral isolate. Purified EAMs are then injected in vivo in muscles of dystrophin minus mdx mice to determine whether these vectors lead to immune rejection and whether they can alleviate dystrophic symptoms in mdx muscles.

The amount of helper virus present in the EAM preparations is reduced in two ways. The first is by selectively controlling the relative packaging efficiency of the helper virus versus the EAM virus. The second is to improve physical methods for separating EAM from helper virus. These approaches enable the generation of dystrophin-expressing EAMs that are contaminated with minimal levels of helper virus.

a) Development and Characterization of Adenovirus Packaging Cell Lines Expressing the Cre Recombinase From Bacteriophage P1

Cell lines expressing a range of Cre levels are used to optimize the amount of helper virus packaging that occurs during growth of the EAM vectors. The Cre-loxP system [Sauer and Henderson (1988) Proc. Natl. Acad. Sci. U.S.A. 85:5166] is employed to selectively disable helper virus packaging during growth of EAMS. The bacterial Cre recombinase catalyzes efficient recombination between a 34 bp target sequence called loxP. To delete a desired sequence, loxP sites are placed at each end of the sequence to be deleted in the same orientation; in the presence of Cre recombinase the intervening DNA segment is efficiently excised.

Cell lines expressing a range of Cre recombinase levels are generated. The expression of too little Cre protein may result in high levels of helper virus being generated, which leads to unacceptably high levels of helper virus contaminating the final EAM preparation. If very high levels of Cre expression are present in a cell line, excision of the packaging signal from the helper virus would be 100% efficient (i.e., it would completely prevent helper virus packaging). As shown in Example 6, serial passage of EAM preparations containing low levels of helper virus increased the titer of the EAM. Therefore, it is desirable, at least in the initial passages of a serial passage that some helper virus capable of being packaged is present. A low level of packagable helper virus may be provided by using a cell line expressing levels of Cre recombinase which are not high enough to achieve excision of the packaging signals from 100% of the helper virus; these cell lines would be used early in the serial passaging of the EAM stock and a cell line expressing high enough levels of Cre recombinanse to completely prevent helper virus packaging would be used for the final passage.

Alternatively, EAMs may be prepared using a packaging cell line that supports high efficiency Cre recombinase-mediated excision of the packaging signals from the helper virus by transfection of the Cre-expressing cell line with the EAM plasmid followed by infection of these cells with loxP-containing helper virus using an MOI of $\geq 1.0$.

Human 293 cell lines that express a variety of levels of Cre recombinase are generated as follows. An expression vector containing the Cre coding region, pOG231, was cotransfected into 293 cells along with pcDNA3 (Invitrogen); pcDNA3 contains the neo gene under the control of the SV40 promoter. pOG231 uses the human CMV enhancer/promoter [derived from CDM8 (Invitrogen)] to express a modified Cre gene [pOG231 was obtained from S. O'Gorman]. The modified Cre gene contained within pOG231 has had a nuclear localization signal inserted into the coding region to increase the efficiency of recombination.

pOG231 was constructed as follows. A BglII site was introduced into the 5' XbaI site of the synthethic intron of pMLSISCAT [Haung and Gorman (1990) Nucleic Acids Res. 18:937] by linker tailing. A BglII site in the synthethic intron of pMLSISCAT was destroyed and a BamHI linker was inserted into the PstI site at the 3' end of the synthethic intron in pMLSISCAT. BglII and SmaI sites and a nuclear localization signal were introduced into the 5' end of pMC-Cre [Gu et al. (1993) Cell 73:1155] using a PCR fragment that extended from the novel BglII and SmaI sites to the BamHI site in the Cre coding region. This PCR fragment was ligated to a BamHI/SalI fragment containing a portion of the Cre coding region derived from pLC-Cre (Gu et al., supra) and the intron plus Cre coding sequence was inserted into a modified form of pOG44 [O'Gorman et al. (1991) Science 251:1351] to generate pOG231. The predicted sequence of pOG231 from the BglII site to the BamHI site located in the middle of the Cre coding sequence is listed in SEQ ID NO:11.

One 60 mm dish of 293 cells (Microbix) were transfected with 10 μg of PvuII-linearized pOG231 and 1 μg of NotI-linearized pcDNA3 using a standard calcium phosphate precipitation protocol. Two days after the addition of DNA, the transfected cells were split into three 100 mm dishes and 1000 μg/ml of active G418 was added to the medium. The cells were fed periodically with G418-containing medium and three weeks later, 24 G418-resistant clones were isolated.

Figure 18:
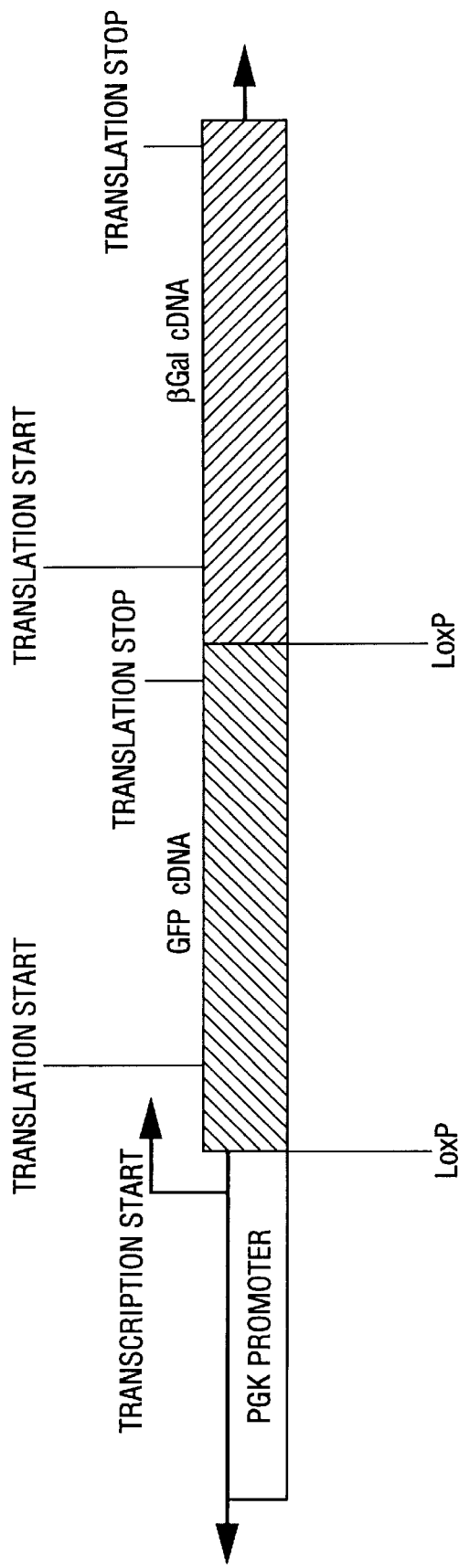
FIG. 18 is a schematic representation of a GFP/β-gal reporter construct suitable for assaying the expression of Cre recombinase in mammalian cells.

The isolated clones were expanded for testing. Aliquots were frozen in liquid nitrogen at the earliest possible passage. The neomycin resistant cell lines were examined for the expression of Cre recombinase using the following tansfection assay. The neomycin resistant cells were transfected with PGK-1-GFP-lacZ (obtained from Sally Camper, Univ. of Michigan, Ann Arbor, Mich.), which contains a green fluorescent protein (GFP) expression cassette that can be excised by Cre recombinase to allow expression of β-galactosidase; transfection was accomplised using standard calcium phosphate precipitation. FIG. 18 provides a schematic of a GFP/β-gal reporter construct suitable for assaying the expression of Cre recombinase in mammalian cells; GFP sequences and β-gal (i.e., lacZ) sequences are available from commercial sources (e.g., Clonetech, Palo Alto, Calif. and Pharmacia Biotech, Piscataway, N.J., respectively).

Control experiments verified that 293 cells transfected with PGK-1-GFP-lacZ expressed significant amounts of β-galactosidase only if these cells also expressed Cre recombinanse. β-galactosidase assays were performed as described in Example 6. Neomycin resistant cells expressing Cre recombinase were grouped as high, medium or low expressors based upon the amount of β-galactosidase activity produced (estimated by direct counting of β-galactosidase-positive cells per high-power field and by observing the level of staining and the rapidity with which the blue stain was apparent) when these cell lines were transfected with the GFP/β-gal reporter construct. Thirteen positive (i.e., Cre-expressing) lines, D608#12, #7, #22, #18, #17, #4, #8, #2, #2/2, #13, #5, #15 and #21 were retained for further use.

The results of this transfection analysis revealed that cultures of 293 cells expressing medium to high levels of Cre recombinase could be generated without apparent toxicity.

b) Generation of Helper Adenovirus Strains that Contain loxP Sites Flanking the Adenovirus Packaging Signals Studies of EAM production demonstrated that the EAM vector has a packaging advantage over the helper adenovirus (Ex. 6). While not limiting the present invention to a particular mechanism, it is hypothesized that this packaging and replication advantage can be greatly increased by using helper viruses that approach the packaging size limits of Ad5 [Bett el al. (1993) J. Virol. 67:5911], by using viruses with mutations in E4 and/or E2 genes [Yeh et al. (1996) J. Virol. 70:559; Gorziglia et al. (1996) J. Virol. 70:4173; and Amalfitano et al. (1996) Proc. Natl. Acad. Sci. U.S.A. 93:3352], by inclusion of mutations or alterations in the packaging signals of the helper virus [Imler et al. (1995) Hum. Gene Ther. 6:711] and by combining these strategies.

The Cre-loxP excision method is used to disable the packaging signals from the helper virus genomes. The Ad5 packaging domain extends from nucleotide 194 to 358 and is composed of five distinct elements that are functionally redundant [Hearing et al. (1987) J. Virol. 61:2555]. Theoretically, any molecule containing the Ad5 origin of replication and packaging elements should replicate and be packaged into mature virions in the presence of non-defective helper virus. Disabling the packaging signals should allow replication and gene expression to proceed, but will prevent packaging of viral DNA into infectious particles. This in turn should allow the ratio of EAM to helper virus to be increased greatly.

To disable the packaging signals within the helper virus used to encapsidate the EAMs, the loxP sequences are incorporated into a helper virus that has a genome approaching the maximal packaging size for Ad [~105 map units; Bett et al. (1993), supra] which further decreases the efficiency of helper virus packaging. Final virus size can be adjusted by the choice of introns inserted into the reporter gene, by the choice of reporter genes, or by including a variety of DNA fragments of various sizes to act as "stuffer" fragments. A convenient reporter gene is the alkaline phosphatase gene (see Ex. 6). The optimized Cre-loxP system is also incorporated into a helper viral backbone containing disruptions of any or all of the E1–E4 genes. Use of such deleted genomes requires viral growth on appropriate complementing cell lines, such as 293 cells expressing E2, and/or E4 gene products. The loxP sequences are incorporated into the helper virus by placing the loxP sequences on either side of the packaging signals on a shuttle vector. This modified shuttle vector is then used to recombine with the Ad DNA derived from a virus containing disruptions of any or all of the E1–E4 genes to produce the desired helper virus containing the packaging signals flanked by loxP sequences.

pAdBglII, an adenovirus shuttle plasmid containing Ad sequences from 0–1 and 9–16 map units (mu) was used as the starting material. Synthetic oligonucleotides were used to create a polylinker which was inserted at 1 mu within pAdBglII as follows. The BglII LoxP oligo [5'-GAAGATCTATAACTTCGTATAATGTATGCTATACGAAGTTATTACCGAAGAAATGGCTCGAGATCTTC-3' (SEQ ID NO:12) and its reverse complement [5'-GAAGATCTCGAGCCATTTCTTCGGTAATAACTTCGTATAGCATACATTATACGAAGTTATAGATCTTC-3' (SEQ ID NO: 13)] were synthesized. The AflIII LoxP oligo [5'-CCACATGTATAACTTCGTATAGCATACATTATACGAAGTTATACATGTGG-3' (SEQ ID NO:14)] and its reverse complement [5'-CCACATGTATAACTTCGTATAATGTATGCTATACGAAGTTATACATGTGG-3' (SEQ ID NO:15)] were synthesized. The double stranded form of each loxP oligonuceotide was digested with the appropriate restriction enzyme (e.g., BglII or AflIII) and inserted into pAdBglII which had been digested with BglII and AflIII. This resulted in the insertion of LoxP sequences into the shuttle vector flanking the packaging signals that are located between 0.5 and 1 mu of Ad5 (one mu equals 360 bp in the Ad5 genome; the sequence of the Ad5 genome is lsited in SEQ ID NO:1). The 3' loxP sequence was inserted into the BglII site within pAdBglII. The 5' loxP sequence was inserted into the AflIII site located at base 143 (~0.8 mu) (numbering relative to Ad5).

DNA sequencing was used to verify the final structure of the modified shuttle plasmid between 0–1 mu. If Cre recombinase-mediated excision of the packaging signals is found to be too efficient (as judged by the production of too little helper virus), alternate sites for the insertion of the loxP sequences are used that would result in deletion of 2, 3 or 4 packaging sequences rather than all 5 [Grable and Hearing (1990) J. Virol. 64:2047]. The insertion of loxP sequences at sites along the Ad genome contained within the shuttle vector which would result in the deletion of 2, 3 or 4 packaging sequences are easily made using the technique of recombinant PCR [Higuchi (1990) In: *PCR Protocols: A Guide to Methods and Applications*, Innis et al. (eds.) Academic Press, San Diego, Calif., pp. 177–183]. The optimal amount of Cre recombinase-mediated excision of the packaging signals is that amount which permits the production of enough packaged helper virus to permit the slow spread of virus on the first plate of cells co-transfected with helper virus DNA (containing the loxP sequences) and the EAM vector. This permits serial passage of the EAM preparation onto a subsequent lawn of cells to increase the titer of the EAM preparation. Alternatively, if Cre recombinase-mediated excision of the packaging signals is essentially 100% efficient in all Cre-expressing cells lines (i.e., regardless of the level of Cre-expression, that is even a cell line expressing a low level of Cre as judged by the GFP/β-gal assay described above), the packaged EAMs may be used along with helper virus (used at a MOI of ~1.0) to infect the second or subsequent lawn of cells to permit serial passaging to increase the titer of the EAM preparation.

Following introduction of the loxP sequences into the shuttle vector, the human placental alkaline phosphatase (HpAp) cDNA under control of the RSV promoter was inserted into the polylinker to provide a reporter gene for the helper virus. This is the same reporter used previously during EAM generation (Ex. 6). The HpAp sequences were inserted as follows. The loxP-containing shuttle vector was linearized with XhoI and the hpAp cassette was ligated into the XhoI site (a XhoI site was inserted into pAdBglII during the insertion of the loxP sequences as a XhoI site was located on the 3' end of the loxP sequences inserted into the BglII site of pAdBglII). The HpAp cassette was constructed as follows. pRSVhAPT40 (obtained from Gary Nabel, Univ. of Michigan, Ann Arbor, Mich.) was digested with EcoRI to generate an EcoRI fragment containing the HpAP cDNA and the SV40 intron and polyadenylation sequences. pRc/RSV (Invitrogen) was digested with HindIII, then partially digested with EcoRI. A 5,208 bp fragment was then size selected on an agarose gel, treated with calf alkaline phosphatase, and ligated to the EcoRI fragment derived from pRSVhAPT40 to generate pRc/RSVAP. pRc/RSVAP was then digested with SalI and XhoI to liberate the RSV promoter linked to the HpAP cDNA cassette (including the SV40 intron and polyadenylation sequences). This SalI-XhoI fragment was inserted into the loxP-containing shuttle vector which had been digested with SalI and XhoI to generate pADLoxP-RSVAP.

Figure 19:
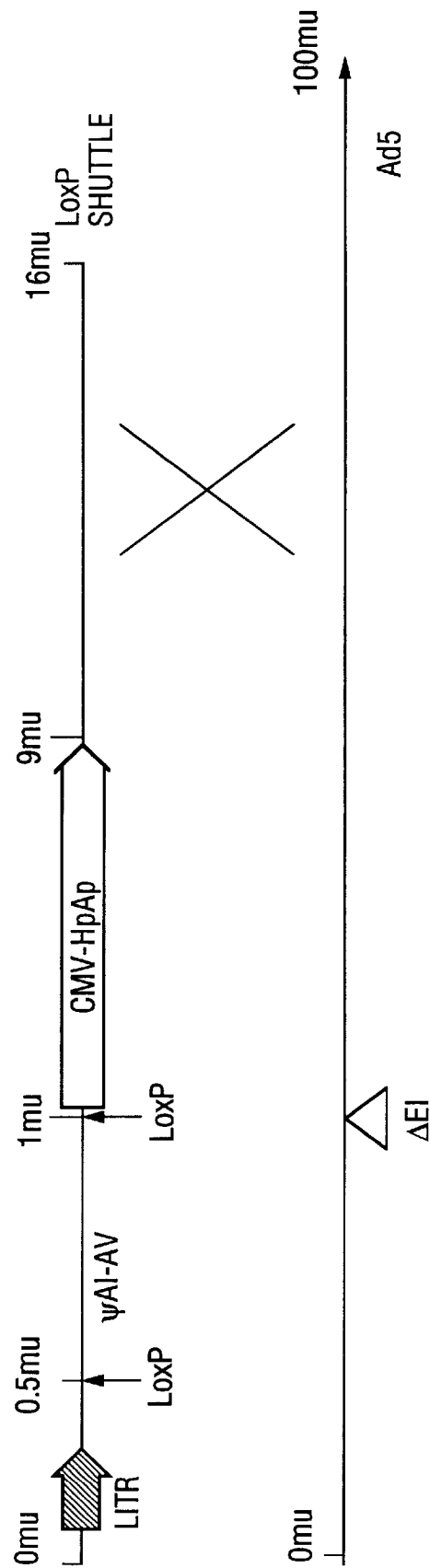
FIG. 19 is a schematic representation of the recombination event between the loxP shuttle vector and the Ad5dl7001 genome.

Helper virus containing loxP sites flanking the Ad packaging signals is generated by co-transfection of the LoxP shuttle plasmid (pADLoxP-RSVAP) and ClaI-digested Ad5dl7001 DNA into 293 cells [Graham and Prevec (1991) Manipulation of Adenovirus Vectors, In *Methods in Molecular Biology*, Vol. 7: *Gene Transfer and Expression Protocols*, Murray (ed.), Humana Press Inc., Clifton, N.J., pp. 109–128]. FIG. 19 provides a schematic showing the recombination event between the loxP shuttle vector and the Ad5dl7001 genome. Co-transfection is carried out as described in Example 3c.

Alternatively, the reporter gene may be inserted into the E3 region of pBHG10 or pBHG11 (using the unique PacI site) rather than into the polylinker located in the E1 region of the shuttle vector. The reporter gene-containing pBHG10 or 11 is then used in place of Ad5dl7001 for cotransfection of 293 cells along with the loxP-containing pAdBglII.

Following cotransfection, recombinant plaques are picked, plaque purified, and tested for incorporation of both hpAp and loxP sequences by PCR and Southern analysis (Ex. 3). Viruses which contain loxP sites flanking the packaging signals and the marker gene (hpAp) are retained, propagated and purified.

The isolated helper virus containing loxP sites flanking the packaging signals and the marker gene is then used to infect both 293 cells and the 293 cell lines that express Cre (section a, above). Cre recombinase-expressing cell lines that produce optimal levels of Cre recombinase when infected with the loxP-containing helper virus are then used for the generation of EAMs as described below.

c) Generation of Encapsidated Adenovirus Minichromosomes that Express Dystrophin The growth of EAMs is optimized using the following methods. In the first method, plasmid DNA from the EAM vector (Ex. 6) are co-transfected into 293 cells with purified viral DNA from the helper virus, and viruses are harvested 10–14 days later after appearance of a viral cytopathic effect (CPE) as described in Example 6. This approach is simple, yet potentially increases helper Virus levels by allowing viral spread throughout the culture dishes.

In the second method, the co-transfected 293 cells are overlaid with agar and single plaques are picked and tested for EAM activity by the ability to express β-galactosidase activity following infection of Hela cells (Ex. 6). This second approach is more time consuming, but will result in less contamination by helper.

The ability of these two methods to generate EAMs are directly compared. The preferred method is that which produces the highest titer of EAM with the lowest contamination of helper virus. The efficiency of EAM generation may also be increased by using helper virus DNA that retains the terminal protein (TP) (ie., the helper virus is used as a viral DNA-TPC as described in Ex. 3) The use of viral DNA-TPC has been shown to increase the efficiency of viral production following transfection of 293 cells by an order of magnitude [Miyake et al. (1996), supra].

The initial transfection will utilize 293 cells that do not express Cre recombinase, so that efficient spread of the helper can lead to large scale production of EAM. The method producing the highest ratio of EAM to helper virus is then employed to optimize conditions for the serial propagation of the EAM on 293 cells expressing Cre recombinase. This optimization is conducted using cell lines expressing different levels of Cre recombinase. The following variables are tested: 1) the ratio of input viral titer to cell number, 2) the number of serial passages to use for EAM generation, 3) the use of cell lines producing different levels of Cre to achieve the optimal ratio between high EAM titer and low helper titer, 4) continuous growth on Cre-producing 293 cells versus alternating between Cre-producing cells and the parental 293 cells, or to alternate between high and low Cre-producing cells and 5) CsCl purification of EAMs prior to re-infection of 293 cells increases the ratio of the final EAM/helper titers. The protocols that result in the highest yield of EAM with minimal helper virus are used to generate large volumes of crude viral lysates for purification by density gradient centrifugation (Ex. 6).

EAMs were purified from helper virus using standard CsCl density gradient centrifugation protocols in Example 6 and resulted in preparations containing ~4% helper virus. In order to improve the physical separation of EAMs and helper virus, a variety of different centrifugation conditions are possible, including changing the gradient shape, type of rotor and tube used, combinations of step and continuous gradients, and the number of gradients used. Materials with better resolving powers than CsCl can also be employed. These include rubidium chloride and potassium bromide [Reich and Zarybnicky (1979) Annal. Biochem. 94:193].

d) Use of EAMs Encoding Dystrophin For Long Term Expression of Dystrophin in Muscle To demonstrate the ability of the purified dystrophin expressing EAMs (prepared as described above) to deliver and express dystrophin in the muscle of an animal, the following experiment is conducted. First, purified dystrophin-EAMs are delivered to the muscle by direct intramuscular injection into newborn, 1 month, and adult (3 month) mouse quadriceps muscle. The dystrophin expressing EAM Ad5βDys are injected into mdx mice and into transgenic mdx mice that express β-galactosidase in the pituitary gland [Tripathy et al. (1996) Nature Med. 2:545]. These latter mice are used to avoid potential immune-rejection of cells expressing β-galactosidase from the Ad5βDys vector. An alternate EAM lacking the β-galactosidase reporter gene may also be employed; however, the presence of the β-Gal reporter simplifies EAM growth and purification (vectors lacking β-Gal have their purity estimated by PCR assays rather than by β-Gal assays).

Following intramuscular injection of EAM, animals are sacrificed at intervals between 1 week and 6 months to measure dystrophin expression [by western blot analysis and by immunofluorescence (Phelps et al. (1995) Hum. Mol. Genet. 4:1251 and Rafael et al. (1996) J. Cell Biol. 134:93] and muscle extracts will also be assayed for β-Gal activity [MacGregor et al. (1991), supra]. These results are compared with previous results obtained using current generation viral vectors (i.e., containing deletions in E1 and E3 only) to demonstrate that EAMs improve the prospects for long term gene expression in muscle.

e) Use of Dystrophin-EAMs to Prevent, Halt, or Reverse the Dystrophic Symptoms that Develop in the Muscles of mdx Mice To demonstrate that beneficial effects on dystrophic muscle are achieved by delivery of dystrophin expressing EAMs to mdx mice, the following experiments are conducted. Central nuclei counts are performed on soleus muscle at intervals following injection of EAM into newborn, 1 month, and 3 month (adult) mice (Phelps et al., 1995). Central nuclei arise in mouse muscle only after a myofiber has undergone dystrophic necrosis followed by regeneration, and is a quantitative measure of the degree of dystrophy that has occurred in a muscle group (Phelps et al, 1995).

More informative assays are also contemplated. These assays require administration of EAMs to mouse diaphragm muscles.

The diaphragm is severely affected in mdx mice (Stedman et al., 1991; Cox et al., 1993), and displays dramatic decreases in both force and power generation. Administration of virus to the diaphragm will allow the strength of the muscles to be measured at intervals following dystrophin delivery. The force and power generating assays developed by the Faulkner lab are used to measure the effect of dystrophin transgenes (Shrager et al., 1992; Rafael et al., 1994; Lynch et al., 1996).

To determine whether dystrophin delivery to dystrophic muscle reverses dystrophy or stabilizes muscle, varying amounts of the dystrophin EAM are delivered to the to diaphragm at different stages of the dystrophic process and then strength is measured at intervals following EAM administration. First, various titers of EAM are tested to determine the minimal amount of virus needed to transduce the majority of muscle fibers in the diaphragm. It has been shown that conventional adenovirus vectors can transduce the majority of diaphragm fibers when $10^8$ pfu are administrated by direct injection into the intraperitoneal cavity [Huard et al. (1995) Gene Therapy 2:107]. In addition, it has been shown that transduction of a simple majority of fibers in a muscle group is sufficient to prevent virtually all the dystrophic symptoms in mice [Rafael et al. (1994) Hum. Mol. Genet. 3:1725 and Phelps et al. (1995) Hum. Mol. Genet. 4:1251]. Virus is administered to mdx animals at three different ages (neonatal, 1 month, and 3 months). Animals are sacrificed for physiological analysis of diaphragm muscle at two different times post infection (1 month and 3 months). Error control is achieved by performing these experiments in sextuplicate. Control animals consist of mock injected wild-type (C57B1/10) and dystrophic (mdx) mice. Three month old mdx mice display a 40% reduction in force and power generation compared with wild-type mice, while 6 month animals display a greater than 50% reduction (Cox et al. (1993) Nature 364:725; Rafael et al. (1994), supra; Phelps et al. (1995), supra; and Corrado et al. (1996) J. Cell. Biol. 134:873].

EXAMPLE 8

Improved Shuttle Vectors for the Production of Helper Virus Containing LoxP Sites In the previous example, a shuttle vector containing adenoviral sequences extending from 9 mu to 16 mu of the Ad5 genome was modified to contain loxP sequences surrounding the packaging signals (the LoxP shuttle vector). This modified shuttle vector was then recombined with an Ad virus to produce a helper virus containing the loxP sequences. This helper virus was then used to infect cells expressing Cre recombinase along with DNA comprising a minichromosome containing the dystrophin gene, a reporter gene and the packaging signals and ITRs of Ad in order to preferentially package the minichromosomes. Using this approach the helper virus, which has had the packaging signals removed by Cre-loxP recombination, contains the majority of the Ad genome (only a portion of the E3 region is deleted). Thus, if low levels of helper virus are packaged and appear in the EAM preparation, the EAM preparation has the potential of passing on helper virus capable of directing the expression of Ad proteins in cells which are exposed to the EAM preparation. The expression of Ad proteins may lead to an immune response directed against the infected cells.

Another approach to reducing the possibility that the EAM preparation contains helper virus capable of provoking an immune response is to use helper viruses containing deletions and/or mutations within the pol and pTP genes. Helper virus containing a deletion in the pol and/or pTP genes is cotransfected with the EAM construct into 293-derived cell lines expressing pol or pol and pTP to produce EAMs. Any helper virus present in the purified EAM preparation will be replication defective due to the deletion in the pol and/or pTP genes. As shown in Example 3, viruses containing a deletion in the pol gene are incapable of directing the expression of viral late genes; therefore, helper viruses containing a deletion in the pol gene or the pol and pTP genes should not be capable of provoking an immune response (i.e., a CTL response) against late viral proteins synthesized de novo. Shuttle vectors containing deletions within the Ad pol and/or pTP genes are constructed as described below.

a) Construction of a Shuttle Vector Containing the Δpol Deletion pAdBglII was modified to contain sequences corresponding to 9 to 40 mu of the Ad5 genome as follows. pAdBglII was digested with BglII and a linker/adapter containing an AscI site was added to create pAdBglIIAsc. pAdBgulIIAsc was then digested with Bst1107I. Ad5dl7001 viral DNA was digested with AscI and the ends were filled in using T4 DNA polymerase. The AscI-digested, T4 DNA polymerase filled Ad5dl7001 viral DNA was then digested with Bst1107I and the ~9.9 kb AscI-Bst1107I(filled) fragment containing the pol and pTP genes was isolated (as described in Ex. 3) and ligated to the Bst1107I-digested pAdBglIIAsc to generate pAdAsc. pAdAsc is a shuttle vector which contains the genes encoding the DNA polymerase and preterminal protein (the inserted AscI-Bst1107I fragment corresponds to nucleotides 5767 to 15, 671 of the Ad5 genome).

A shuttle vector, pAdAscΔpol, which contains the 612 bp deletion in the pol gene (described in Ex. 3) was constructed as follows. Ad5ΔpolΔE3I viral DNA (Ex. 3) was digested with AscI and the ends were filled in using T4 DNA polymerase. The AscI-digested, T4 DNA polymerase filled Ad5ΔpolΔE3I viral DNA was then digested with Bst1107I and the ~9.3 kb AscI-Bst1107I(filled) fragment containing the deleted pol gene and the pTP gene was isolated (as described in Ex. 3) and ligated to Bst11071-digested pAd-BglIIAsc to generate pAdAscΔpol.

b) Construction of a Shuttle Vector Containing the ΔpolΔpTP Deletion

A shuttle vector, pAdAscΔpolΔpTP, which contains a 2.3 kb deletion within the pol and pTP genes (described in Ex. 5) was constructed as follows. pAXBΔpolΔpTPVARNA+t13 (Ex. 5b) was digested with AscI and the ends were filled in using T4 DNA polymerase. The AscI-digested, T4 DNA polymerase filled pAXBΔpolΔpTPVARNA+t13 DNA was then digested with Bst1107I and the ~7.6 kb AscI-Bst1107I (filled) fragment containing the deleted pol gene and the pTP gene was isolated (as described in Ex. 3) and ligated to Bst1107I-digested pAdBglIIAsc to generate pAdAscΔpolΔpTP.

In order to reduce the packaging of the above helper viruses, the pol− or pol−, pTP− helper viruses can be modified to incorporate loxP sequences on either side of the packaging signals as outlined in Example 7. The loxP-containing pol− or pol−, pTP− shuttle vectors (pTP− shuttle vectors may also be employed) are cotransfected into 293 cells expressing Cre recombinase and pol or Cre recombinase, pol and pTP, respectively along with an appropriate E1− viral DNA-TPC (the E1− viral DNA may also contain deletions elsewhere in the genome such as in the E4 genes or in the E2a gene as packaging cell lines expressing the E4 ORF 6 or 6/7 and lines expressing E2a genes are avaialble) to generate helper virus containing loxP sites flanking the packaging signals as well as a deletion in the pol gene or the pol and pTP genes. The resulting helper virus(es) is used to cotransfect 293 cells expressing pol or pol and pTP along with the desired EAM construct. The resulting EAM preparation should contain little if any helper virus and any contaminating helper virus present would be replication defective and incapable of expressing viral late gene products. Helper viruses containing loxP sequences and deletions in all essential early genes may be employed in conjunction with Cre recombinanse-expressing cell lines expressing in trans the E1, E4 ORF 6, E2a, and E2b (e.g., Ad polymerase and pTP) proteins (the E3 proteins are dispensible for growth in culture). Cell lines coexpressing E1, polymerase and pTP are provided herein. Cell lines expressing E1 and E4 proteins have been recently described [Krougliak and Graham (1995) Hum. Gene Ther. 6:1575 and Wang et al. (1995) Gene Ther. 2:775] and cell lines expressing E1 and E2a proteins have been recently described [Zhou et al. (1996) J. Virol. 70:7030]. Therefore, a cell line co-expressing E1, E2a, E2b, and E4 is consructed by introduction of expression plasmids containing the E2a and E4 coding regions into the E1−, Ad polymerase- and pTP-expressing cell lines of the present invention. These packaging cell lines are used in conjunction with helper viruses containing deletions in the E1, E2a, E2b and E4 regions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A mammalian cell line, comprising:

a) a recombinant plasmid, comprising, in operable combination:
   i) a plasmid backbone, comprising an origin of replication, an antibiotic resistance gene and a eukaryotic promoter element,
   ii) left and right inverted terminal repeats (ITRs) of adenovirus, said ITRs each having a 5' and a 3' end and arranged in a tail to tail orientation on said plasmid backbone,
   iii) an adenovirus packaging sequence, said packaging sequence having a 5' and a 3' end and linked to one of said ITRs, and
   iv) a gene of interest operably linked to said promoter element; and a helper adenovirus comprising i) a first and a second loxP sequences, and ii) the adenovirus packaging sequence, said packaging sequence having a 5' and a 3' end, wherein said first loxP sequence is linked to said 5' end of said packaging sequence and said second loxP sequence is linked to said 3' end of said packaging sequence.

2. The cell line of claim 1, wherein said helper adenovirus further comprises at least one adenovirus gene coding region.

3. The cell line of claim 1, wherein said gene of interest is the dystrophin cDNA gene.

4. A method of producing an adenovirus minichromosome, comprising:

1) providing a mammalian cell line containing:
   a) a recombinant plasmid, comprising, in operable combination, i) a plasmid backbone, comprising an origin of replication, an antibiotic resistance gene and a eukaryotic promoter element, ii) left and right inverted terminal repeats (ITR) of adenovirus, said ITRs each having a 5' and a 3' end and arranged in a tail to tail orientation on said plasmid backbone, iii) an adenovirus packaging sequence, said packaging sequence having a 5' and a 3' end and linked to one of said ITRs, and iv) a gene of interest operably linked to said promoter element; and
   b) a helper adenovirus comprising i) a first and a second loxP sequences, ii) at least one adenovirus gene coding region and iii) the adenovirus packaging sequence, said packaging sequence having a 5' and a 3' end, wherein said first loxP sequence is linked to said 5' end of said packaging sequence and said second loxP sequence is linked to said 3' end of said packaging sequence; and 2) growing said cell line under conditions such that said adenovirus gene coding region is expressed and said recombinant plasmid directs the production of at least one adenovirus minichromosome.

5. The method of claim 4, wherein said adenovirus minochromosome is encapsidated.

6. The method of claim 5, further comprising 3) recovering said encapsidated adenovirus minichromosome.

7. The method of claim 6, further comprising 4) purifying said recovered encapsidated adenovirus minichromosome.

8. A method of expressing a gene of interest, comprising:

1) providing a mammalian cell line containing:
   a) a recombinant plasmid, comprising, in operable combination, i) a plasmid backbone, comprising an origin of replication, an antibiotic resistance gene and a eukaryotic promoter element, ii) left and right inverted terminal repeats (ITRs) of adenovirus, said ITRs each having a 5' and a 3' end and arranged in a tail to tail orientation on said plasmid backbone, iii) an adenovirus packaging sequence, said packaging sequence having a 5' and a 3' end and linked to one of said ITRs, and iv) a gene of interest operably linked to said promoter element; and
   b) a helper adenovirus comprising i) a first and a second loxP sequences, ii) at least one adenovirus gene coding region and iii) the adenovirus packaging sequence, said packaging sequence having a 5' and a 3' end, wherein said first loxP sequence is linked to said 5' end of said packaging sequence and said second loxP sequence is linked to said 3' end of said packaging sequence;

2) growing said cell line under conditions such that said adenovirus gene coding region is expressed and said recombinant plasmid directs the production of at least one encapsidated adenovirus minichromosome;

3) recovering said encapsidated adenovirus minichromosome;

4) purifying said recovered encapsidated adenovirus minichromosome; and 5) administering said purified encapsidated adenovirus minichromosome to a host, such that the gene of interest is expressed.

9. The method of claim 8, wherein said host is a mammal.

10. The method of claim 9, wherein said mammal is a human.

* * * * *

UNITED STATES PATENT AND TRADEMARK OFFICE
CERTIFICATE OF CORRECTION

PATENT NO. : 6,057,158
DATED : May 2, 2000
INVENTOR(S) : Jeffrey S. Chamberlain et al.

It is certified that error appears in the above-identified patent and that said Letters Patent is hereby corrected as shown below:

Title page,
Title, please insert -- IMPROVED -- before "ADENOVIRUS."

Column 1,
Line 2, please insert -- IMPROVED -- before "ADENOVIRUS."

Column 13,
Line 28, please delete "inmnuno-incompetent" and insert -- immuno-incompetent --.

Column 15,
Line 17, please delete "8.5 kb" and insert -- ~ 8.5 kb --.

Column 16,
Lines 43 and 51, please delete "Me" and insert -- Mass. --.

Column 17,
Line 52, please delete "SVA40" and insert -- SV-40 --.
Line 65, please delete "As" and insert -- Ad --.

Column 20,
Line 18, please delete "2.5-3.0' $10^6$" and insert -- 2.5-3.0 x $10^6$ --.
Line 66, please delete "13-9" and insert -- B-9 --.

Column 21,
Line 10, please delete "33.5° C" and insert -- 38.5 °C --.

Column 25,
Line 2, please delete "he" and insert -- be --.
Lines 41, 50 and 57, please delete "h5sub100" and insert -- H5sub100 --.

Column 26,
Lines 4 and 14, please delete "h5sub100" and insert -- H5sub100 --.

Column 28,
Line 53, please delete "pol" and insert -- pol$^-$ --.

Column 32,
Line 41, please insert -- vAD -- between "Recombinant" 'and "vectors."

UNITED STATES PATENT AND TRADEMARK OFFICE
CERTIFICATE OF CORRECTION

PATENT NO. : 6,057,158
DATED : May 2, 2000
INVENTOR(S) : Jeffrey S. Chamberlain et al.

It is certified that error appears in the above-identified patent and that said Letters Patent is hereby corrected as shown below:

Column 34,
Line 38, please delete "pAd513dys" and insert -- pAd5βdys --.

Column 37,
Line 19, please delete "myc" and insert -- mdx --.
Line 33, please delete "B-FGF" and insert -- b-FGF --.

Column 41,
Line 48, please delete "pLC" and insert -- pIC --.

Signed and Sealed this

Eleventh Day of September, 2001

Attest:

NICHOLAS P. GODICI
Attesting Officer
Acting Director of the United States Patent and Trademark Office